US008653238B2

(12) United States Patent
Wender et al.

(10) Patent No.: US 8,653,238 B2
(45) Date of Patent: Feb. 18, 2014

(54) COMPOSITIONS AND METHODS FOR TRANSPORT OF MOLECULES WITH ENHANCED RELEASE PROPERTIES ACROSS BIOLOGICAL BARRIERS

(75) Inventors: Paul A. Wender, Palo Alto, CA (US); Elena A. Goun, Palo Alto, CA (US); Lisa R. Jones, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 506 days.

(21) Appl. No.: 12/280,683

(22) PCT Filed: Feb. 27, 2007

(86) PCT No.: PCT/US2007/005375
§ 371 (c)(1),
(2), (4) Date: Jan. 13, 2009

(87) PCT Pub. No.: WO2008/069824
PCT Pub. Date: Jun. 12, 2008

(65) Prior Publication Data
US 2010/0255499 A1 Oct. 7, 2010

Related U.S. Application Data

(60) Provisional application No. 60/777,341, filed on Feb. 27, 2006.

(51) Int. Cl.
*A61K 47/48* (2006.01)
*C07K 7/00* (2006.01)
(52) U.S. Cl.
USPC ............................. 530/329; 514/449; 514/543
(58) Field of Classification Search
None
See application file for complete search history.

(56) References Cited

U.S. PATENT DOCUMENTS

| 4,758,550 A | 7/1988 | Cardinaux et al. |
| 5,122,368 A | 6/1992 | Greenfield et al. |
| 6,306,993 B1 * | 10/2001 | Rothbard et al. ............. 526/304 |
| 6,495,663 B1 * | 12/2002 | Rothbard et al. ............. 530/329 |
| 6,593,292 B1 * | 7/2003 | Rothbard et al. ............. 514/1.2 |
| 7,056,942 B2 * | 6/2006 | Hildesheim et al. ........... 514/411 |
| 7,585,834 B2 * | 9/2009 | Wender et al. ................. 514/1.1 |
| 2003/0032593 A1 * | 2/2003 | Wender et al. ................. 514/12 |

FOREIGN PATENT DOCUMENTS

| WO | WO 94/05282 | * | 3/1994 |
| WO | WO 2004/069159 | * | 8/2004 |
| WO | WO 2006/012527 | * | 2/2006 |

OTHER PUBLICATIONS

Kirschberg et al. "Arginine-Based Molecular Transporters: The Synthesis and Chemical Evaluation of Releasable Taxol-Transporter Conjugates," Org. Lett., 2003, vol. 5, issue 19, pp. 3459-3462.*
Vippagunta et al. "Crystalline Solids," Advanced Drug Delivery Reviews, 2001, vol. 48, pp. 3-26.*
Vrudhula et al., "Reductively activated disulfide prodrugs of paclitaxel," Bioorganic & Medicinal Chemistry Letters, 2002, vol. 12, issue 24, pp. 3591-3594.*
International Search Report, dated Sep. 29, 2008.
Wender et al., Beyond Cell Penetrating Peptide: Designed Molecular Transporters, Drug Discovery Today Technology, 2012, pp. 49-55, vol. 9, issue 1.
Wender et al., Taxol-oligoarginine conjugates overcome drug resistance in-vitro in human ovarian carcinoma, Gynecologic Oncology, 2012, pp. 118-123, vol. 1.
Stanzl et al., Fifteen Years of Cell-Penetrating, Guanidinium-Rich Molecular Transporters: Basic Science, Research Tools, and Clinical Applications, Accounts of Chemical Research, May 22, 2013.

* cited by examiner

*Primary Examiner* — Shafiqul Haq
*Assistant Examiner* — Galina Yakovleva
(74) *Attorney, Agent, or Firm* — Thomas | Horstemeyer, LLP

(57) ABSTRACT

Conjugates of a cargo molecule with a transporter molecule are disclosed, where the cargo molecule and the transporter molecule are linked covalently by a releasable linker. The cargo of the conjugate can be a biologically active agent or a reporter molecule. The transporter modulates the transport of the cargo across a biological barrier (e.g., a cell membrane) compared to the transport of the unconjugated cargo. Releasable linkers suitable for rapid and facile conjugation to various types of cargo and transporters are also disclosed, along with methods for using the linkers in the synthesis of conjugates.

14 Claims, 22 Drawing Sheets

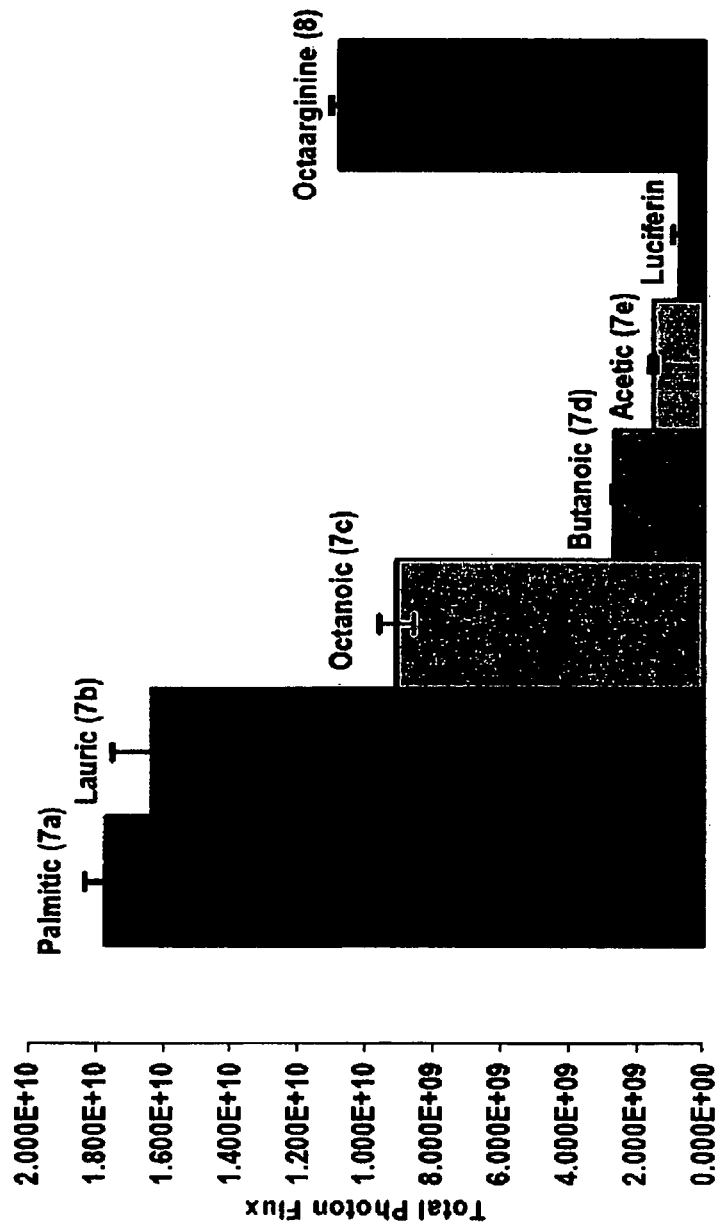

COMPOSITIONS AND METHODS FOR TRANSPORT OF MOLECULES WITH ENHANCED RELEASE PROPERTIES ACROSS BIOLOGICAL BARRIERS

CROSS-REFERENCE TO RELATED APPLICATIONS

This application is a National Phase application under 35 U.S.C. §371 of International Application No. PCT/US2007/005375 filed Feb. 27, 2007 and claims the benefit of U.S. Provisional Application No. 60/777,341 filed Feb. 27, 2006, the disclosures of which are incorporated herein by reference in their entirety.

CROSS REFERENCE TO RELATED APPLICATIONS

This application claims priority benefit of U.S. provisional patent application No. 60/777,341, filed Feb. 27, 2006. The content of that application is hereby incorporated by reference herein in its entirety.

STATEMENT REGARDING FEDERALLY SPONSORED RESEARCH OR DEVELOPMENT

This invention was made with Government support under contracts CA31841 and CA31845 awarded by the National Institutes of Health. The government has certain rights in the invention.

TECHNICAL FIELD

This application pertains to compositions of the form CARGO-LINKER-TRANSPORTER comprising conjugates of cargo molecules (such as biologically active molecules or reporter molecules) with transporter agents, linked by a releasable moiety, which are suitable for transport across a biological barrier (such as a cell membrane or tissue). This application also pertains to methods for synthesis of such conjugates and for the study of their effectiveness in cells and animals.

BACKGROUND

Pharmaceuticals and other biologically active molecules generally must cross biological barriers in order to be effective. For example, drugs or probes which are intended to interact with intracellular targets must cross the plasma membrane of the cell in order to produce the desired effect. Certain drugs may need to traverse other biological barriers, such as the stratum corneum of the skin for topically-applied agents. Since biological barriers such as the plasma membrane are generally composed primarily of non-polar components, the biologically active molecule must be relatively non-polar in order to be able to traverse the barrier by passive diffusion. However, the drug or probe must also be sufficiently polar in order to be soluble in blood plasma or extracellular fluid. These opposing requirements result in a relatively narrow range of polarity for biological agents and probes or reporter molecules which are intended to act within the cell, or which must traverse a biological membrane or other biological barrier to exert an effect.

Various solutions to this problem are described in U.S. Pat. No. 6,306,993, U.S. Pat. No. 6,495,663, U.S. Pat. No. 6,593,292, U.S. Pat. No. 6,669,951, U.S. Pat. No. 6,730,293 and U.S. Pat. No. 6,759,387, and in Rothbard et al., Nat. Med. 6:1253 (2000); Kirschberg et al., Org. Lett. 5:3459 (2003); Samuel et al., Proc. Natl. Acad. Sci. U.S.A. 100:14281 (2003); Chen et al., Chem. Biol. 8:1123 (2001); Kim et al., J. Immunol. 159:1666 (1997); Robbins et al., BioTechniques 33:190, 194 (2002); Siprashvili et al., Hum. Gene Ther. 14:1225 (2003), and the various articles appearing in Advanced Drug Delivery Reviews (2005), volume 57, particularly those from pages 487 to 665. These publications describe delivery-enhancing transporters; that is, transporter molecules which enhance the ability of a biologically active molecule to cross a biological barrier, such as the cell membrane or the stratum corneum.

It is desirable to have an efficient system for producing conjugates of cargo molecules, such as biologically active molecules, with transporter molecules. The conjugate of the cargo with the transporter molecule is desirably effected by a linker which is stable under conditions of storage and administration, but which releases the cargo within the cell or other target environment. It is also desirable to have a rapid, relevant and economical system for screening transporter molecules for their ability to transport biologically active molecules across a biological membrane or other biological barrier. Embodiments of the current invention addresses these objectives, and provide additional advantages, as well as providing for various compositions and methods.

DISCLOSURE OF THE INVENTION

In one embodiment, the invention embraces a conjugate of the form:

(CARGO)-(RELEASABLE LINKER)-(TRANSPORTER) where the cargo of the conjugate can be a biologically active agent or a reporter molecule, and where the transporter modulates the transport of the cargo across a biological barrier compared to the transport of the unconjugated cargo. In one embodiment, the transporter increases the amount or rate of transport of the cargo across a biological barrier compared to the transport of the unconjugated cargo. In another embodiment, the transporter slows the amount or rate of transport of the cargo across a biological barrier compared to the transport of the unconjugated cargo. In one embodiment, the biological barrier is a biological membrane. In another embodiment, the biological barrier is the cell membrane. In another embodiment, the biological barrier is the stratum corneum. In another embodiment, the invention embraces releasable linkers suitable for facile and inexpensive conjugation to various types of cargo and transporters. In another embodiment, the invention embraces methods for using the linkers in the synthesis of conjugates. In another embodiment, the invention embraces methods for determining the efficacy of a transporter, by assaying the transporter's efficacy at effecting transport of a reporter molecule across a biological barrier, e.g. a biological membrane such as a cell membrane.

In one embodiment, the cargo molecule and the transporter molecule are different molecules; that is, the same molecule cannot serve as both cargo molecule and transporter molecule. In another embodiment, the cargo molecule and the transporter molecule are different portions of the cargo-releasable linker-transporter conjugate; that is, the same portion of the conjugate cannot serve as both cargo and transporter. In one embodiment, the transporter molecule is a polyamine. In another embodiment, the transporter molecule is not a polyamine.

In one embodiment, the invention embraces a composition for transporting a cargo molecule across a biological barrier comprising a cargo molecule; a transporter molecule; and a releasable linker of the form

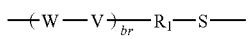

which covalently links the cargo molecule and the transporter molecule; where $R_1$ is an optionally substituted $C_1$-$C_8$ hydrocarbon group, an optionally substituted group of the form —CH2-O—(C=O)—$C_1$-$C_8$ hydrocarbyl, or an optionally substituted $C_1$-$C_8$ hetero chain group; W is —(C=C)—, —P(=O)(—OH)—, —P(=O)(—O$^-$)—, —P(=O)(—O$^-$ M$^+$)-, or —S(=O)$_2$—, where M$^+$ is one equivalent of a cation; V is O, NH, NR$_2$, CH$_2$, CHR$_2$, C(R$_2$)$_2$, or S; where R$_2$ is $C_1$-$C_4$ alkyl; and where br is an integer between 1 and 4 inclusive and indicates the number of "branches" on the $R_1$ group; or any salt, solvate, or stereoisomer thereof. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl. The cargo molecule can be selected from the group consisting of a biologically active molecule and a reporter molecule. The variable br is preferably 1 or 2, more preferably 1. When two (—W—V—) groups are present, they can be attached to (branch from) the same atom in the $R_1$ group, or they can be attached to (branch from) two different atoms in the $R_1$ group. When three (—W—V—) groups are present, all three can be attached to (branch from) the same atom in the $R_1$ group, or they can be attached to (branch from) three different atoms in the $R_1$ group, or two can be attached to (branch from) the same atom and one can be attached to (branch from) a different atom. When four (—W—V—) groups are present, they can be attached to (branch from) two or more different atoms in the $R_1$ group.

In one embodiment, the linker is of the form:

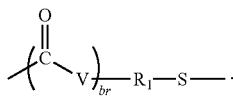

In one embodiment, the linker is of the form:

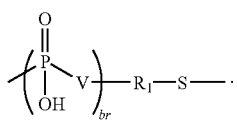

In one embodiment, the linker is of the form:

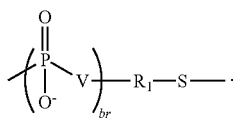

In one embodiment, the linker is of the form:

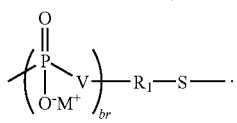

In one embodiment, the linker is of the form:

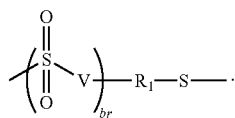

In one embodiment, the invention embraces a composition for transporting a cargo molecule across a biological barrier comprising a cargo molecule; a transporter molecule; and a releasable linker of the form

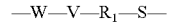

which covalently links the cargo molecule and the transporter molecule; where $R_1$ is an optionally substituted $C_1$-$C_8$ hydrocarbon group, an optionally substituted group of the form —CH2-O—(C=O)—$C_1$-$C_8$ hydrocarbyl, or an optionally substituted $C_1$-$C_8$ hetero chain group; W is —(C=O)—, —P(=O)(—OH)—, —P(=O)(—O$^-$)—, —P(=O)(—O$^-$ M$^+$)-, or —S(=O)2-, where M$^+$ is one equivalent of a cation; V is O, NH, NR$_2$, CH$_2$, CHR$_2$, C(R$_2$)$_2$, or S, and R$_2$ is $C_1$-$C_4$ alkyl; or any salt, solvate, or stereoisomer thereof. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl. The cargo molecule can be selected from the group consisting of a biologically active molecule and a reporter molecule.

In another embodiment, when V is O, HN, NR$_2$, or S, $R_1$ contains a carbon atom of the form —C(CH$_3$)$_2$— (i.e., a dimethyl-substituted carbon, or gem-dimethyl carbon) immediately adjacent to the V atom. In another embodiment, when V is C(R$_2$)$_2$, both R$_2$ groups are methyl (i.e., a dimethyl-substituted carbon, or gem-dimethyl carbon).

In one embodiment, the linker is of the form:

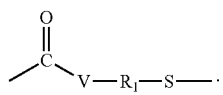

In one embodiment, the linker is of the form:

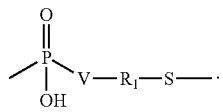

In one embodiment, the linker is of the form:

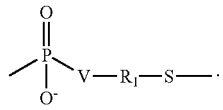

In one embodiment, the linker is of the form:

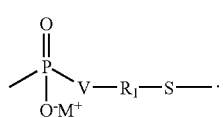

In one embodiment, the linker is of the form:

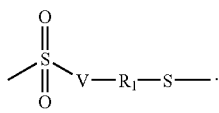

In one embodiment, the invention embraces a composition for transporting a cargo molecule across a biological barrier comprising a cargo molecule; a transporter molecule; and a releasable linker of the form

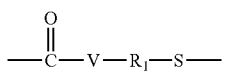

which covalently links the cargo molecule and the transporter molecule; where $R_1$ is an optionally substituted $C_1$-$C_8$ hydrocarbon group, an optionally substituted group of the form —CH2-O—(C=O)—$C_1$-$C_8$ hydrocarbyl, or an optionally substituted $C_1$-$C_8$ hetero chain group; V is O, NH, $NR_2$, $CH_2$, $CHR_2$, $C(R_2)_2$, or S; and $R_2$ is $C_1$-$C_4$ alkyl; or any salt, solvate, or stereoisomer thereof. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl. The cargo molecule can be selected from the group consisting of a biologically active molecule and a reporter molecule.

In another embodiment, the composition comprising a cargo molecule, a transporter molecule, and a releasable linker covalently linking the cargo molecule and the transporter molecule, is of the form

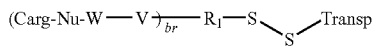

wherein Carg-Nu represents the residue of a cargo molecule "Carg-NuH"; and Transp-S represents the residue of a transporter molecule bearing a thiol group of the form "Transp-SH"; where $R_1$ is an optionally substituted $C_1$-$C_8$ hydrocarbon group, an optionally substituted group of the form —CH2-O—(C=O)—$C_1$-$C_8$ hydrocarbyl, or an optionally substituted $C_1$-$C_8$ hetero chain group; W is —(C=O)—, —P(=O)(—OH)—, —P(=O)(—O$^-$)—, —P(=O)(—O$^-$ M$^+$)-, or —S(=O)2-, V is O, NH, $NR_2$, $CH_2$, $CHR_2$, $C(R_2)_2$, or S; $R_2$ is $C_1$-$C_4$ alkyl; M$^+$ is one equivalent of a cation; and where br is an integer between 1 and 4 inclusive and indicates the number of "branches" on the $R_1$ group, or any salt, solvate, or stereoisomer thereof. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl.

In another embodiment, the composition comprising a cargo molecule; a transporter molecule; and a releasable linker covalently linking the cargo molecule and the transporter molecule is of the form

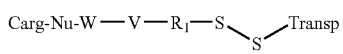

wherein Carg-Nu represents the residue of a cargo molecule "Carg-NuH"; and Transp-S represents the residue of a transporter molecule bearing a thiol group of the form "Transp-SH"; where $R_1$ is an optionally substituted $C_1$-$C_8$ hydrocarbon group, an optionally substituted group of the form —CH2-O—(C=O)—$C_1$-$C_8$ hydrocarbyl, or an optionally substituted $C_1$-$C_8$ hetero chain group; W is —(C=O)—, —P(=O)(—OH)—, —P(=O)(—O$^-$)—, —P(=O)(—O$^-$ M$^+$)-, or —S(=O)2-, where M$^+$ is one equivalent of a cation; V is O, NH, $NR_2$, $CH_2$, $CHR_2$, $C(R_2)_2$, or S; $R_2$ is $C_1$-$C_4$ alkyl; or any salt, solvate, or stereoisomer thereof. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl.

In another embodiment, the composition comprising a cargo molecule; a transporter molecule; and a releasable linker covalently linking the cargo molecule and the transporter molecule is of the form

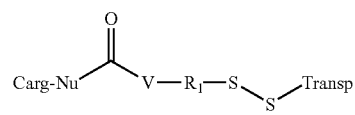

(I)

wherein Carg-Nu represents the residue of a cargo molecule "Carg-NuH"; and Transp-S represents the residue of a transporter molecule bearing a thiol group of the form "Transp-SH"; where $R_1$ is an optionally substituted $C_1$-$C_8$ hydrocarbon group, an optionally substituted group of the form —CH2-O—(C=O)—$C_1$-$C_8$ hydrocarbyl, or an optionally substituted $C_1$-$C_8$ hetero chain group; V is O, NH, $NR_2$, $CH_2$, $CHR_2$, $C(R_2)_2$, or S; and $R_2$ is $C_1$-$C_4$ alkyl; or any salt, solvate, or stereoisomer thereof. In one embodiment, V is O. In one embodiment, V is NH. In one embodiment, V is $CH_2$. In one embodiment, V is S. In one embodiment, $R_1$ is $C_1$-$C_8$ hydrocarbon. In one embodiment, $R_1$ is $C_1$-$C_8$ alkyl. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl.

In another embodiment, V is O and $R_1$ is $C_1$-$C_8$ alkyl. In one embodiment, $R_1$ is —$CH_2CH_2$—. In one embodiment, $R_1$ is —$CH_2CH_2CH_2$—. In one embodiment, $R_1$ is —$CH_2CH_2CH_2CH_2$—.

In another embodiment, (CARGO)-(RELEASABLE LINKER)-(TRANSPORTER) is of the form:

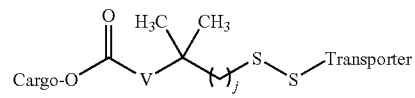

where V is O, NH, $NR_2$, $CH_2$, $CHR_2$, $C(R_2)_2$, or S, preferably O, NH, or $CH_2$; and j is an integer selected from 1 to 8 inclusive, preferably 1 or 2;

or

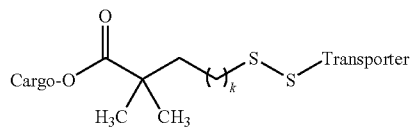

where k is an integer selected from 0 to 8 inclusive, preferably 1 or 2.

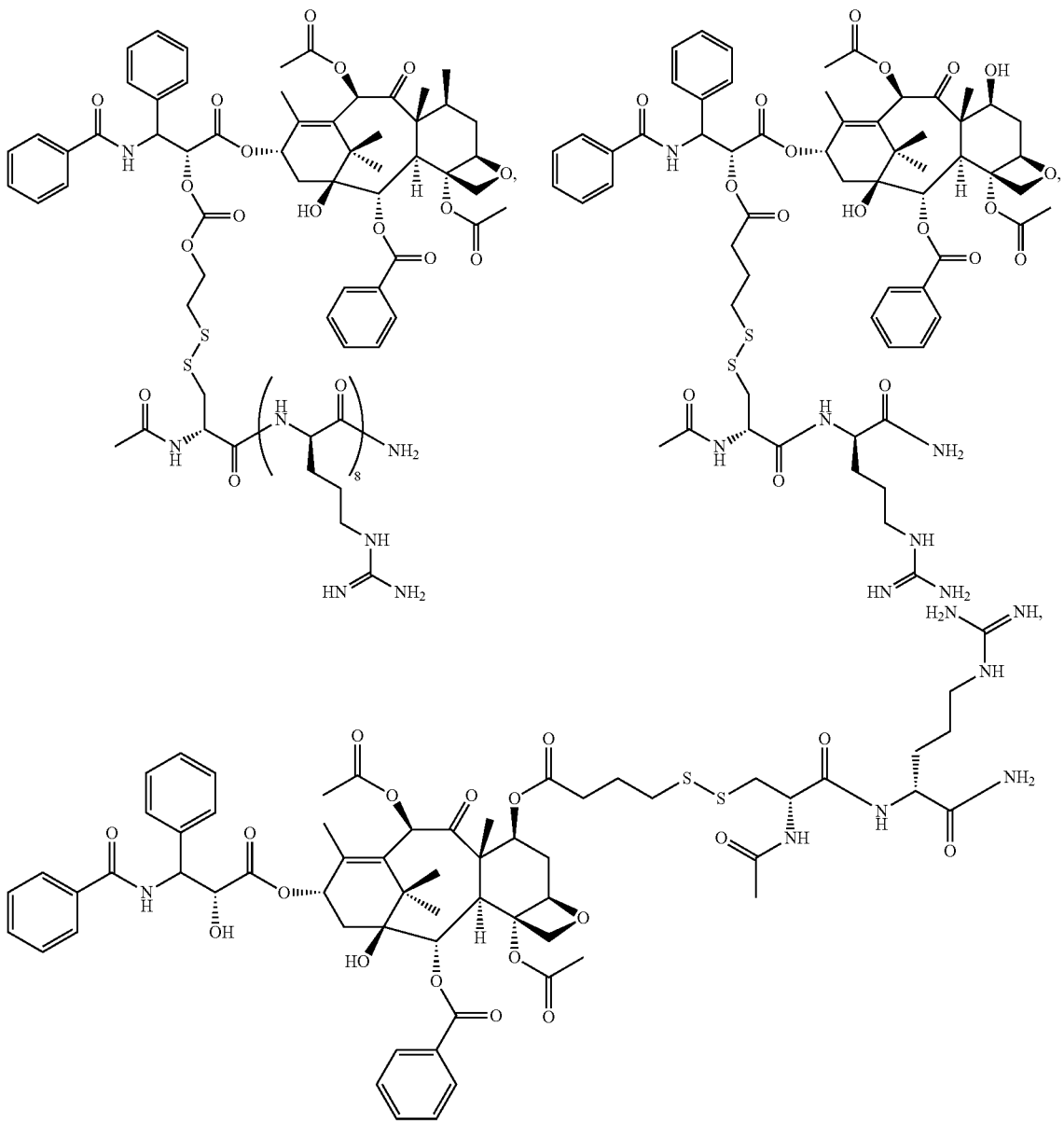

In another embodiment, -Nu- is —O—, —NH—, —NR$_2$,—, or —S—, where R$_2$ is C$_1$-C$_4$ alkyl.

In another embodiment, Carg-Nu is the residue of a reporter molecule, such as luciferin.

In another embodiment, Carg-Nu is the residue of a biologically active molecule. In one embodiment, the biologically active molecule is selected from the group consisting of a drug, a therapeutic agent, and a diagnostic agent. The drug or therapeutic agent can be paclitaxel or a polyamine. The drug or therapeutic agent can be a cyclosporine, such as cyclosporine A.

In another embodiment, CARGO-RELEASABLE LINKER-TRANSPORTER is selected from the group consisting of:

In another embodiment, the residue of a biologically active molecule is the residue of cyclosporine, attached at either the C2' hydroxyl or the C7 hydroxyl.

In another embodiment, CARGO-RELEASABLE LINKER-TRANSPORTER is selected from the group consisting of r8-Cys-S—S—(CH$_2$CH$_2$CH$_2$)—C(=O)—O—CH$_2$—O—C(=O)—OCsA and r8-Cys-S—S—(CH$_2$CH$_2$CH$_2$CH$_2$)—C(=O)—O—CH$_2$—O—C(=O)—

OCsA, wherein r8-Cys-S— indicates the residue of acetyl-D-Cys-(D-Arg)$_8$-NH$_2$ and —OCsA indicates the residue of cyclosporin A, and all salts, solvates, and stereoisomers thereof.

In another embodiment, the transporter is a lipid molecule, such as a fatty acid. In another embodiment, the lipid molecule is of the form (C$_7$-C$_{32}$ hydrocarbyl)-C(=O)—OH and acyl forms thereof, or (C$_7$-C$_{32}$ alkyl)-C(=O)—OH and (C$_7$-C$_{32}$ alkenyl)-C(=O)—OH and their acyl forms. In another embodiment, the lipid transporter is caprylic acid (octanoic acid), capric acid (decanoic acid), lauric acid (dodecanoic acid), myristic acid (tetradecanoic acid), palmitic acid (hexadecanoic acid), stearic acid (octadecanoic acid), arachidic acid (icosanoic acid), behenic acid (docosanoic acid), palmitoleic acid, oleic acid, linoleic acid, linolenic acid, arachidonic acid, eicosapentaenoic acid, docosahexaenoic acid, erucic acid, or the acyl forms thereof. In another embodiment, the lipid transporter comprising the "Transp-S" portion of the molecule is of the form (C$_7$-C$_{32}$ hydrocarbyl)-C(=O)-spacer-S—, where spacer is an optionally substituted C$_1$-C$_{10}$ alkyl, alkenyl, alkynyl, hydrocarbyl, heteroalkyl, heteroalkenyl, or heteroalkynyl group, or any combination of the above groups. In another embodiment, the lipid transporter comprising the "Transp-S" portion of the molecule is of the form

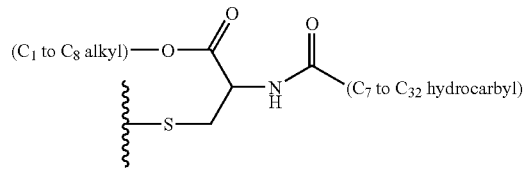

that is, where the fatty acid is acylated to the amino group of a cysteine (D or L cysteine), and the sulfhydryl side chain of the cysteine serves as the "S" portion of the "Transp-S" moiety, and any stereoisomers, salts, or solvates thereof.

In another embodiment where the transporter is a lipid molecule, such as a fatty acid, the cargo can be a cyclosporine, such as cyclosporine A. In another embodiment, the cyclosporine-linker-transporter conjugate can be selected from the group consisting of

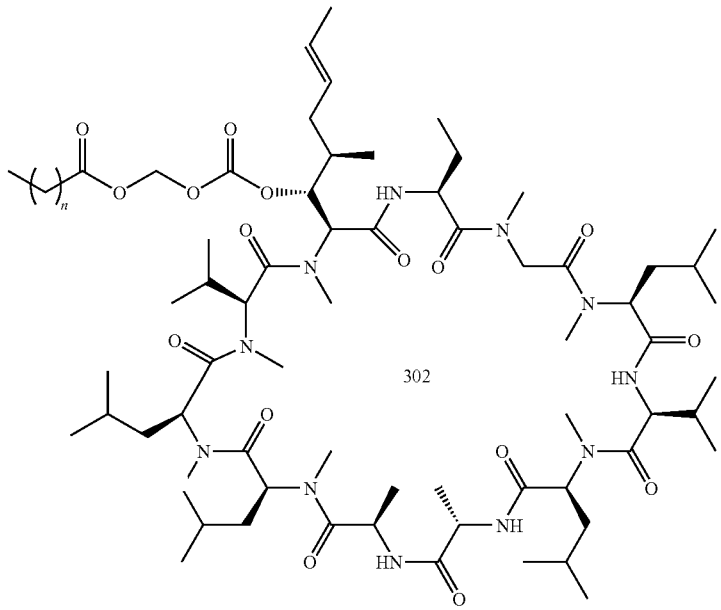

where n=6, where n=10, or where n=14,

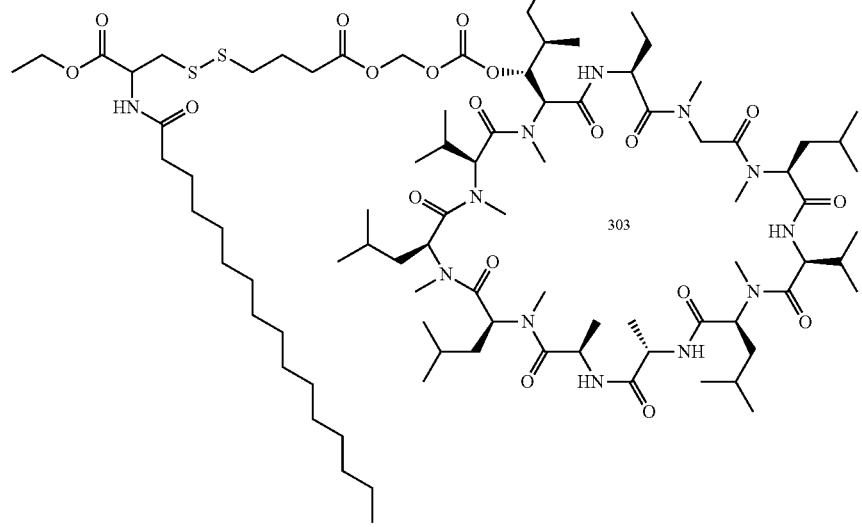

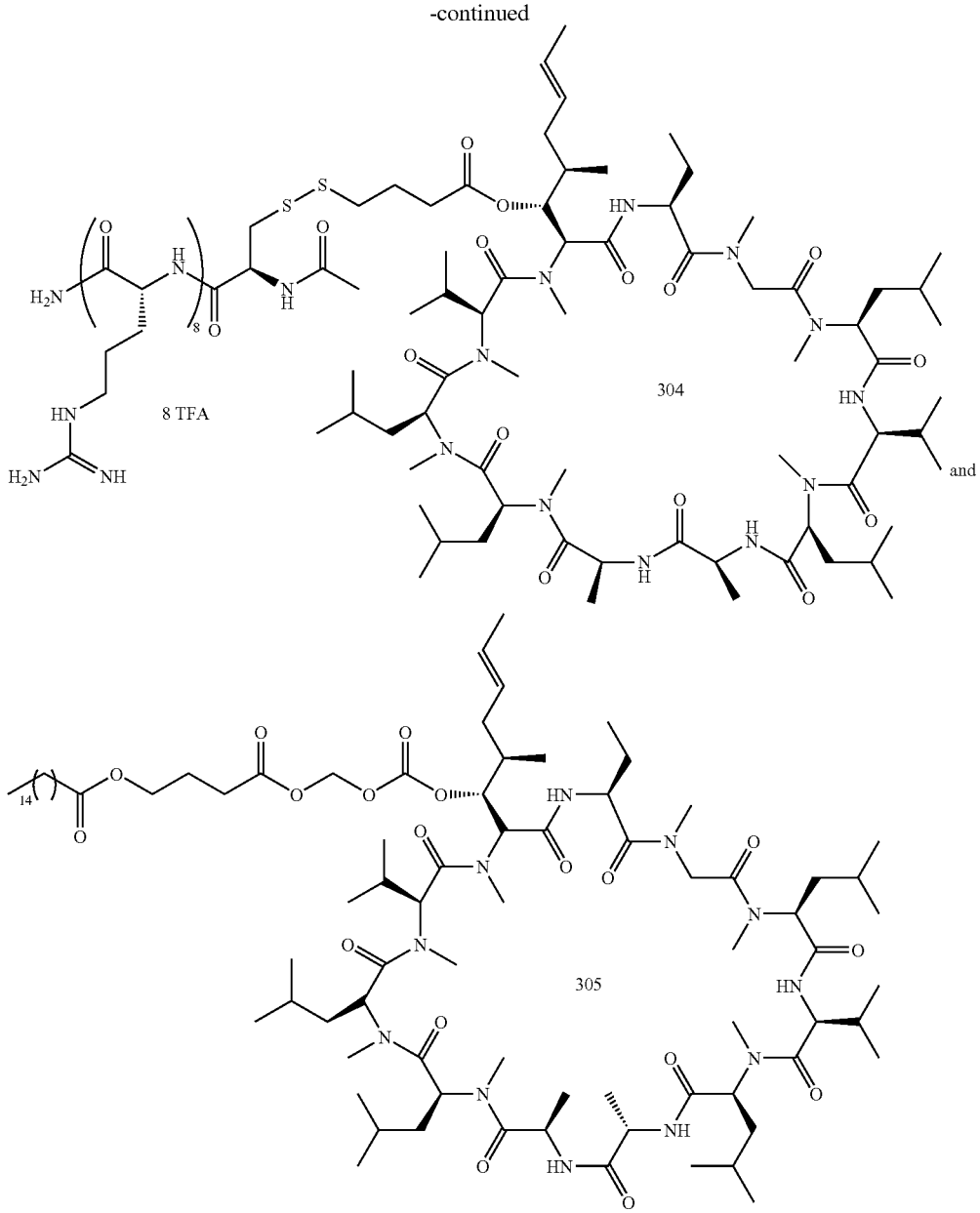

and any salt, solvate, or stereoisomer thereof.

In another embodiment, the invention embraces a method of making a conjugate of a cargo molecule "Carg-NuH" and a transport molecule bearing a thiol group of the form "Transp-SH" comprising the steps of reacting the compound Carg-NuH, the anion Carg-Nu(−), or the salt Carg-Nu(−)M$^+$, where -NuH or -Nu(−) is a nucleophilic moiety and M$^+$ is one equivalent of a cation, with a compound of the form $Y_1$—W—$Y_2$, where $Y_1$ and $Y_2$ are leaving groups and can be the same or different, and where W is —(C=O)—, —P(=O)(—OH)—, —P(=O)(—O$^-$)—, —P(=O)(—O$^-$M$^+$)-, —P(=O)(—O-PG)- where PG is a protecting group, or —S(=O)2-, to form a compound of the form Carg-Nu-W—Y1           (IIA-gb);

reacting a compound of the form (IIIA-gb)

where $R_1$ is an optionally substituted $C_1$-$C_8$ hydrocarbon group, an optionally substituted group of the form —CH2-O—(C=O)—$C_1$-$C_8$ hydrocarbyl, or an optionally substituted $C_1$-$C_8$ hetero chain group; V is O, NH, NR$_2$, CH$_2$, CHR$_2$, C(R$_2$)$_2$, or S; and R$_2$ is $C_1$-$C_4$ alkyl, where br is an integer between 1 and 4 inclusive and indicates the number of "branches" on the $R_1$ group, and TLGS is a thiol leaving group stabilizer; with a transporter group bearing a thiol of the form Transp-SH to form a compound of form (IVA-gb):

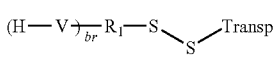

(IVA-gb)

and reacting the compound (IIA-gb) with the compound (IVA-gb) to form the conjugate of formula (Igb):

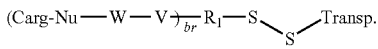

(Igb)

When W is —P(=O)(—O-PG)-, an additional step of removing the protecting group from the phosphate can be performed. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl.

In one embodiment, V is O. In one embodiment, V is NH. In one embodiment, V is $CH_2$. In one embodiment, V is S. In one embodiment, $R_1$ is $C_1$-$C_8$ hydrocarbon. In one embodiment, $R_1$ is $C_1$-$C_8$ alkyl.

In another embodiment, V is O and $R_1$ is $C_1$-$C_8$ alkyl. In one embodiment, $R_1$ is —$CH_2CH_2$—. In one embodiment, $R_1$ is —$CH_2CH_2CH_2$—. In one embodiment, $R_1$ is —$CH_2CH_2CH_2CH_2$—.

In another embodiment, -Nu- is —O—, —NH—, —$NR_2$—, or —S—, where $R_2$ is $C_1$-$C_4$ alkyl.

In another embodiment, $M^+$ is $Li^+$, $Na^+$, $K^+$, $Mg^{+2}$, or $Ca^{+2}$.

In another embodiment, TLGS is

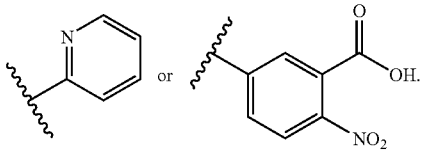

In another embodiment, the invention embraces a method of making a conjugate of a cargo molecule "Carg-NuH" and a transport molecule bearing a thiol group of the form "Transp-SH" comprising the steps of reacting a compound of the formula (IIgb):

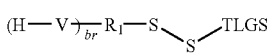

(IIgb)

where $R_1$ is an optionally substituted $C_1$-$C_8$ hydrocarbon group, an optionally substituted group of the form —CH2-O—(C=O)—$C_1$-$C_8$ hydrocarbyl, or an optionally substituted $C_1$-$C_8$ hetero chain group; V is O, NH, $NR_2$, $CH_2$, $CHR_2$, $C(R_2)_2$, or S; and $R_2$ is $C_1$-$C_4$ alkyl, where br is an integer between 1 and 4 inclusive and indicates the number of "branches" on the $R_1$ group, and TLGS is a thiol leaving group stabilizer; with an activating reagent of the form $Y_1$—W—$Y_2$, where W is —(C=O)—, —P(=O)(—OH)—, —P(=O)(—$O^-$)—, —P(=O)(—$O^-M^+$)-, —P(=O)(—O-PG)- where PG is a protecting group, or —S(=O)2-, to form a compound of the formula (IIIgb):

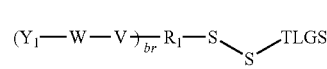

(IIIgb)

wherein $Y_1$ and $Y_2$ are leaving groups and can be the same or different; reacting (IIIg) with a nucleophilic compound of the form Carg-NuH, the anion Carg-Nu(-), or the salt Carg-Nu(-)$M^+$, where -NuH or -Nu(-) is a nucleophilic moiety and $M^+$ is one equivalent of a cation, to form a compound of the formula (IVgb):

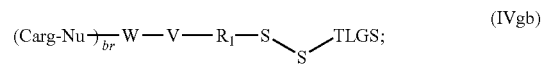

(IVgb)

and reacting (IVgb) with Transp-SH to form the conjugate of formula (Igb):

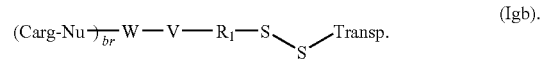

(Igb).

When W is —P(=O)(—O-PG)-, an additional step of removing the protecting group from the phosphate is performed. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl.

In one embodiment, W is —(C=O)—. In one embodiment, V is O. In one embodiment, V is NH. In one embodiment, V is $CH_2$. In one embodiment, V is S. In one embodiment, $R_1$ is $C_1$-$C_8$ hydrocarbon. In one embodiment, $R_1$ is $C_1$-$C_8$ alkyl.

In another embodiment, V is O and $R_1$ is $C_1$-$C_8$ alkyl. In one embodiment, $R_1$ is —$CH_2CH_2$—. In one embodiment, $R_1$ is —$CH_2CH_2CH_2$—. In one embodiment, $R_1$ is —$CH_2CH_2CH_2CH_2$—.

In another embodiment, -Nu- is —O—, —NH—, —$NR_2$—, or —S—, where $R_2$ is $C_1$-$C_4$ alkyl.

In another embodiment, $M^+$ is $Li^+$, $Na^+$, $K^+$, $Mg^{+2}$, or $Ca^{+2}$.

In another embodiment, TLGS is

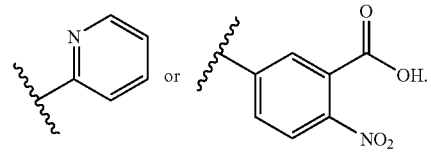 [SMILES: *c1ccccn1 ; *c1ccc([N+](=O)[O-])c(C(=O)O)c1]

In another embodiment, the invention embraces a method of making a conjugate of a cargo molecule "Carg-NuH" and a transport molecule bearing a thiol group of the form "Transp-SH" comprising the steps of reacting a compound of the formula (IIg):

(IIg)

where $R_1$ is an optionally substituted $C_1$-$C_8$ hydrocarbon group, an optionally substituted group of the form —CH2-O—(C=O)—$C_1$-$C_8$ hydrocarbyl, or an optionally substituted $C_1$-$C_8$ hetero chain group; V is O, NH, $NR_2$, $CH_2$, $CHR_2$, $C(R_2)_2$, or S; and $R_2$ is $C_1$-$C_4$ alkyl, and TLGS is a thiol leaving group stabilizer; with an activating reagent of the form $Y_1$—(C=O)—$Y_2$, to form a compound of the formula (IIIg):

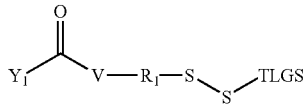
(IIIg)

wherein $Y_1$ and $Y_2$ are leaving groups and can be the same or different; reacting (IIIg) with a nucleophilic compound of the form Carg-NuH, the anion Carg-Nu(–), or the salt Carg-Nu(–)$M^+$, where -NuH or -Nu(–) is a nucleophilic moiety and $M^+$ is one equivalent of a cation, to form a compound of the formula (IVg):

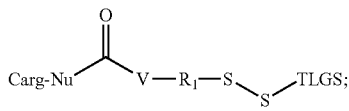
(IVg)

and reacting (IVg) with Transp-SH to form the conjugate of formula (I):

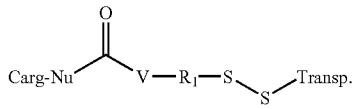
(I)

In one embodiment, V is O. In one embodiment, V is NH. In one embodiment, V is $CH_2$. In one embodiment, V is S. In one embodiment, $R_1$ is $C_1$-$C_8$ hydrocarbon. In one embodiment, $R_1$ is $C_1$-$C_8$ alkyl. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl.

In another embodiment, V is O and $R_1$ is $C_1$-$C_8$ alkyl. In one embodiment, $R_1$ is —$CH_2CH_2$—. In one embodiment, $R_1$ is —$CH_2CH_2CH_2$—. In one embodiment, $R_1$ is —$CH_2CH_2CH_2CH_2$—.

In another embodiment, -Nu- is —O—, —NH—, —$NR_2$—, or —S—, where $R_2$ is $C_1$-$C_4$ alkyl.

In another embodiment, $M^+$ is $Li^+$, $Na^+$, $K^+$, $Mg^{+2}$, or $Ca^{+2}$.

In another embodiment, TLGS is

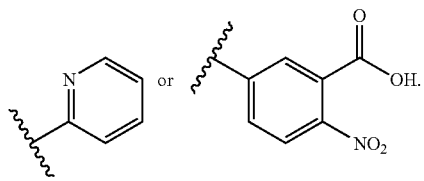 [SMILES: *c1ccccn1 ; *c1ccc([N+](=O)[O-])c(C(=O)O)c1]

In another embodiment, the invention embraces a method of making a conjugate of a cargo molecule "Carg-NuH" and a transport molecule bearing a thiol group of the form "Transp-SH" comprising the steps of reacting a compound of the formula (II):

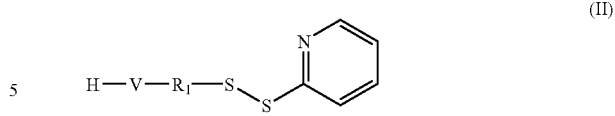
(II)

where $R_1$ is an optionally substituted $C_1$-$C_8$ hydrocarbon group, an optionally substituted group of the form —CH2-O—(C=O)—$C_1$-$C_8$ hydrocarbyl, or an optionally substituted $C_1$-$C_8$ hetero chain group; V is O, NH, $NR_2$, $CH_2$, $CHR_2$, $C(R_2)_2$, or S; and $R_2$ is $C_1$-$C_4$ alkyl; with an activating reagent of the form $Y_1$—(C=O)—$Y_2$, to form a compound of the formula (III):

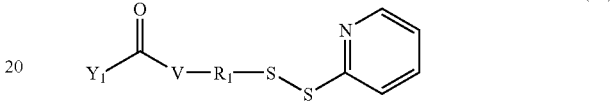
(III)

wherein $Y_1$ and $Y_2$ are leaving groups and can be the same or different; reacting (III) with a nucleophilic molecule of the form Carg-NuH, the anion Carg-Nu(–), or the salt Carg-Nu(–)$M^+$, where -NuH or -Nu(–) is a nucleophilic moiety and $M^+$ is one equivalent of a cation, to form a compound of the formula (IV):

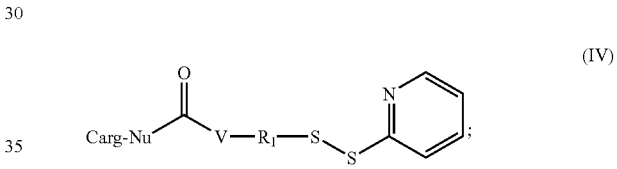
(IV)

and reacting (IV) with Transp-SH to form the conjugate of formula (I):

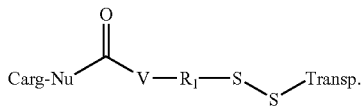
(I)

In one embodiment, V is O. In one embodiment, V is NH. In one embodiment, V is $CH_2$. In one embodiment, V is S. In one embodiment, $R_1$ is $C_1$-$C_8$ hydrocarbon. In one embodiment, $R_1$ is $C_1$-$C_8$ alkyl. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl:

In another embodiment, V is O and $R_1$ is $C_1$-$C_8$ alkyl. In one embodiment, $R_1$ is —$CH_2CH_2$—. In one embodiment, $R_1$ is —$CH_2CH_2CH_2$—. In one embodiment, $R_1$ is —$CH_2CH_2CH_2CH_2$—.

In another embodiment, -Nu- is —O—, —NH—, —$NR_2$—, or —S—, where $R_2$ is $C_1$-$C_4$ alkyl.

In another embodiment, $M^+$ is $Li^+$, $Na^+$, $K^+$, $Mg^{+2}$, or $Ca^{+2}$.

In another embodiment, the invention embraces a method of assaying a transporter-linker-cargo conjugate for cellular uptake and intracellular release, comprising contacting a cell or tissue sample with a transporter-linker-cargo conjugate, wherein the linker of the form

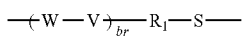

which covalently links the cargo molecule and the transporter molecule; where $R_1$ is an optionally substituted $C_1$-$C_8$ hydrocarbon group, an optionally substituted group of the form —CH2-O—(C=O)—$C_1$-$C_8$ hydrocarbyl, or an optionally substituted $C_1$-$C_8$ hetero chain group; W is —(C=O)—, —P(=O)(—OH)—, —P(=O)(—O$^-$)—, —P(=O)(—O$^-$ M$^+$)-, or —S(=O)2-, where M$^+$ is one equivalent of a cation; V is O, NH, NR$_2$, CH$_2$, CHR$_2$, C(R$_2$)$_2$, or S; where $R_2$ is $C_1$-$C_4$ alkyl; and where br is an integer between 1 and 4 inclusive and indicates the number of "branches" on the $R_1$ group; and wherein the cargo is a reporter molecule, for a period of time; and detecting cargo that has been transported into the cells or tissue; whereby the efficacy of the transporter in effecting transport is determined. In one embodiment, br is 1. In another embodiment, br is 2. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl.

In another embodiment, the invention embraces a method of assaying a transporter-linker-cargo conjugate for cellular uptake and intracellular release, comprising contacting a cell or tissue sample with a transporter-linker-cargo conjugate, wherein the linker is of the form:

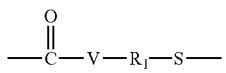

where $R_1$ is an optionally substituted $C_1$-$C_8$ hydrocarbon group, an optionally substituted group of the form —CH2-O—(C=O)—$C_1$-$C_8$ hydrocarbyl, or an optionally substituted $C_1$-$C_8$ hetero chain group; V is O, NH, NR$_2$, CH$_2$, CHR$_2$, C(R$_2$)$_2$, or S; and $R_2$ is $C_1$-$C_4$ alkyl; and wherein the cargo is a reporter molecule, for a period of time; and detecting cargo that has been transported into the cells or tissue; whereby the efficacy of the transporter in effecting transport is determined. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl.

In another embodiment, the invention embraces a method of assaying a transporter-linker-cargo conjugate for cellular uptake and intracellular release, comprising contacting a cell or tissue sample with a transporter-linker-cargo conjugate of the form

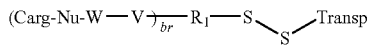

wherein Carg-Nu represents the residue of a cargo molecule "Carg-NuH"; and Transp-S represents the residue of a transporter molecule bearing a thiol group of the form "Transp-SH"; where $R_1$ is an optionally substituted $C_1$-$C_8$ hydrocarbon group, an optionally substituted group of the form —CH2-O—(C=O)—$C_1$-$C_8$ hydrocarbyl, or an optionally substituted $C_1$-$C_8$ hetero chain group; W is —(C=O)—, —P(=O)(—OH)—, —P(=O)(—O$^-$)—, —P(=O)(—O$^-$ M$^+$)-, or —S(=O)2-, V is O, NH, NR$_2$, CH$_2$, CHR$_2$, C(R$_2$)$_2$, or S; $R_2$ is $C_1$-$C_4$ alkyl; M$^+$ is one equivalent of a cation; and where br is an integer between 1 and 4 inclusive and indicates the number of "branches" on the $R_1$ group; wherein the cargo is a reporter molecule, for a period of time; and detecting cargo that has been transported into the cells or tissue, whereby the efficacy of the transporter in effecting transport is determined. In one embodiment, the cargo is luciferin. In one embodiment, br is 1. In another embodiment, br is 2. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl.

In another embodiment, the invention embraces a method of assaying a transporter-linker-cargo conjugate for cellular uptake and intracellular release, comprising contacting a cell or tissue sample with a transporter-linker-cargo conjugate of the form:

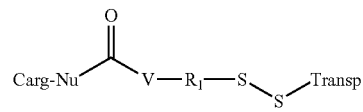

where $R_1$ is an optionally substituted $C_1$-$C_8$ hydrocarbon group, an optionally substituted group of the form —CH2-O—(C=O)—$C_1$-$C_8$ hydrocarbyl; or an optionally substituted $C_1$-$C_8$ hetero chain group; V is O, NH, NR$_2$, CH$_2$, CHR$_2$, C(R$_2$)$_2$, or S; and $R_2$ is $C_1$-$C_4$ alkyl; wherein the cargo is a reporter molecule, for a period of time; and detecting cargo that has been transported into the cells or tissue, whereby the efficacy of the transporter in effecting transport is determined. In one embodiment, the cargo is luciferin. In one embodiment, when $R_1$ is an optionally substituted group of the form —CH2-O—(C=O)—$C_1$-$C_8$ hydrocarbyl, V is O; preferably the $C_1$-$C_8$ hydrocarbyl group is selected from $C_2$ alkyl, $C_3$ alkyl, and $C_4$ alkyl.

For any of the conjugates, compositions, and methods above where the transporter is not otherwise specified, the transporter can be selected from Ac-D-Cys-(D-Arg)$_8$-CONH$_2$ and any stereoisomer, salt, or solvent thereof, where the thiol group of the Cys molecule corresponds to the thiol of the "HS-Transp" referenced above, and the remainder of Ac-D-Cys-(D-Arg)$_8$-CONH$_2$ corresponds to the "Transp" portion of "HS-Transp."

For all of the methods described above, the order of steps may be changed as long as such re-ordering provides the same product or result.

For all of the compounds and conjugates described above and herein, the invention further embraces a method of administering said compound or conjugate to a patient in a therapeutically effective amount. The administration can comprise contacting a cancer cell with a compound or conjugate of the invention, or administering the compound or conjugate of the invention in a manner such that the cancer cells of the patient are contacted with the compound or conjugate. In another embodiment of the method of administration, a drug conjugated to a transporter by a linker of the invention can be used to treat a cell line, cancer, or patient which/who is normally resistant to the free drug.

BRIEF DESCRIPTION OF THE DRAWINGS

FIG. 14B is a bar representation of the amount of luciferin delivered and released by topically administered lipidated transporter conjugates. Compounds are indicated by numbers as in FIG. 13 caption.

DETAILED DESCRIPTION OF THE INVENTION

Figure 1A:
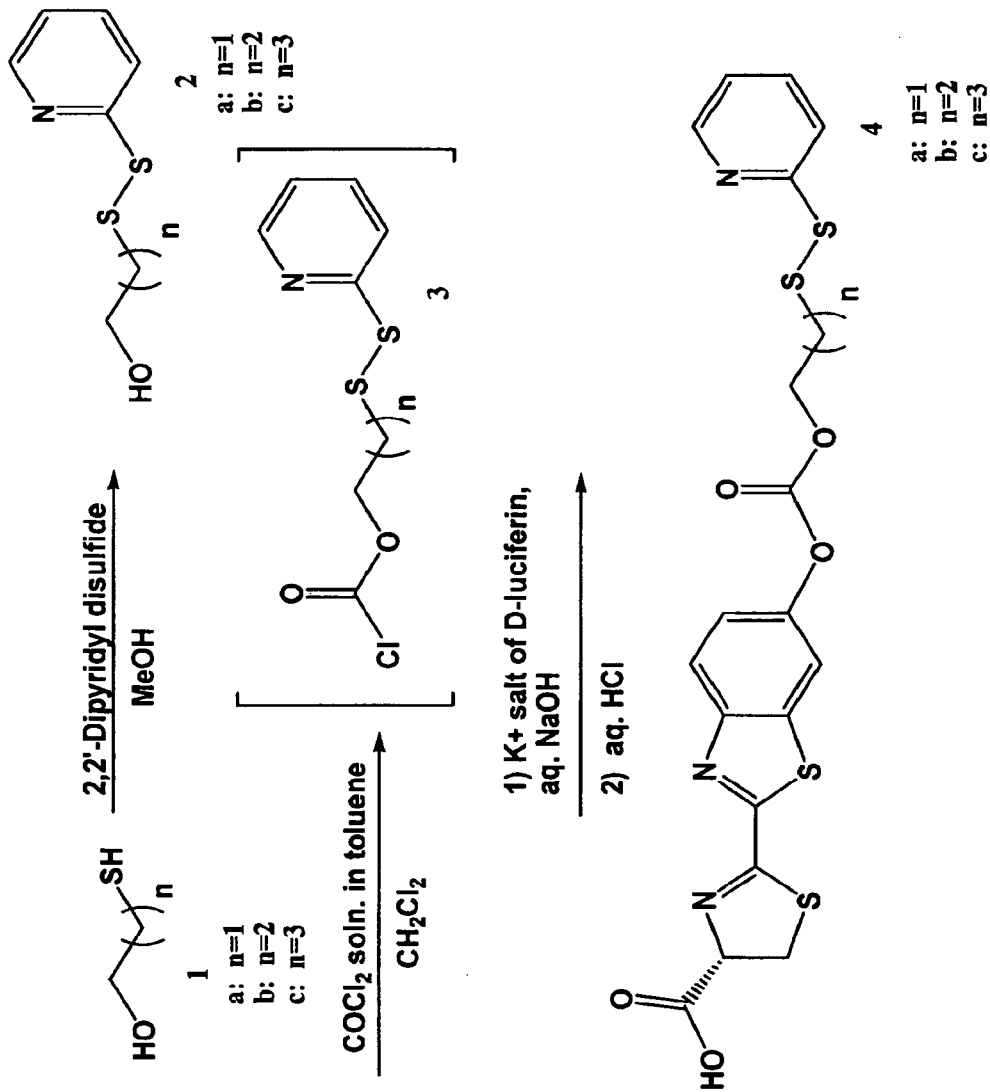
FIG. 1A shows a synthetic route to preparing disulfide-activated agents for conjugation with transporter polymers.

A "subject" or a "patient" refers to a vertebrate, preferably a mammal, more preferably a human.

"Treating" or "to treat" a disease using the methods of the invention is defined as administering one or more compounds, with or without additional therapeutic agents, in order to palliate, ameliorate, stabilize, reverse, slow, delay, prevent, reduce, or eliminate either the disease or the symptoms of the disease, or to retard or stop the progression of the disease or of symptoms of the disease. "Therapeutic use" of a compound is defined as using one or more compounds to treat a disease, as defined above. A "therapeutically effective amount" is an amount sufficient to treat a disease, as defined above. Prevention or suppression can be partial or total.

A "diagnostic agent" is an agent that aids in detecting, diagnosing, staging, or otherwise identifying the presence, extent, or stage of a disease.

By "residue" is meant the portion of a molecule remaining after it has reacted with a linker group. For example, in the reaction of Boc-NH—CH2-COOH with $H_2N$—CH($CH_3$)—COOMe (Boc-glycine with alanine methyl ester) to form Boc-NH—CH2-CO—NH—CH(CH$_3$)—COOMe, the "Boc-NH—CH2-CO—" portion is the residue of Boc-glycine and the "—NH—CH(CH$_3$)—COOMe" portion is the residue of alanine methyl ester.

A "biological barrier" is defined as a biological structure that prevents free diffusion of molecules. Biological barriers include, but are not limited to, the cell membrane, the nuclear membrane, organelle membranes, the stratum corneum, the corneal epithelium, and the blood-brain barrier.

The invention includes the compounds described herein or incorporated by reference herein, including any and all stereoisomers, salts, hydrates and solvates of the compounds described herein or incorporated by reference herein. The invention also includes the compounds described herein or incorporated by reference herein in their non-salt, non-hydrate/non-solvate form. Thus, while some compounds disclosed herein are depicted as salts, it is to be understood that the disclosure embraces all other salts, hydrates, and solvates of the compounds depicted therein, as well as the non-salt, non-hydrate/non-solvate form of the compound. Particularly preferred are pharmaceutically acceptable salts. Pharmaceutically acceptable salts are those salts which retain the biological activity of the free compounds and which are not biologically or otherwise undesirable. The desired salt of a basic compound may be prepared by methods known to those of skill in the art by treating the compound with an acid; such a salt can be the product of a reaction producing the compound. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base; such a salt can be the product of a reaction producing the compound. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dicyclohexylamine, dibenzylamine, N-ethylpiperidine, N,N'-dibenzylethylenediamine, and triethylamine salts. Salts of acidic compounds with amino acids, such as lysine salts, can also be prepared. Examples of solvates include, but are not limited to, hydrates, hemihydrates (½ H$_2$O), dihydrates, trihydrates, and alcoholates such as methanolates and ethanolates.

The invention also includes all polymorphs, crystalline forms, and non-crystalline forms of the compounds disclosed herein.

The invention also includes all stereoisomers of the compounds disclosed herein, including diastereomers and enantiomers in isolated form, as well as mixtures of stereoisomers in any proportion, including, but not limited to, racemic mixtures. Unless stereochemistry is explicitly indicated in a structure, the structure is intended to embrace all possible stereoisomers of the compound depicted. When a specific biologically active agent or reporter molecule is indicated, only the stereoisomers of the agent or reporter which retain the appropriate biological function or reporter/probe characteristics are intended.

The term "alkyl" refers to saturated aliphatic groups including straight-chain, branched-chain, cyclic groups, and combinations thereof, having the number of carbon atoms specified, or if no number is specified, having up to 12 carbon atoms, with preferred subsets of alkyl groups including $C_1$-$C_{12}$, $C_1$-$C_{10}$, $C_1$-$C_6$, and $C_1$-$C_8$ alkyl groups. "Straight-chain alkyl" or "linear alkyl" groups refers to alkyl groups that are neither cyclic nor branched, commonly designated as "n-alkyl" groups. Examples of alkyl groups include, but are not limited to, groups such as methyl, ethyl, n-propyl, isopropyl, butyl, n-butyl, isobutyl, sec-butyl, t-butyl, pentyl, n-pentyl, hexyl, heptyl, octyl, nonyl, decyl, undecyl, dodecyl, neopentyl, cyclopropyl, cyclobutyl, cyclopentyl, cyclohexyl, and adamantyl. Cyclic groups can consist of one ring, including, but not limited to, groups such as cycloheptyl, or multiple fused rings, including, but not limited to, groups such as adamantyl or norbornyl.

"Substituted alkyl" refers to alkyl groups substituted with one or more substituents including, but not limited to, groups such as halogen (fluoro, chloro, bromo, and iodo), alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkyl groups include, but are not limited to, —CF$_3$, —CF$_2$—CF$_3$, and other perfluoro and perhalo groups.

"Hydroxyalkyl" specifically refers to alkyl groups having the number of carbon atoms specified substituted with one —OH group. Thus, "$C_3$ linear hydroxyalkyl" refers to —CH$_2$CH$_2$CHOH—, —CH$_2$CHOHCH$_2$—, and —CHOHCH$_2$CH$_2$—.

The term "alkenyl" refers to unsaturated aliphatic groups including straight-chain (linear), branched-chain, cyclic groups, and combinations thereof, having the number of carbon atoms specified, or if no number is specified, having up to 12 carbon atoms, which contain at least one double bond (—C═C—). Examples of alkenyl groups include, but are not limited to, —CH$_2$—CH═CH—CH$_3$; and —CH$_2$—CH$_2$-cyclohexenyl, where the ethyl group can be attached to the cyclohexenyl moiety at any available carbon valence. The term "alkynyl" refers to unsaturated aliphatic groups including straight-chain (linear), branched-chain, cyclic groups, and combinations thereof, having the number of carbon atoms specified, or if no number is specified, having up to 12 carbon atoms, which contain at least one triple bond (—C≡C—). "Hydrocarbon," "hydrocarbon group," "hydrocarbon chain" or "hydrocarbyl" refers to any of straight-chain, branched-chain, or cyclic alkyl, alkenyl, or alkynyl groups, and any combination thereof. Hydrocarbon groups have the number of carbon atoms specified, or, if no number is specified, have between 1 and 12 carbon atoms. "Substituted alkenyl," "substituted alkynyl," and "substituted hydrocarbon chain" (or "substituted hydrocarbyl," "substituted hydrocarbon group," or "substituted hydrocarbon") refer to the respective group substituted with one or more substituents, including, but not limited to, groups such as halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

"Aryl" or "Ar" refers to an aromatic carbocyclic group having a single ring (including, but not limited to, groups such as phenyl) or multiple condensed rings (including, but not limited to, groups such as naphthyl or anthryl), and includes both unsubstituted and substituted aryl groups. "Substituted aryls" refers to aryls substituted with one or more substituents, including, but not limited to, groups such as alkyl, alkenyl, alkynyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

"Heteroalkyl," "heteroalkenyl," and "heteroalkynyl" refer to alkyl, alkenyl, and alkynyl groups, respectively, that contain the number of carbon atoms specified (or if no number is specified, having up to 12 carbon atoms) which contain one or more heteroatoms as part of the main, branched, or cyclic chains in the group. Heteroatoms include, but are not limited to, N, S, O, and P; N and O are preferred. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—CH$_3$, —O—CH$_2$—, —CH$_2$—O—CH$_2$—, —CH$_2$—CH$_2$—O—CH$_2$—, —S—CH$_2$—CH$_2$—CH$_2$—, —CH$_2$—CH(CH$_3$)—S—CH$_2$—, —CH$_2$—CH$_2$—NH—CH$_2$—CH$_2$—, 1-ethyl-6-propylpiperidino, 2-ethylthiophenyl, and morpholino. Examples of heteroalkenyl groups include, but are not limited to, groups such as —CH═CH—NH—CH(CH$_3$)—CH$_2$—.

A "hetero chain" or "hetero chain group" refers to any of a heteroalkyl, heteroalkenyl, or heteroalkynyl group, or any combination thereof, and has the number of carbon atoms specified (or if no number is specified, having up to 12 carbon atoms).

"Heteroaryl" or "HetAr" refers to an aromatic carbocyclic group having a single ring (including, but not limited to, examples such as pyridyl, thiophene, or furyl) or multiple condensed rings (including, but not limited to, examples such as imidazolyl, indolizinyl or benzothienyl) and having at least one hetero atom, including, but not limited to, heteroatoms such as N, O, P, or S, within the ring. Unless otherwise specified, heteroalkyl, heteroalkenyl, heteroalkynyl, and heteroaryl groups have between one and five heteroatoms and between one and twelve carbon atoms. "Substituted heteroalkyl," "substituted heteroalkenyl," "substituted heteroalkynyl," "substituted hetero chain," and "substituted heteroaryl" groups refer to heteroalkyl, heteroalkenyl, heteroalkynyl, hetero chain, and heteroaryl groups substituted with one or more substituents, including, but not limited to, groups such as alkyl, alkenyl, alkynyl, benzyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of such substituted groups include, but are not limited to, piperazine, substituted at a nitrogen or carbon by a phenyl or benzyl group, and attached to the remainder of the molecule by any available valence on a carbon or nitrogen, —NH—SO$_2$-phenyl, —NH—(C═O)O-alkyl, —NH—(C═O)O-alkyl-aryl, and —NH—(C═O)-alkyl. If chemically possible, the heteroatom(s) as well as the carbon atoms of the group can be substituted. The heteroatom(s) can also be in oxidized form, if chemically possible.

The term "alkylaryl" refers to an alkyl group having the number of carbon atoms designated, appended to one, two, or three aryl groups.

The term "alkoxy" as used herein refers to an alkyl, alkenyl, alkynyl, or hydrocarbon chain linked to an oxygen atom and having the number of carbon atoms specified, or if no number is specified, having up to 12 carbon atoms. Examples of alkoxy groups include, but are not limited to, groups such as methoxy, ethoxy, and t-butoxy.

The term "alkanoate" as used herein refers to an ionized carboxylic acid group, such as acetate (CH$_3$C(═O)—O$^{(-1)}$), propionate (CH$_3$CH$_2$C(═O)—O$^{(-1)}$), and the like. "Alkyl alkanoate" refers to a carboxylic acid esterified with an alkoxy group, such as ethyl acetate (CH$_3$C(═O)—O—CH$_2$CH$_3$). "ω-haloalkyl alkanoate" refers to an alkyl alkanoate bearing a halogen atom on the alkanoate carbon atom furthest from the carboxyl group; thus, ethyl ω-bromo propionate refers to ethyl 3-bromopropionate, methyl ω-chloro n-butanoate refers to methyl 4-chloro n-butanoate, etc.

The terms "halo" and "halogen" as used herein refer to Cl, Br, F or I substituents.

When "M$^+$" is used to indicate "one equivalent of a cation," it is intended to represent one equivalent of any cation, regardless of the formal charge or chemical nature of the cation. That is, M$^+$ can represent not only a singly charged cation such as Li$^+$, Na$^+$, or K$^+$, but also a multiply charged cation such as Ca$^{+2}$, Mg$^{+2}$ or Fe$^{+3}$, in an appropriate equivalent amount to the anion. M$^+$ can represent either metal or nonmetal cations; examples of nonmetal cations include, but are not limited to, NH$_3^+$ or a multiply-charged cation in an appropriate equivalent amount.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis*, 2nd Ed. (John Wiley & Sons, Inc., New York). Amino protecting groups include, but are not limited to, mesitylenesulfonyl (Mes), benzyloxycarbonyl (CBz or Z), t-butyloxycarbonyl (Boc), t-butyldimethylsilyl (TBDIMS or TBDMS), 9-fluorenylmethyloxycarbonyl (Fmoc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Hydroxyl protecting groups include, but are not limited to, Fmoc, TBDIMS, photolabile protecting groups (such as nitroveratryl oxymethyl ether (Nvom)), Mom (methoxy methyl ether), and Mem (methoxy ethoxy methyl ether), NPEOC (4-nitrophenethyloxycarbonyl) and NPEOM (4-nitrophenethyloxymethyloxycarbonyl).

Conjugates of the Invention

In one embodiment, the invention embraces conjugates of a transporter molecule linked to a cargo molecule via a releasable linker. Each of these various components is discussed further.

Transporter Molecule

Transporter molecules are molecules which enable another molecule, called the cargo molecule, to pass across a biological barrier (such as a cell membrane), or which modulate or enhance the ability of the cargo molecule to pass across a biological barrier. That is, the cargo molecule, by itself, would either not cross the barrier, or would cross the barrier in sub-optimal amounts or at a sub-optimal rate; conjugation of the cargo to the transporter enables or enhances the amount of the cargo (in conjugation with the transporter) that crosses the barrier, or modulates the rate at which the cargo (in conjugation with the transporter) crosses the barrier. Note that such modulation can be an increase in the amount of cargo transported by the conjugate as compared to the unconjugated cargo; an increase in the rate at which the cargo is transported by the conjugate as compared to the unconjugated cargo; a decrease in the amount of cargo transported by the conjugate as compared to the unconjugated cargo; or a decrease in the rate at which the cargo is transported by the conjugate as compared to the unconjugated cargo.

Numerous examples exist of appropriate transporter molecules, and the following patent publications describe molecules which can be used as transporter molecules in the current invention. U.S. Pat. No. 6,306,993 (at column 6, line 63 to column 9, line 47) and U.S. Pat. No. 6,495,663 (column 6, line 62 to column 10, line 59) and U.S. Patent Application Publications Nos. 2002/0131965, and U.S. 2003/0162719 describe compositions and methods for enhancing transport of selected compounds across a biological barrier such as a biological membrane, wherein a biological membrane is contacted with a conjugate containing a biologically active molecule that is covalently attached to a transport polymer (where the transport polymer is acting as the transport molecule). In one embodiment, the polymer consists of from 6 to 25 subunits, at least 50% of which contain a guanidino or amidino sidechain moiety. U.S. Pat. No. 6,593,292 describes additional transporter molecules, containing guanidino or amidino moieties; see column 10, line 40 to column 14, line 64. U.S. Pat. No. 6,669,951 (column 11, line 35 to column 18, line 36), U.S. Pat. No. 6,730,293 (column 10, line 1 to column 15, line 36), and U.S. Pat. No. 6,759,387 (column 10, line 44 to column 16, line 26) describe transporters containing guanidino or amidino molecules, such as arginine amino acids, useful for transporting molecules across epithelial and endothelial tissues. The cited patents, patent publications, and specific sections referred to above are hereby incorporated by reference herein in their entirety.

Lipids can also be used as transporter molecules for various compounds. Lipids include, but are not limited to, fatty acids of the form ($C_7$-$C_{32}$ hydrocarbyl)-C(=O)—OH and acyl forms thereof, with ($C_7$-$C_{32}$ alkyl)-C(=O)—OH and ($C_7$-$C_{32}$ alkenyl)-C(=O)—OH and their acyl forms as preferred subsets. Caprylic acid (octanoic acid), capric acid (decanoic acid), lauric acid (dodecanoic acid), myristic acid (tetradecanoic acid), palmitic acid (hexadecanoic acid), stearic acid (octadecanoic acid), arachidic acid (icosanoic acid), behenic acid (docosanoic acid), palmitoleic acid, oleic acid, linoleic acid, linolenic acid, arachidonic acid, eicosapentaenoic acid, docosahexaenoic acid, and erucic acid are examples of lipids which can be used as the transporter moiety. Example 10 below indicates one embodiment for linking lipids to cargo using the linkers of the invention.

In addition to the above known transporter molecules, which can be used with the releasable linker embodiments disclosed herein, new transporters can be evaluated using the releasable linker embodiments. A transporter is attached to the linker in conjugation with a reporter molecule, e.g., luciferin, and the efficacy of the transporter molecule in transporting the reporter molecule across a biological barrier can be readily measured.

In one embodiment, the conjugate incorporates a transporter molecule bearing a thiol group of the form Transp-SH. Transporters lacking a thiol group can be derivatized to incorporate a thiol group; for example, compounds such as Trityl-S—$CH_2CH_2$COOH and Trityl-S—$CH_2CH_2NH_2$ can be used to derivatize amino-containing and carboxylate-containing compounds, respectively, in order to incorporate a thiol group. For peptidic transporters, a naturally-occurring cysteine residue may already be present in the polypeptide, or, for synthetic peptides, incorporation of a cysteine residue or analog (such as homocysteine) is readily accomplished during peptide synthesis. Other methods of incorporating thiol groups into polypeptides are found in Wong, Chemistry of Protein Conjugation and Cross-Linking, CRC Press: Boca Raton, 1991; several of these methods are applicable to non-peptidic transporters as well.

In one embodiment, the invention embraces a method of testing, or assaying, various transporter agents for efficacy of transport. A reporter molecule can be conjugated to a transporter molecule via a releasable linker. A biological barrier (such as a cell membrane) is contacted with the conjugate; see Example 6 below for an illustration of one such assay. The total amount of reporter molecule transported can be readily quantitated for a given transporter. Repeated assays with different transporter molecules, using the same reporter molecule, provides a method for determining the efficacy of transport of a given transporter molecule.

Cargo Molecule

A variety of molecules can be used as the cargo component of the conjugate. Biologically active molecules are one group of compounds that can be used as cargo. Biologically active molecules (which encompass drugs, therapeutic agents, and diagnostic agents) include, but are not limited to, metal ions (which are typically delivered as metal chelates); small organic molecules, such as anticancer molecules (e.g., doxorubicin, bleomycin, dactinomycin, daunorubicin, epirubicin, idarubicin, mitoxantrone, mitomycin, epipodophyllotoxins, etoposide, teniposide, antimicrotubule agents, vinblastine, vincristine, vindesine, vinorelbine, other vinca alkaloids, taxanes, paclitaxel (taxol), docetaxel (taxotere), other taxoids, nitrogen mustards, chlorambucil, cyclophosphamide, estramustine, ifosfamide, mechlorethamine, melphalan, aziridines, thiotepa, alkyl sulfonates, busulfan, nitrosoureas, carmustine, lomustine, streptozocin, platinum complexes, carboplatin cisplatin, alkylators, altretamine, dacarbazine, procarbazine, temozolamide, folate analogs, methotrexate, purine analogs, fludarabine, mercaptopurine, thioguanine; adenosine analogs, cladribine, pentostatin, pyrimidine analogs, capecitabine, cytarabine, floxuridine, fluorouracil, 5-fluorouracil, gemcitabine, substituted ureas, hydroxyurea, camptothecin analogs, irinotecan, topotecan, topoisomerase I inhibitors, topoisomerase II inhibitors, and anthracycline antibiotics); antibiotic and antimicrobial molecules (e.g., penicillin, cephalosporin, isoniazid, trimethoprim, quinolones, fluoroquinolones, macrolide antibiotics such as erythromycin and tylosin); and macromolecules such as polynucleotides and polynucleotide analogs, polypeptides (peptides and proteins) and polypeptide analogs, and polysaccharides and polysaccharide analogs. Examples of macromolecules include, but are not limited to, small interfering RNAs (siRNA or RNAi), short hairpin RNA (shRNA), ribozymes (which optionally contains one or more 2'-deoxy nucleotide subunits for enhanced stability), peptide nucleic acids (PNA), protein antigens such as tumor antigens, and peptides such as the cyclosporins. Polynucleotide analogs and polypeptide analogs may have modified backbones to impart one or more desirable properties, such as increased resistance to degradation or altered water solubility. The biologically active molecule preferably has a molecular weight less than about 10 kDa, more preferably less than about 1 kDa, still more preferably less than about 600 Daltons. Suitable cargo molecules are discussed in more detail herein.

A. Small Organic Molecules

A variety of small organic molecules can be attached to the conjugate as cargo. The small organic molecule need only have a nucleophilic moiety to serve as the -Nu portion of the cargo. Often small organic molecules will already have suitable nucleophilic moieties, some small organic molecules may have multiple nucleophilic moieties (in which case protection of certain nucleophilic moieties may be desirable in order to limit attachment of the linker to the small organic molecule at one defined site), and other small organic molecules can be readily derivatized to contain a nucleophilic moiety. For example, doxorubicin,

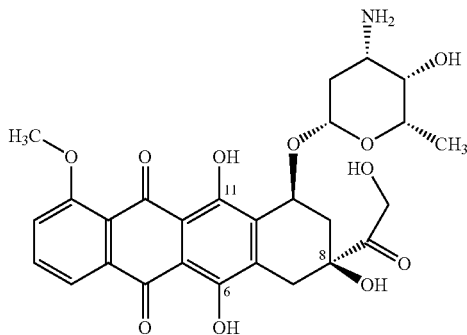 [SMILES: COc1cccc2c1C(=O)c1c(O)c3c(c(O)c1C2=O)C[C@@](O)(C(=O)CO)C[C@@H]3O[C@@H]1C[C@H](N)[C@H](O)[C@H](C)O1]

can be attached to the linker by any of its —OH groups (such as the 6-hydroxy or 11-hydroxy groups, the 8-hydroxy group or the hydroxy group of the (8-hydroxyacetyl) moiety, the hydroxy group vicinal to the —$NH_2$ group, or the —$NH_2$ group itself, any of which can serve as the -NuH moiety of the Cargo-NuH group.

Figure 6:
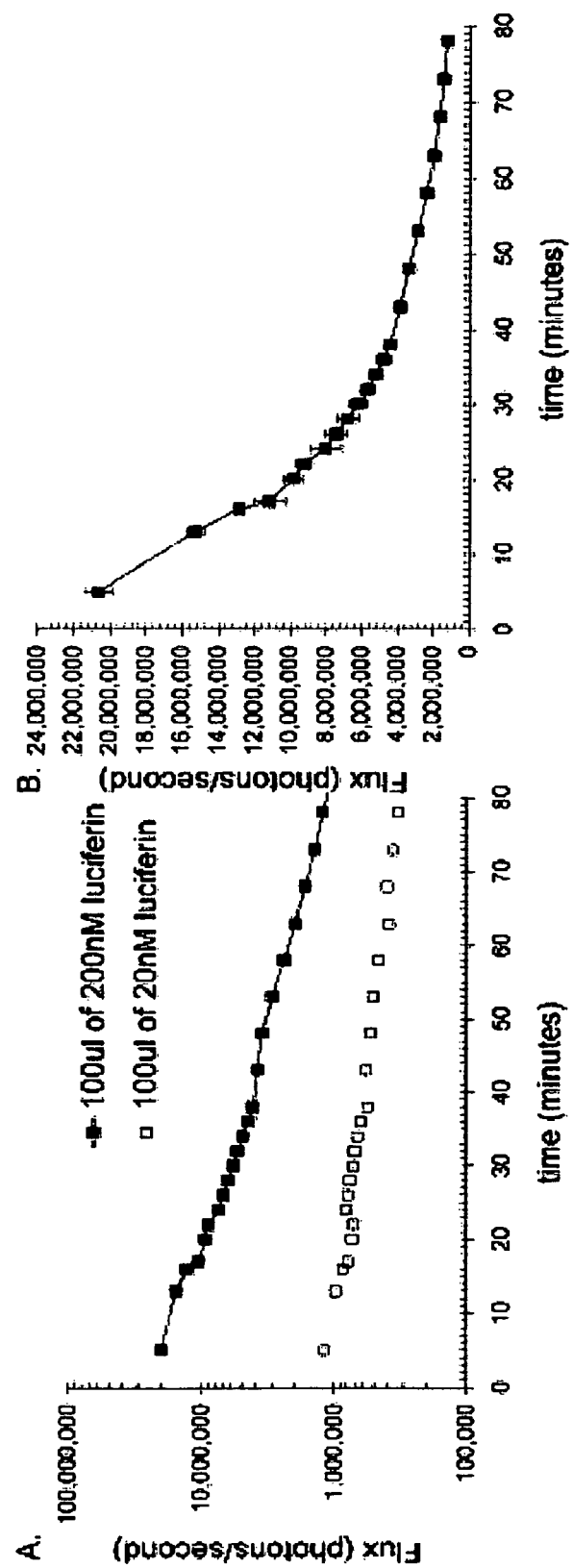
FIG. 6 depicts the resultant bioluminescence after intradermal injection of luciferin in HBS pH 7.4 into transgenic (FVB-luc+) mice. Approximately ten times the amount of light was observed when the luciferase expressing mice were injected with 200 vs. 20 nM luciferin; see FIG. 6A. The area under the curve for 200 nM was $3.02 \times 10^{10}$ photons, while that for 20 nM was $3.11 \times 10^9$ photons (10.24%). When plotted linearly, the bioluminescence rapidly decreases for the first thirty minutes; see FIG. 6B. The plot is the average of three injections in separate animals.

Taxane and taxoid anticancer molecules can also be used as cargo molecules in the conjugates. Such conjugates are useful as anticancer agents. The term "taxanes" refers to paclitaxel (also known as TAXOL, a registered trademark of Bristol-Myers Squibb Co., New York, N.Y.) (see FIG. 6F of U.S. Pat. No. 6,306,993, and the structure immediately following, where R'=acetyl and R"=benzoyl) and naturally occurring, synthetic, or bioengineered analogs having a backbone core that contains the A, B, C and D rings of paclitaxel, as illustrated in FIG. 6G of U.S. Pat. No. 6,306,993. FIG. 6F of U.S. Pat. No. 6,306,993 also indicates the structure of TAXOTERE (a registered trademark of Aventis Pharma, France) (R'=H, R"=t-butyloxycarbonyl (i.e., Boc)), which is a somewhat more soluble synthetic analog of paclitaxel. "Taxoid" refers to naturally occurring, synthetic or bioengineered analogs of paclitaxel that contain the basic A, B and C rings of paclitaxel, as shown in FIG. 6H of U.S. Pat. No. 6,306,993 and described therein at column 16, lines 9 to 26. A wide array of information about taxanes and taxoids, including chemical, synthetic, and biological methods and cell lines for assaying anticancer activity, is presented in Taxol: Science and Applications, Suffness, M., Ed., CRC Press, New York N.Y. (1995).

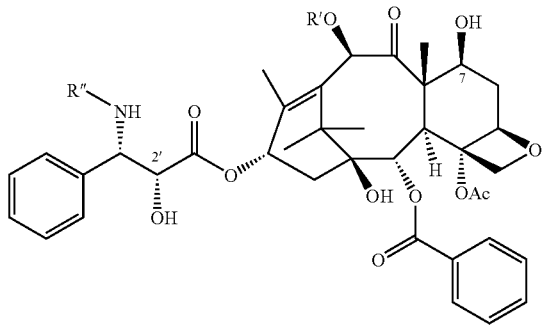

Either the C2' hydroxyl oxygen or the C7 hydroxyl oxygen of paclitaxel and its derivatives can serve as the -Nu portion of the cargo molecule. As C2' conjugation can reduce anticancer activity, the releasable linkers provided in one embodiment of the invention are highly advantageous in that they are completely cleaved from the cargo after transport across a biological barrier occurs. The amide nitrogen can also be used as the -Nu portion of the cargo molecule if desired. Alternatively, other synthetic methods, such as those described in U.S. Pat. No. 6,306,993, Example 9 or columns 15-16, can be used. Examples of conjugates of paclitaxel (TAXOL) using the conjugates of the current invention are described in Example 8.

B. Metal Ions

Metal ions can be transported as chelates. For example, metals can be chelated by diethylenetriaminepentaacetic acid, DTPA, which can then be further derivatized, e.g. by coupling of Boc-NH—$CH_2CH_2$—$NH_2$ to a free carboxyl using carbodiimides or uronium reagents such as HATU, HBTU and TBTU followed by removal of the Boc group; the free nitrogen of the metal-DTPA-NH—$CH_2CH_2$—$NH_2$ complex can serve as the -NuH group. Alternatively, metals can be complexed to porphyrins or tetrapyrrole derivatives such as phthalocyanines or texaphyrins containing a free amino group, e.g., the carboxylic acid groups of mesoporphyrin IX can be derivatized with Boc-NH—$CH_2CH_2$—$NH_2$ as described above for DTPA for subsequent conjugation to the releasable linker. Iron, magnesium, zinc, copper (e.g., Cu67), nickel, cobalt (e.g., Co57), europium, technetium (e.g., Tc99m), europium, lutetium, yttrium (e.g., Y90), praseodymium, gadolinium, gallium (e.g., Ga67), or indium (e.g., In111). In various embodiments, the metal can be a divalent metal ion, such as $Ca^{+2}$, $Mn^{+2}$, $Co^{+2}$, $Ni^{+2}$, $Zn^{+2}$, $Cd^{+2}$, $Hg^{+2}$, $Sm^{+2}$ and $UO_2^{+2}$, or a trivalent metal ion, such as $Mn^{+3}$, $Co^{+3}$, $Ni^{+3}$, $Y^3$, $In^{+3}$, $Pr^{+3}$, $Nd^{+3}$, $Sm^{+3}$, $Fe^{+3}$, $Ho^{+3}$, $Ce^{+3}$, $Eu^{+3}$, $Gd^{+3}$, $Tb^{+3}$, $Dy^{+3}$, $Er^{+3}$, $Tm^{+3}$, $Yb^{+3}$, $Lu^{+3}$, $La^{+3}$ and $U^{+3}$.

C. Macromolecules

Macromolecules can also be transported as cargo in the conjugates. Macromolecules include, but are not limited to, proteins, plasmids, and oligosaccharides, including, but not limited to, polynucleotides and polynucleotide analogs, polypeptides (peptides and proteins) and polypeptide analogs (such as peptoids), and polysaccharides and polysaccharide analogs. Examples of polynucleotides and polynucleotide analogs include DNA, cDNA, in vitro polymerized DNA, plasmid DNA, fragments of plasmid DNA, linear DNA, vectors (P1, PAC, BAC, YAC, artificial chromosomes), recombinant DNA, chromosomal DNA, anti-sense DNA, or derivatives of these DNAs; small interfering RNAs (siRNA or RNAi), tRNA (transfer RNA), snRNA (small nuclear RNA), rRNA (ribosomal RNA), mRNA (messenger RNA), ribozymes (which optionally contains one or more 2'-deoxy nucleotide subunits for enhanced stability), and peptide nucleic acids (PNA). Examples of polypeptides and polypeptide analogs include peptide hormones, peptoids, antibodies, monoclonal antibodies, single chain antibodies (scAb), antibody fragments such as Fv, Fc, F(ab')$_2$, and Fab, single-chain variable region fragments (scFv), enzymes, toxins, and protein antigens such as tumor antigens. Polynucleotide analogs and polypeptide analogs may have modified backbones to impart one or more desirable properties, such as increased resistance to degradation or altered water solubility. Analogs may include charged and preferably uncharged backbone analogs, such as phosphonates (preferably methyl phosphonates), phosphoramidates, thiophosphates, uncharged morpholino-based polymers, 2'-O-methyl polynucleotides, and peptide nucleic acids (PNAs). PNAs are analogs of DNA in which the backbone, comprised of N-(2-aminoethyl)glycine units, is structurally analogous to the deoxyribophosphate backbone of DNA; the units can bear any of the bases that naturally occur in polynucleotides. Polypeptides have a variety of nucleophiles that can serve as the -Nu moiety of the cargo. Alternatively, derivatization of peptides and proteins to introduce a nucleophile is straightforward; see Wong, Chemistry of Protein Conjugation and Cross-Linking, CRC Press: Boca Raton, 1991.

One type of nucleic acid of interest is the class of small interfering RNAs (or short interfering RNAs, siRNA) which results in RNA interference (RNAi). RNA interference has been the subject of intense research because of its potential for sequence-specific silencing of genes of interest, such as HIV or hepatitis viral genes in an infected patient. See Hannon et al., Nature 431:371 (2004) and Grunweller et al., Curr. Med. Chem. 12:3143 (2005). MicroRNA (miRNA) is another type of RNA that can be used in gene regulation; see Yeung et al., Cell Res. 15:935 (2005) and Du et al., Development 132:4645 (2005). Short hairpin RNA (shRNA) can also be used for gene regulation; see Pekarik, Brain Res. Bull. 68:115-20 (2005).

siRNA, miRNA, and shRNA, as well as other nucleic acids, can be readily incorporated into conjugates with a releasable linker. Either the 5'-hydroxyl or the 3'-hydroxyl of a nucleic acid can serve as the -NuH moiety of the nucleic acid cargo molecule. Alternatively, nucleophiles can readily be introduced onto nucleic acids using methods readily known in the art; see, for example, U.S. Pat. Nos. 5,594,118, 5,843,650, 6,537,783, and 6,699,978.

The cyclosporins are another group of macromolecules suitable for use as cargo. The cyclosporins are cyclic peptides that display immunosuppresant activity. Cyclosporin A (Chemical Abstracts REGISTRY number 59865-13-3; cyclo [L-alanyl-D-alanyl-N-methyl-L-leucyl-N-methyl-L-leucyl-N-methyl-L-valyl-(3R,4R,6E)-6,7-didehydro-3-hydroxy-N,4-dimethyl-L-2-aminooctanoyl-L-2-aminobutanoyl-N-methylglycyl-N-methyl-L-leucyl-L-valyl-N-methyl-L-leucyl]) is used clinically to suppress organ rejection after transplantation. The 3-hydroxy group on the 2-aminooctanoyl subunit provides a convenient site for attaching the linker group of the invention, serving as the "Nu" unit of the cargo attachment in the conjugate. Other cyclosporins, such as cyclosporin B, cyclosporin C, cyclosporin D, cyclosporin G, cyclosporin H, and cyclosporin M (see, e.g., U.S. Pat. Nos. 6,007,840 and 6,004,973), can also be conjugated at the 3-hydroxy group; appropriate protection of the threonine hydroxyl of cyclosporin C is employed to prevent derivatization at that site (or, alternatively, appropriate protection of the 3-hydroxy group of the 2-aminooctanoyl moiety is provided, and the conjugate is formed at the threonine hydroxyl of cyclosporin C).

If a different "Nu" group is desired, it can be introduced by, for example, creating the chloroacetate ester of the 3-hydroxy group (the chloroacetate ester of cyclosporine A has Chemical Abstracts REGISTRY number 141749-42-0; see U.S. Pat. No. 6,730,293, FIG. 1, and Example 5.A.1. for preparation of the alpha-chloroacetyl cyclosporin A), and reacting the chloroacetyl group further to introduce the desired group. Other cyclosporins, such as cyclosporin B, cyclosporin C, cyclosporin D, cyclosporin G, and cyclosporin H can also be derivatized as chloroacetate esters for conjugation; appropriate protection of the threonine hydroxyl of cyclosporin C is employed to prevent reaction of chloroacetyl anhydride at that site (or, alternatively, appropriate protection of the 3-hydroxy group of the 2-aminooctanoyl moiety is provided, and the chloroacetyl ester is formed at the threonine hydroxyl of cyclosporin C). The chlorine of the chloroacetyl group can then be displaced with the desired nucleophile-bearing group.

Example 5.A.1. of U.S. Pat. No. 6,730,293 can be modified by employing the symmetric anhydride of Boc-glycine, or an active ester of Boc-glycine, in place of choroacetyl anhydride. Other protected glycine derivatives can also be used. After coupling of the protected glycine to the 3-hydroxy group of the 2-aminooctanoyl subunit of cyclosporin, deprotection of the amino group of the glycine yields a nitrogen nucleophile suitable for use as the "Nu" group in the conjugates of the invention.

Alternatively, derivatives of cyclosporine with groups introduced for conjugation can be used; see, e.g., U.S. Pat. No. 6,207,398.

D. Polyamines

Another type of molecule which can be used as cargo is a polyamine or polyamine analog. Polyamines are naturally occurring molecules having two or more amino groups connected by alkyl chains of varying length. Polyamine analogs are non-naturally occurring molecules having two or more amino groups, where one or more of the alkyl chains have been replaced with a non-naturally occurring component, such as a conformationally restricted hydrocarbyl unit, to produce a conformationally restricted polyamine. By "conformationally restricted" is meant that, in a polyamine analog, at least two amino groups in the molecule are locked or limited in spatial configuration relative to each other. The amino groups within the molecule may be primary, secondary, tertiary, or quarternary, and are preferably primary or secondary amino groups, more preferably secondary amino groups. The relative movement of two amino groups can be restricted, for example, by incorporation of a cyclic or unsaturated moiety between them (exemplified, but not limited to, a ring, such as a three-carbon ring, four-carbon ring, five-carbon-ring, six-carbon ring, or a double or triple bond, such as a double or triple carbon bond). Groups restricting conformational flexibility by means of steric hindrance, yet favorable to the therapeutic effects of the compound, can also be used. A conformationally restricted polyamine analog can comprise at least two amino groups which are conformationally restricted relative to each other; a polyamine analog can also further comprise amino groups which are not conformationally restricted relative to other amino groups. Conformationally restricted polyamine analogs include, but are not limited to, the compounds disclosed in International Patent Application WO 98/17624, U.S. Pat. No. 5,889,061, and U.S. Pat. No. 6,392,098; the compounds disclosed in WO 00/66587 and U.S. Pat. No. 6,794,545; and the compounds disclosed in United States Patent Application Publication Nos. 2003/0072715, 2003/0195377, and International Patent Applications WO 02/10142, and WO 03/050072. Other polyamines which can be used are those described in U.S. Patent Application Publication No. 2003/0130356, which disclosed saturated long-chain polyamines (referred to in that document as "oligoamines"). All compound disclosed in the foregoing references, including but not limited to the specification, claims, tables, examples, figures, and schemes of that patent, are expressly incorporated by reference herein The various amino groups in the polyamines can serve as the -NuH moiety of the cargo molecule. To restrict conjugation to a single site on the polyamine, differential protection of the amino groups on the polyamine compound can be used in order to prevent reaction at undesired sites.

Examples of polyamine compounds useful in the invention are depicted in Table 1. While some of the compounds are depicted as salts, such as the hydrochloride salt, it is to be understood that the disclosure in the table embraces all salts, hydrates, and solvates of the compounds depicted therein, as well as the non-salt, non-hydrate/non-solvate form of the compound, as is well understood by the skilled artisan. Table 1 includes both non-conformationally restricted polyamine analogs (oligoamines) and conformationally restricted polyamine analogs.

TABLE 1

| Compound | Structure |
|---|---|
| CGC-11027 | 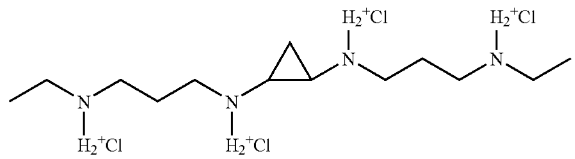 |
| CGC-11028 | 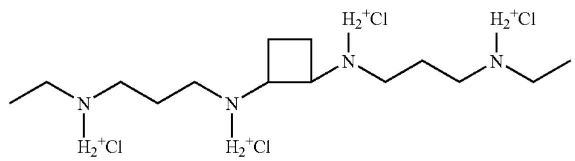 |
| CGC-11029 | 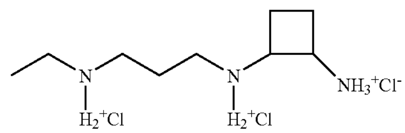 |
| CGC-11033 | 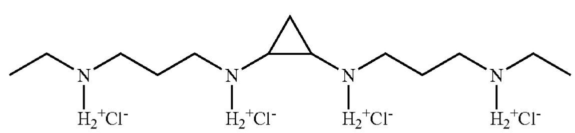 |
| CGC-11034 | 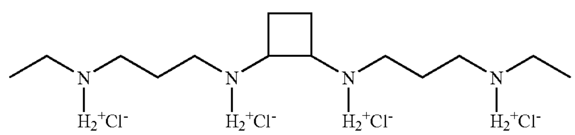 |
| CGC-11035 | 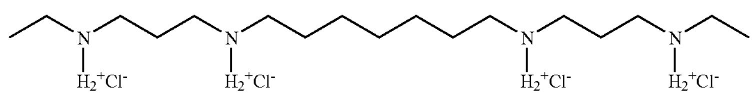 |
| CGC-11036 | 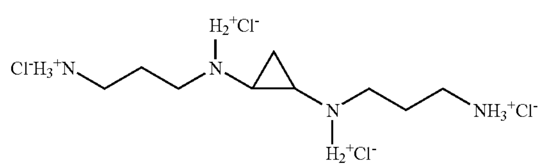 |
| CGC-11037 | 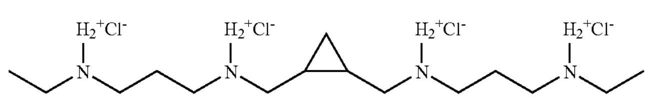 |
| CGC-11038 | 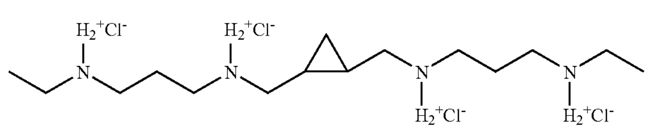 |
| CGC-11043 | 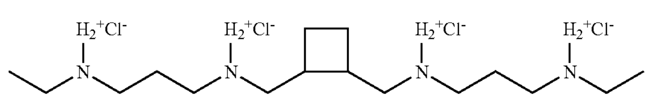 |
| CGC-11044 | 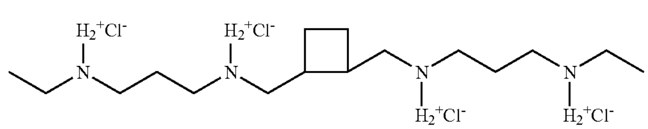 |

TABLE 1-continued

| Compound | Structure |
|---|---|
| CGC-11047 | (structure: EtNH-(CH₂)₃-NH-CH₂-CH=CH-CH₂-NH-(CH₂)₃-NHEt, cis alkene, ·4H⁺Cl⁻) |
| CGC-11048 | (structure: EtNH-(CH₂)₃-NH-CH₂-CH=CH-CH₂-NH-(CH₂)₃-NHEt, trans alkene, ·4H⁺Cl⁻) |
| CGC-11050 | BnNH(CH₂)₄NHBn |
| CGC-11061 | EtNH(CH₂)₄NH(CH₂)₄NH(CH₂)₄—NHEt•5HCl |
| CGC-11093 | (structure: EtNH-(CH₂)₄-NH-CH₂-cyclopropyl-CH₂-NH-(CH₂)₄-NHEt) |
| CGC-11094 | (structure: EtNH-(CH₂)₃-NH-CH₂-(1,2-phenylene)-CH₂-NH-(CH₂)₃-NHEt •4HCl) |
| CGC-11098 | (structure: EtNH-(CH₂)₄-NH-CH₂-cyclopropyl-CH₂-NH-(CH₂)₄-NHEt •4HCl) |
| CGC-11099 | (structure: EtNH-(CH₂)₄-NH-CH₂-cyclobutyl(cis)-CH₂-NH-(CH₂)₄-NHEt •4HCl) |
| CGC-11100 | (structure: EtNH-(CH₂)₄-NH-CH₂-cyclobutyl(trans)-CH₂-NH-(CH₂)₄-NHEt •4HCl) |
| CGC-11101 | (structure: EtNH-(CH₂)₄-NH-CH₂-CH=CH-CH₂-NH-(CH₂)₄-NHEt •4HCl) |
| CGC-11102 | (structure: EtNH-(CH₂)₄-NH-CH₂-CH=CH-CH₂-NH-(CH₂)₄-NHEt, cis •4HCl) |
| CGC-11103 | (structure: EtNH-(CH₂)₄-NH-CH₂-C≡C-CH₂-NH-(CH₂)₄-NHEt •4HCl) |
| CGC-11104 | (structure: EtNH-(CH₂)₄-NH-CH₂-(1,2-phenylene)-CH₂-NH-(CH₂)₄-NHEt •4HCl) |
| CGC-11105 | (structure: EtNH-(CH₂)₃-NH-cyclopentyl-CH₂-NH-(CH₂)₃-NHEt •4HCl) |
| CGC-11108 | (structure: EtNH-CH₂-CH=CH-CH₂-NH-CH₂-CH=CH-CH₂-NH-CH₂-CH=CH-CH₂-NHEt •4HCl) |

TABLE 1-continued
| Compound | Structure |
|---|---|
| CGC-11114 | 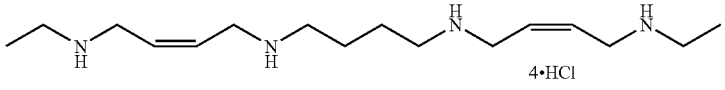 4·HCl |
| CGC-11119 | 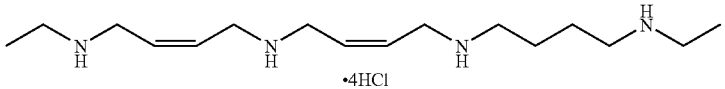 [SMILES: CCNC/C=C\CNC/C=C\CNCCCCNCC ; "·4HCl"] ·4HCl |
| CGC-11090 | 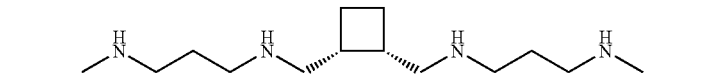 |
| CGC-11091 | 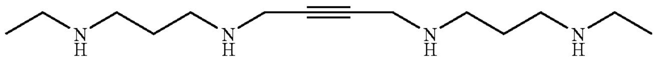 [SMILES: CCNCCCNCC#CCNCCCNCC] |
| CGC-11092 | 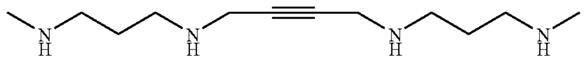 |
| CGC-11101 | 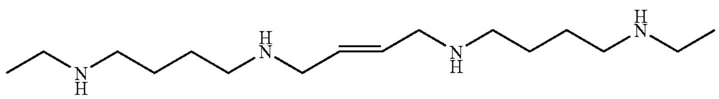 [SMILES: CCNCCCCNC/C=C/CNCCCCNCC] |
| CGC-11103 | 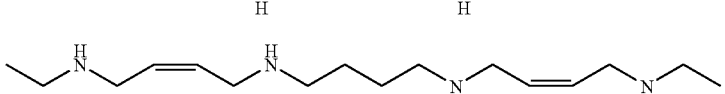 |
| CGC-11114 | 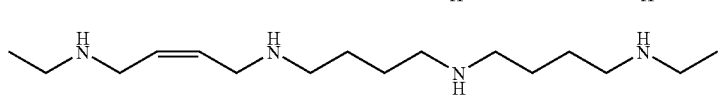 |
| CGC-11118 | 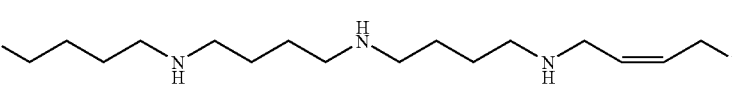 |
| CGC-11121 | 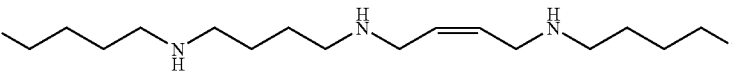 |
| CGC-11122 | 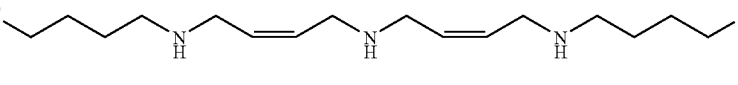 |
| CGC-11123 | 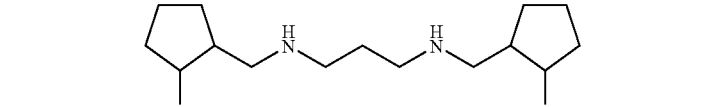 |
| CGC-11124 | 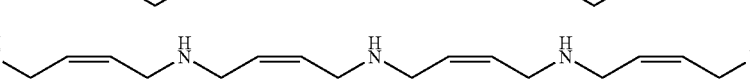 |
| CGC-11126 | 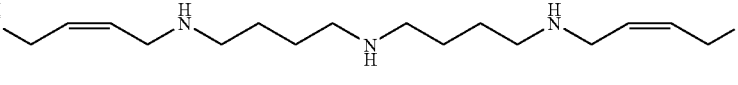 |
| CGC-11128 | 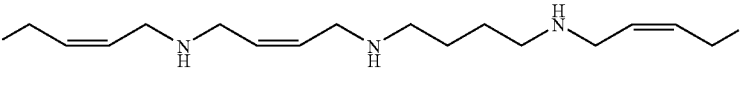 |
| CGC-11129 | 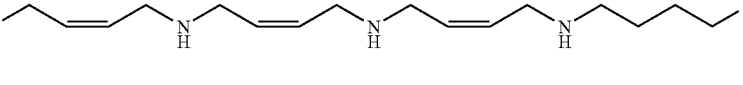 |
| CGC-11130 | 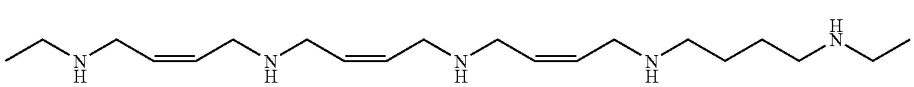 [SMILES: CCNC/C=C\CNC/C=C\CNC/C=C\CNCCCCNCC] |

TABLE 1-continued

| Compound | Structure |
|---|---|
| CGC-11132 | 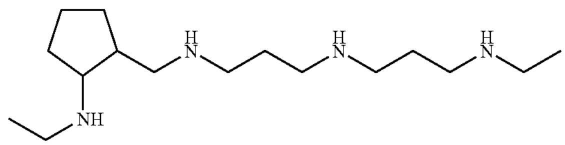 [SMILES: CCNCCCNCCCNCC1CCCC1NCC] |
| CGC-11133 | 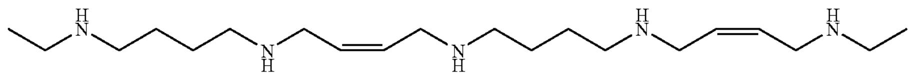 |
| CGC-11134 | 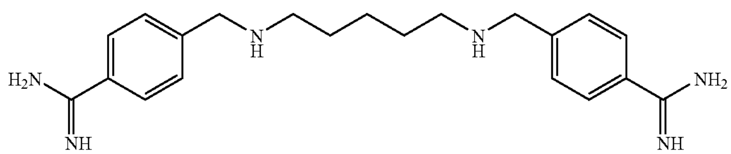 [SMILES: N=C(N)c1ccc(CNCCCCCNCc2ccc(C(=N)N)cc2)cc1] |
| CGC-11135 | 5·HCl |
| CGC-11136 | 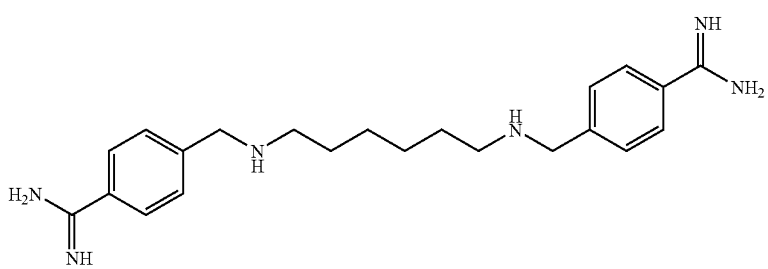 [SMILES: N=C(N)c1ccc(CNCCCCCCNCc2ccc(C(=N)N)cc2)cc1] |
| CGC-11137 | 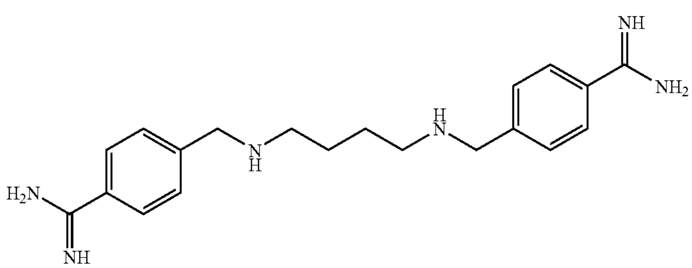 [SMILES: N=C(N)c1ccc(CNCCCCNCc2ccc(C(=N)N)cc2)cc1] |
| CGC-11141 | 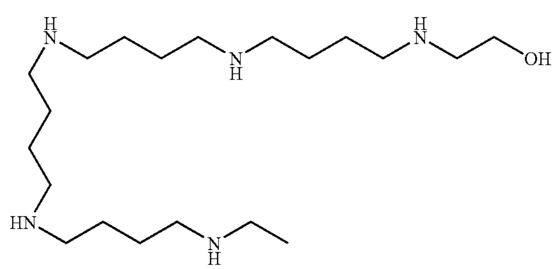 [SMILES: CCNCCCCNCCCCNCCCCNCCCCNCCO] |
| CGC-11143 | 5·HCl |

TABLE 1-continued

| Compound | Structure |
|---|---|
| CGC-11144 | 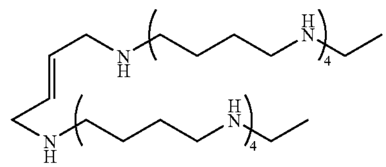 |
| CGC-11150 | 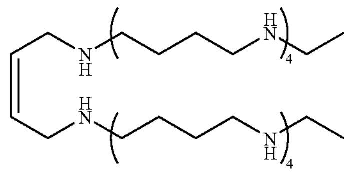 |
| CGC-11155 | 6·HCl |
| CGC-11157 | 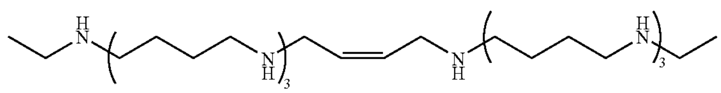 |
| CGC-11158 | 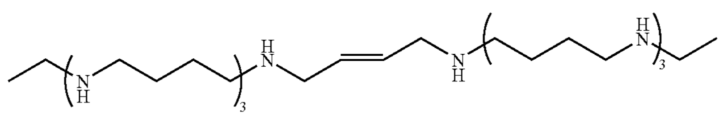 |
| CGC-11201 | 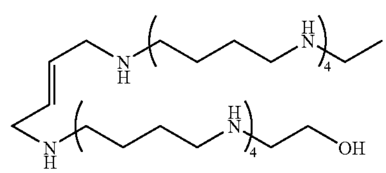 |
| CGC-11202 | 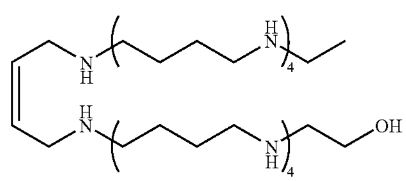 |
| CGC-11174 | ·3HCl |
| CGC-11197 | ·3HCl |

TABLE 1-continued
| Compound | Structure |
|---|---|
| CGC-11199 | 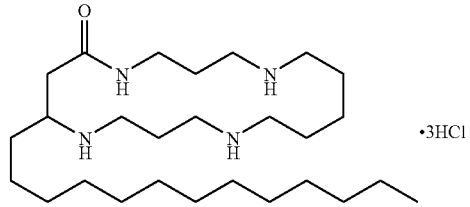 [SMILES: CCCCCCCCCCCCCC1CC(=O)NCCCNCCCCCNCCCN1 ; "·3HCl"] ·3HCl |
| CGC-11200 | 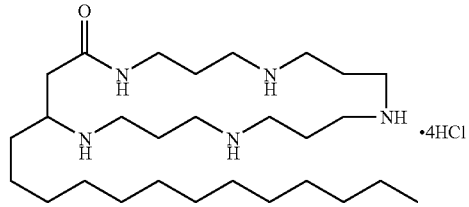 [SMILES: CCCCCCCCCCCCCC1CC(=O)NCCCNCCCNCCCNCCCN1 ; "·4HCl"] ·4HCl |
| CGC-11208 | 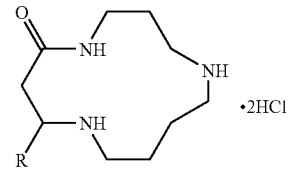 ·2HCl<br>R = n-C₁₃H₂₇ |
| CGC-11238 | 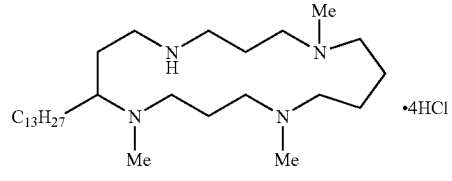 ·4HCl |
| CGC-11239 | 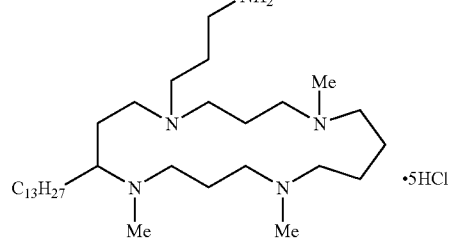 ·5HCl |
| CGC-11159 | 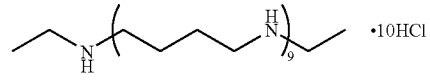 ·10HCl |
| CGC-11160 | 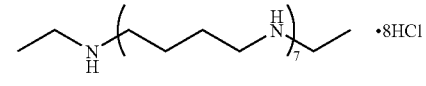 ·8HCl |
| CGC-11175 | 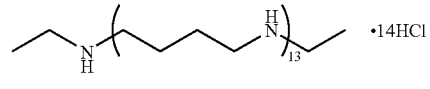 ·14HCl |
| CGC-11226 | 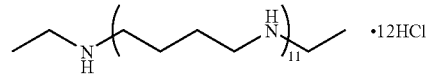 ·12HCl |

E. Reporter Molecules

Another type of molecule which can be used as cargo is a reporter molecule. Reporter molecules are molecules which can be readily detected for quantitative or qualitative analysis. Examples of reporter molecules include, but are not limited to, radioactive molecules, fluorescent molecules (e.g., rhodamines, coumarins, cyanines, fluoresceins, xanthene dyes (e.g., 4-(2,7-difluoro-6-hydroxy-3-oxo-xanthen-9-yl) benzene-1,3-dicarboxylic acid, known as OREGON GREEN, a trademark of Molecular Probes, Inc., Oregon), pyrenes, lanthanide chelates), phosphorescent molecules (e.g., metalloporphyrins, eosin, erythrosin), heavy atoms (typically chelated to an organic carrier), chemiluminescent molecules, bioluminescent molecules (e.g., luciferin, which is detected in cells, tissues or animals when converted by luciferase to light and byproduct), biotinylated molecules which can be recognized by a labeled avidin or labeled streptavidin (where the labeled avidin or streptavidin is detected), antigenic molecules which can be recognized by a labeled antibody (where the labeled antibody is detected), and metal ions such as those described above, which can be used as diagnostic agents, imaging agents, and detection agents.

As with other cargo molecules, reporter molecules can be attached to the linker by utilizing a nucleophilic moiety on the reporter molecule. Thus, for luciferin,

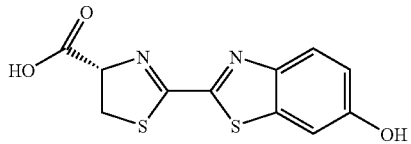 [SMILES: O=C(O)[C@H]1CSC(c2nc3ccc(O)cc3s2)=N1]

the phenolic oxygen on the benzo[d]thiazole ring can be deprotonated (for example, a salt of the compound, e.g. the potassium salt, can be dissolved in aqueous base) and used as the nucleophilic moiety -Nu(-) of the Carg-Nu(-) component. Other compounds can also be attached via suitable nucleophilic groups; e.g., Rhodamine 110 can be attached via its aromatic —NH$_2$ group.

Detection of the reporter molecule can be carried out by various means known in the art, e.g., spectroscopic detection, detection of radioactivity, electrochemical detection, or enzyme assay. The detection threshold for the signal produced by the reporter molecule should be set at a reasonable level so as to distinguish signal from background noise, for example, a signal level of a magnitude 10%, 25%, 50%, or 100% above the standard deviation of the background noise, or a signal level with about a 66% probability, more preferably about a 95% probability, still more preferably about a 99% probability, of being due to signal rather than noise.

Releasable Linker

A variety of releasable linkers can be used in the invention. One preferred linker system is represented by the structure:

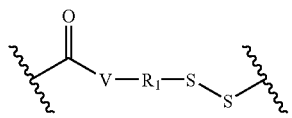

where $R_1$ is $C_1$-$C_8$ hydrocarbon, preferably $C_1$-$C_8$ alkyl, more preferably $C_1$-$C_4$ alkyl, still more preferably —CH$_2$CH$_2$—, —CH$_2$CH$_2$CH$_2$—, or —CH$_2$CH$_2$CH$_2$CH$_2$—; and V is —O—, —NH—, —NR$_2$—, —CH$_2$—, —CHR$_2$—, —C(R$_2$)$_2$—, or —S—, preferably —O—; and $R_2$ is $C_1$-$C_4$ alkyl. In a reducing environment, such as the interior of a cell, the disulfide bond of this linker system is reduced to its constituent thiols.

For illustration, where the two molecules Carg-Nu and Transp are joined by this linker:

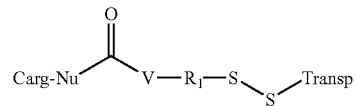

transport of the conjugate into the cell results in reduction of the disulfide bond to yield the products:

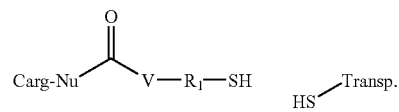

The free thiol of the Carg-Nu-(C=O)—V—R$_1$—SH product can now react intramolecularly with various components of the carbonyl system in order to liberate the free molecule Carg-Nu (as Carg-Nu(-), Carg-Nu(-)M$^+$ where M$^+$ is one equivalent of a cation, or Carg-NuH). Depending on the nature of the R$_1$ group and the groups selected as V and Nu, the free thiol may react at the carbonyl carbon to yield Carg-Nu and the cyclic product

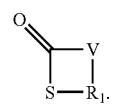

When R$_1$ is —CH$_2$CH$_2$— or —CH$_2$CH$_2$CH$_2$—, a five- or six-membered ring results, respectively, and intramolecular cyclization is relatively facile. Other hydrocarbon groups can be selected to "tune" the rate of the intramolecular reaction.

Alternatively, the free thiol may react at the carbon alpha to the V atom. For example, when a —CH$_2$— group is adjacent to the V atom, and R$_{1R}$ represents the remainder of the R$_1$ group:

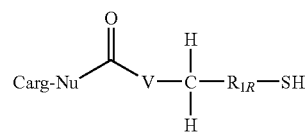

the thiol may attack the —CH$_2$— group adjacent to the V atom in an S$_N$2-type displacement reaction, yielding the products

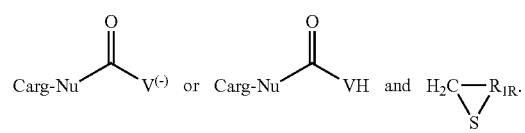

When R$_{1R}$ is —CH$_2$CH$_2$CH$_2$— or —CH$_2$CH$_2$CH$_2$CH$_2$—, a five- or six-membered ring results, respectively, and intramolecular cyclization via the S$_N$2 mechanism is relatively facile.

The product

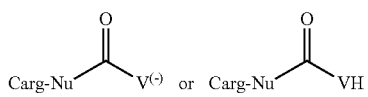

decomposes relatively rapidly to Carg-Nu(–), Carg-Nu(–)M+ where M+ is one equivalent of a cation, or Carg-NuH. For example, where Nu and V are both O,

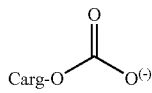

the product decarboxylates rapidly to yield Carg-Nu(–), Carg-Nu(–)M+, or Carg-NuH, with concomitant evolution of $CO_2$.

Synthesis of a conjugate of a cargo molecule, Carg-NuH, and a transporter molecule, Transp-SH, with this linker can be performed using the following general scheme.

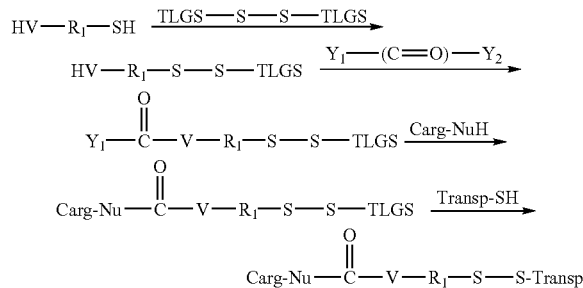

The molecule HV—$R_1$—SH is reacted with a disulfide compound which is substituted on each sulfur atom with a good thiol leaving group stabilizer (TLGS; the two TLGS groups may be the same or different) to yield HV—$R_1$—S—S-TLGS. The thiol leaving group stabilizer serves to stabilize the thiol group displaced from the disulfide. Examples of disulfide compounds which are substituted on each sulfur atom with a good thiol leaving group stabilizer are 2,2'-dipyridyl disulfide(2,2'-dithiodipyridine) and Ellman's reagent (5,5'-dithio-bis(2-nitrobenzoic acid), DTNB); other examples of such disulfide-activating reagents are known in the art. (Note that when V is —S—, it should be protected with a protecting group such as trityl or p-methoxytrityl, which can subsequently be removed by mild acid without disturbing the disulfide.) Then HV—$R_1$—S—S-TLGS is reacted with a compound of the form $Y_1$—(C═O)—$Y_2$, where $Y_1$ and $Y_2$ are good leaving groups and may be the same or different. Examples of these compounds include phosgene (Cl—(C═O)—Cl), bis(p-nitrophenyl)carbonate or carbonyl diimidazole. This yields a molecule of the form $Y_1$—(C═O)—V—$R_1$—S—S-TLGS. This molecule is di-activated; the $Y_1$ group can be replaced by a nucleophile, while the (—S-TLGS) group can be replaced by a thiol-containing moiety. Thus, reaction with a cargo molecule of the form Carg-Nu(–), Carg-Nu(–)M+ (where M+ is one equivalent of a cation), or Carg-NuH yields the molecule Carg-Nu-(C═O)—V—$R_1$—S—S-TLGS. Reaction of this intermediate with a compound of the form Transp-SH forms the desired conjugate Carg-Nu-(C═O)—V—$R_1$—S—S-Transp.

An alternate route of synthesis is depicted as follows, which modifies the Carg-NuH molecule as follows:

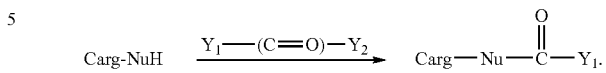

This product is then used in the following series of reactions:

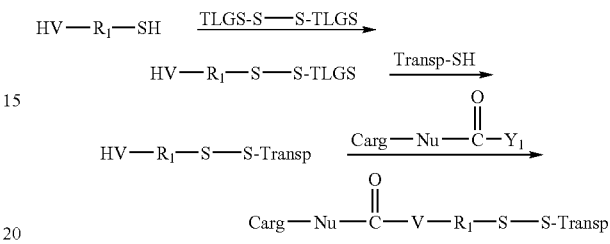

which yields the desired conjugate.

Modes of Administration

Compounds useful in the methods of the invention can be administered to a patient or subject (preferably a human patient or subject) via any route known in the art, including, but not limited to, those disclosed herein. Methods of administration include, but are not limited to, systemic, transpleural, intravenous, oral, intraarterial, intramuscular, topical, via inhalation (e.g. as mists or sprays), via nasal mucosa, subcutaneous (e.g., subcutaneous injection or subdermal injection), transdermal, intraperitoneal, intraocular, buccal, and gastrointestinal. The compounds described or incorporated by reference for use herein can be administered in the form of tablets, pills, powder mixtures, capsules, granules, injectables, creams, solutions, suppositories, emulsions, dispersions, food premixes, and in other suitable forms. The compounds can also be administered in liposome formulations. The compounds can also be administered as prodrugs, where the prodrug undergoes transformation in the subject to a form which is therapeutically effective. Additional methods of administration are known in the art.

The compounds for use in the invention are conveniently admixed with a pharmaceutically acceptable carrier, such as a non-toxic pharmaceutical organic carrier or a non-toxic pharmaceutical inorganic carrier. Typical pharmaceutically-acceptable carriers include, for example, mannitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical dosage form can also contain non-toxic auxiliary substances such as emulsifying, preserving, or wetting agents, and the like. A suitable carrier is one which does not cause an intolerable side effect, but which allows the compound(s) to retain its pharmacological activity in the body. Formulations for parenteral and nonparenteral drug delivery are known in the art and are set forth in *Remington: The Science and Practice of Pharmacy,* 20th Edition, Lippincott, Williams & Wilkins. Additional formulations are described in Rowe, Raymond C., Paul J. Sheskey, and Siân C. Owen, eds., *Handbook of Pharmaceutical Excipients,* 5th Edition, New York: McGraw-Hill/APhA Publications, 2005; and Gibson, Mark, *Pharmaceutical Preformulation and Formulation: A Practical Guide from*

*Candidate Drug Selection to Commercial Dosage Form*, Boca Raton: CRC, 2001. The compositions of the invention can be administered in the form of pharmaceutically acceptable salts; see Heinrich Stahl, P. and Camille G. Wermuth, eds., *Pharmaceutical Salts: Properties, Selection, and Use*, Hoboken, N.J.: Wiley-VCH, 2002. Solid forms, such as tablets, capsules and powders, can be fabricated using conventional tableting and capsule-filling machinery, which is well known in the art. Solid dosage forms, including tablets and capsules for oral administration in unit dose presentation form, can contain any number of additional non-active ingredients known to the art, including such conventional additives as excipients; desiccants; colorants; binding agents, for example syrup, acacia, gelatin, sorbitol, tragacanth, or polyvinylpyrollidone; fillers, for example lactose, sugar, maize-starch, calcium phosphate, sorbitol or glycine; tableting lubricants, for example magnesium stearate, talc, polyethylene glycol or silica; disintegrants, for example potato starch; or acceptable wetting agents such as sodium lauryl sulfate. The tablets can be coated according to methods well known in standard pharmaceutical practice. Liquid forms for ingestion can be formulated using known liquid carriers, including aqueous and non-aqueous carriers such as sterile water, sterile saline, suspensions, oil-in-water and/or water-in-oil emulsions, and the like. Liquid formulations can also contain any number of additional non-active ingredients, including colorants, fragrance, flavorings, viscosity modifiers, preservatives, stabilizers, and the like. For parenteral administration, the compounds for use in the invention can be administered as injectable dosages of a solution or suspension of the compound in a physiologically acceptable diluent or sterile liquid carrier such as water, saline, or oil, with or without additional surfactants or adjuvants. An illustrative list of carrier oils would include animal and vegetable oils (e.g., peanut oil, soy bean oil), petroleum-derived oils (e.g., mineral oil), and synthetic oils.

In one embodiment, the compounds of the invention are formulated into a pharmaceutical unit dosage form. The unit dosage contains a therapeutically effective amount of the compound of the invention.

For injectable unit doses, sterile liquids such as water, saline, phosphate-buffered saline, aqueous dextrose and related sugar solutions are preferred liquid carriers.

The pharmaceutical unit dosage chosen can fabricated and administered to provide a defined final concentration of drug either in the blood, or in the tissues of interest. The optimal effective concentration of the compounds of the invention can be determined empirically and will depend on the type and severity of the disease, route of administration, disease progression and health, mass and body area of the patient. Such determinations are within the skill of one in the art. Examples of dosages which can be used for systemic administration (including oral or parenteral) include, but are not limited to, an effective amount within the dosage range of about 0.1 µg/kg to about 300 mg/kg, or within about 1.0 µg/kg to about 40 mg/kg body weight, or within about 10 µg/kg to about 20 mg/kg body weight, or within about 0.1 mg/kg to about 20 mg/kg body weight, or within about 1 mg/kg to about 20 mg/kg body weight, or within about 0.1 mg/kg to about 10 mg/kg body weight, or within about within about 1 mg/kg to about 10 mg/kg body weight, or within about 0.1 µg/kg to about 10 mg/kg body weight. Examples of dosages which can be used for systemic administration (including oral and parenteral) when based on body surface area (expressed in square meters, or $m^2$) include, but are not limited to, an effective amount within the dosage range of about 0.1 µg/$m^2$ to about 300 mg/$m^2$ body surface area, or within about 10 µg/$m^2$ to about 300 mg/$m^2$ body surface area, or within about 100 µg/$m^2$ to about 300 mg/$m^2$ body surface area, or within about 1 mg/$m^2$ to about 300 mg/$m^2$ body surface area, or within about 10 mg/$m^2$ to about 300 mg/$m^2$ body surface area, or within about 10 mg/$m^2$ to about 200 mg/$m^2$ body surface area, or within about 10 mg/$m^2$ to about 120 mg/$m^2$ body surface area, or within about 40 mg/$m^2$ to about 120 mg/$m^2$ body surface area, or within about 60 mg/$m^2$ to about 100 mg/$m^2$ body surface area. The dosages may be administered in a single daily dose, or the total daily dosage may be administered in divided dosage of two, three or four times daily. Dosages may also be administered less frequently than daily, for example, six times a week, five times a week, four times a week, three times a week, twice a week, about once a week, about once every two weeks, about once every three weeks, about once every four weeks, about once every six weeks, about once every two months, about once every three months, about once every four months, or about once every six months.

In one embodiment of the invention, the dosages may be administered in a sustained release formulation or a sustained release implant, such as in an implant which gradually releases the compounds for use in the invention over a period of time, and which allow for the drug to be administered less frequently, such as about once a month, about once every 2-6 months, about once every year, or even a single administration which need not be repeated. The sustained release implants, devices or formulations (such as pellets, microspheres, and the like) can be administered by topical application, by injection, or can be surgically implanted in various locations.

In another embodiment of the invention, the conjugates and compounds of the invention can also be administered via topical administration. The term "topical administration" is used in its conventional sense to mean application of an active agent to the skin or mucosa to achieve a local effect. The conjugates and compounds for use in the present methods are contained in a topical formulation in a therapeutically effective concentration. The formulation can contain the selected compound in a suitable topical vehicle at any suitable total concentration, such as any of about 1 mM to about 1000 mM, about 10 mM to about 500 mM, or about 10 mM to about 100 mM.

Suitable concentrations of the conjugates or compounds can also be expressed in weight/volume or weight/weight percentage terms which may vary depending on the density of the vehicle and other components in the formulation. For example, a conjugate or compound may be present in the formulation at a concentration (w/v) of at least about any of 0.5%, 1%, 2%, 3%, 4%, 5%, 6%, 7%, 8%, 9%, or 10%. In embodiments for topical use, the concentration of the conjugate or compound is such that a topical dosage of approximately 0.5 grams of formulation over a 5 cm×5 cm area of skin (25 square cm) can be applied. In typical topical vehicles, the compositions are readily formulated and do not leave any significant visible residue when applied to the skin. Higher concentration formulations, such as saturated pastes or other forms, may also be successfully used, particularly where visible appearance is not a limiting consideration (as in therapeutic applications).

Routine clinical assessments can readily be employed to optimize the concentration of the conjugate or compound of the invention and to ascertain if lower or higher concentrations are appropriate for a given formulation or disorder. For example, in embodiments for topical use, the concentration may be adjusted to account for the amount of formulation that is typically applied topically by the user, which will depend to an extent on the physical nature of the topical vehicle (e.g., lotion as compared to liquid spray vehicles). Likewise, the amount of the compound required may be reduced in such cases where the formulation contains a penetration-enhancing ingredient or other agent which increases the ability of the compounds to permeate the stratum corneum.

The present formulations are prepared by mixing an appropriate amount of a selected conjugate or compound into the chosen formulation vehicle at an appropriate pH. Preferably, the selected conjugate or compound is sufficiently soluble in the formulation vehicle as to allow a consistent formulation having the desired physical application characteristics.

For topical applications, suitable topical vehicles for use with the formulations of the invention are well known in the cosmetic and pharmaceutical arts, and include such vehicles (or vehicle components) as water; organic solvents such as alcohols (particularly lower alcohols readily capable of evaporating from the skin such as ethanol), glycols (such as glycerin), aliphatic alcohols (such as lanolin); mixtures of water and organic solvents (such as water and alcohol); mixtures of organic solvents such as alcohol and glycerin (optionally also with water); lipid-based materials such as fatty acids, acylglycerols (including oils, such as mineral oil, and fats of natural or synthetic origin), phosphoglycerides, sphingolipids and waxes; protein-based materials—such as collagen and gelatin; silicone-based materials (both non-volatile and volatile) such as cyclomethicone, demethiconol and dimethicone copolyol (Dow Corning); hydrocarbon-based materials such as petrolatum and squalene; anionic, cationic and amphoteric surfactants and soaps; sustained-release vehicles such as microsponges and polymer matrices; stabilizing and suspending agents; and other vehicles and vehicle components that are suitable for topical administration, as well as mixtures of topical vehicle components as identified above or otherwise known to the art. The vehicle may further include components adapted to improve the stability or effectiveness of the applied formulation, such as preservatives, antioxidants, skin penetration enhancers, sustained release materials, and the like. Examples of such vehicles and vehicle components are well known in the art and are described in the drug formulation publications cited herein.

The compounds for use in the invention can be administered as the sole active ingredient, or can be administered in combination with another active ingredient.

Kits

The invention also provides articles of manufacture and kits containing compounds of the invention. The article of manufacture comprises a container with a label. Suitable containers include, for example, bottles, vials, and test tubes. The containers may be formed from a variety of materials such as glass or plastic. The container holds a composition having an active agent which is effective for treating or preventing a disease or indication. The label on the container indicates that the composition is used for treating or preventing a disease or indication, and may also indicate directions for use.

The invention also provides kits comprising any one or more of a compound of the invention. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

In other aspects, the kits may be used for any of the methods described herein, including, for example, to treat a patient or subject with a disease or indication or for prophylactic administration to a patient or subject at risk of developing a disease or indication. The kits may include instructions for practicing any of the methods described herein.

Uses of Conjugates

The conjugates can be used in varied therapeutic applications, including those described in U.S. Pat. No. 6,306,993, U.S. Pat. No. 6,495,663, U.S. Pat. No. 6,593,292, U.S. Pat. No. 6,669,951, U.S. Pat. No. 6,730,293 and U.S. Pat. No. 6,759,387; the diseases and therapeutical applications disclosed in those applications are hereby incorporated by reference herein in their entirety. To describe some of these therapeutic applications, the conjugates of the invention are useful for, inter alia, the delivery of biologically active and diagnostic agents across the skin. The conjugates can enter the viable epidermis, which is composed of the stratum granulosum, stratum lucidum and stratum germinativum which, along with the stratum corneum, make up the epidermis. Delivery in some embodiments of the invention is through the epidermis and into the dermis, including one or both of the papillary dermis and the reticular dermis. This ability to obtain penetration of one or more layers of the skin can greatly enhance the efficacy of compounds such as antibacterials, antifungals, antivirals, antiproliferatives, immunosuppressives, vitamins, analgesics, hormones, and the like. Numerous such compounds are known to those of skill in the art (see, e.g., Hardman and Limbird, Goodman & Gilman's The Pharmacological Basis of Therapeutics, McGraw-Hill, New York, 1996). In some embodiments, the agent is delivered into a blood vessel that is present in the epithelial tissue, thus providing a means for delivery of the agent systemically. Delivery can be either intrafollicular or interfollicular, or both. Pretreatment of the skin is not required for delivery of the conjugates. In other embodiments, the conjugates of the invention are useful for delivering cosmetics and agents that can treat skin conditions. Target cells in the skin that are of interest include, for example, fibroblasts, epithelial cells and immune cells. For example, the transporters provide the ability to deliver compounds such as antiinflammatory agents to immune cells found in the dermis.

Glucocorticoids (adrenocorticoid steroids) are among the compounds for which delivery across skin can be enhanced by the conjugates of the invention. Conjugated glucocorticoids of the invention are useful for treating inflammatory skin diseases, for example. Exemplary glucocorticoids include, e.g., hydrocortisone, prenisone (deltasone) and predrisonlone (hydeltasol). Examples of particular conditions include eczema (including atopic dermatitis, contact dermatitis, allergic dermatitis), bullous disease, collagen vascular diseases, sarcoidosis, Sweet's disease, pyoderma gangrenosum, Type I reactive leprosy, capillary hemangiomas, lichen planus, exfoliative dermatitis, erythema nodosum, hormonal abnormalities (including acne and hirsutism), as well as toxic epidermal necrolysis, erythema multiforme, cutaneous T-cell lymphoma, discoid lupus erythematosus, and the like.

Retinoids are another example of a biologically active agent for which one can use the conjugates of the invention to enhance delivery into and across one or more layers of the skin or other epithelial or endothelial tissue. Retinoids that are presently in use include, for example retinol, tretinoin, isotretinoin, etretinate, acitretin, and arotinoid. Conditions that are treatable using retinoids conjugated to the conjugates of the invention include, but are not limited to, acne, keratinization disorders, skin cancer, precancerous conditions, psoriasis, cutaneous aging, discoid lupus erythematosus, scleromyxedema, verrucous epidermal nevus, subcorneal pustular dermatosis, Reiter's syndrome, warts, lichen planus, acanthosis nigricans, sarcoidosis, Grover's disease, porokeratosis, and the like.

Cytotoxic and immunosuppressive drugs constitute an additional class of drugs for which the conjugates of the invention are useful. These agents are commonly used to treat hyperproliferative diseases such as psoriasis, as well as for immune diseases such as bullous dermatoses and leukocytoclastic vasculitis. Examples of such compounds that one can conjugate to the conjugates of the invention include, but are not limited to, antimetabolites and alkylating agents. Useful biological agents include, e.g., methotrexate, azathioprine, fluorouracil, hydroxyurea, 6-thioquanine, mycophenolate, chlorambucil, vinicristine, vinblasrine, dactinomycin, cyclophosphamide, mechloroethamine hydrochloride, carmustine, taxol, tacrolimus, vinblastine, dapsone and sulfasalazine. Immunosuppressive drugs such as cyclosporin and Ascomycins, such as FK506 (tacrolimus), and rapamycin (e.g., U.S. Pat. No. 5,912,253) and analogs of such compounds are of particular interest (e.g., Mollinson et al., Current Pharm. Design 4(5):367-380 (1998); U.S. Pat. Nos. 5,612,350; 5,599,927; 5,604,294; 5,990,131; 5,561,140; 5,859,031; 5,925,649; 5,994,299; 6,004,973 and 5,508,397). Cyclosporins include cyclosporin A, B, C, D, G and M. See, e.g., U.S. Pat. Nos. 6,007,840; and 6,004,973. For example, such compounds are useful in treating psoriasis, eczema (including atopic dermatitis, contact dermatitis, allergic dermatitis) and alopecia areata. Systemic administration is also contemplated.

The conjugates of the invention can be conjugated to agents that are useful for treating conditions such as lupus erythematosus (both discoid and systemic), cutaneous dermatomyositis, porphyria cutanea tarda and polymorphous light eruption. Agents useful for treating such conditions include, for example, quinine, chloroquine, hydroxychloroquine, and quinacrine.

The conjugates of the invention can also be used for transdermal delivery of antiinfective agents. For example, antibacterial, antifungal and antiviral agents can be conjugated to the conjugates of the invention. Antibacterial agents are useful for treating conditions such as acne, cutaneous infections, and the like. Antifungal agents can be used to treat tinea corporis, tinea pedis, onychomycosis, candidiasis, tinea versicolor, and the like. Because of the delivery-enhancing properties of the conjugates, these conjugates are useful for treating both localized and widespread infections. Antifungal agents are also useful for treating onychomycosis. Examples of antifungal agents include, but are not limited to, azole antifungals such as itraconazole, myconazole and fluconazole. Examples of antiviral agents include, but are not limited to, acyclovir, famciclovir, and valacyclovir. Such agents are useful for treating viral diseases, e.g., herpes.

Another example of a biologically active agent for which enhancement of delivery by conjugation to the conjugates of the invention is desirable are the antihistamines. These agents are useful for treating conditions such as pruritus due to urticaria, atopic dermatitis, contact dermatitis, psoriasis, and many others. Examples of such reagents include, for example, terfenadine, astemizole, lorotadine, cetirizine, acrivastine, temelastine, cimetidine, ranitidine, famotidine, nizatidine, and the like. Tricyclic antidepressants can also be delivered using the conjugates of the invention.

Topical antipsoriasis drugs are also of interest. Agents such as corticosteroids, calcipotriene, and anthralin can be conjugated to the conjugates of the invention and applied to skin.

The conjugates of the invention are also useful for enhancing delivery of photochemotherapeutic agents into and across one or more layers of skin and other epithelial tissues. Such compounds include, for example, the psoralens, and the like. Sunscreen components are also of interest; these include p-aminobenzoic acid esters, cinnamates and salicylates, as well as benzophenones, anthranilates, and avobenzone.

Pain relief agents and local anesthetics constitute another class of compounds for which conjugation to the conjugates of the invention can enhance treatment. Lidocaine, bupibacaine, novocaine, procaine, tetracaine, benzocaine, cocaine, and the opiates, are among the compounds that one can conjugate to the conjugates of the invention.

Other biological agents of interest include, for example, minoxidil, keratolytic agents, destructive agents such as podophyllin, hydroquinone, capsaicin, masoprocol, colchicine, and gold.

The conjugates of the invention are also useful for delivery of conjugated drugs by gastrointestinal administration. Gastrointestinal administration can be used for both systemically active drugs, and for drugs that act in the gastrointestinal epithelium. Among the gastrointestinal conditions that are treatable using appropriate reagents conjugated to the conjugates of the invention are Crohn's disease (e.g., cyclosporin and FK506), ulcerative colitis, gastrointestinal ulcers, peptic ulcer disease, imbalance of salt and water absorption (can lead to constipation, diarrhea, or malnutrition), abnormal proliferative diseases, and the like. Ulcer treatments include, for example, drugs that reduce gastric acid secretion, such as $H_2$ histamine inhibitors (e.g., cymetidine and ranitidine) and inhibitors of the proton-potassium ATPase (e.g., lansoprazle and omeprazle), and antibiotics directed at *Helicobacter pylori*.

Antibiotics are among the biologically active agents that are useful when conjugated to the conjugates of the invention, particularly those that act on invasive bacteria, such as *Shigella, Salmonella*, and *Yersinia*. Such compounds include, for example, norfloxacin, ciprofloxacin, trimethoprim, sulfamethyloxazole, and the like.

Anti-neoplastic agents can also be conjugated to the conjugates of the invention and administered by the gastrointestinal route. These include, for example, cisplatin, methotrexate, taxol, fluorouracil, mercaptopurine, donorubicin, bleomycin, and the like. The conjugates of the invention can be used to treat cancer, including breast cancer, ovarian cancer, prostate cancer, skin cancer, gastrointestinal cancers, blood malignancies, and ophthalmic cancers. They can also be used to treat uncontrolled cell proliferation, for example, benign growths on the skin.

The conjugates of the invention can also used to enhance administration of drugs through the respiratory tract. The respiratory tract, which includes the nasal mucosa, hypopharynx, and large and small airway structures, provides a large mucosal surface for drug absorption. The enhanced penetration of the conjugated agents into and across one or more layers of the epithelial tissue that is provided by the conjugates of the invention results in amplification of the advantages that respiratory tract delivery has over other delivery methods. For example, lower doses of an agent are often needed to obtain a desired effect, a local therapeutic effect can occur more rapidly, and systemic therapeutic blood levels of the agent are obtained quickly. Rapid onset of pharmacological activity can result from respiratory tract administration. Moreover, respiratory tract administration generally has relatively few side effects.

The transporters of the invention can be used to deliver biological agents that are useful for treatment of pulmonary conditions. Examples of conditions treatable by nasal administration include, for example, asthma. These compounds include antiinflammatory agents, such as corticosteroids, cromolyn, and nedocromil, bronchodialators such as beta-2-selective adronergic drugs and theophylline, and immunosuppressive drugs (e.g., cyclosporin and FK506). Other conditions include, for example, allergic rhinitis (which can be treated with glucocorticoids), and chronic obstructive pulmonary disease (emphysema). Other drugs that act on the pulmonary tissues and can be delivered using the transporters of the invention include beta-agonists, mast cell stabilizers, antibiotics, antifungal and antiviral agents, surfactants, vasoactive drugs, sedatives and hormones.

Respiratory tract administration is useful not only for treatment of pulmonary conditions, but also for delivery of drugs to distant target organs via the circulatory system. A wide variety of such drugs and diagnostic agents can be administered through the respiratory tract after conjugation to the conjugates of the invention.

The conjugates of the invention are also useful for delivering biologically active and diagnostic agents across the blood brain barrier. The agents are useful for treating ischemia (e.g., using an anti-apoptotic drug), as well as for delivering neurotransmitters and other agents for treating various conditions such as schizophrenia, Parkinson's disease, pain (e.g., morphine, the opiates). The 5-hydroxytryptamine receptor antagonist is useful for treating conditions such as rmigraine headaches and anxiety.

The conjugates of the invention are also useful for delivery of diagnostic imaging and contrast agents into and across one or more layers of an epithelial and/or endothelial tissue. Examples of diagnostic agents include substances that are labeled with radioactivity, such as $^{99m}$Tc glucoheptonate, or substances used in magnetic resonance imaging (MRI) procedures such as gadolinium doped chelation agents (e.g. Gd-DTPA). Other examples of diagnostic agents include marker genes that encode proteins that are readily detectable when expressed in a cell (including, but not limited to, (beta-galactosidase, green fluorescent protein, luciferase, and the like. A wide variety of labels may be employed, such as radionuclides, fluors, enzymes, enzyme substrates, enzyme cofactors, enzyme inhibitors, ligands (particularly haptens), etc.

The following examples are provided to illustrate various embodiments of the invention, and are not intended to limit the invention in any manner.

EXAMPLES

Unless otherwise stated, all reagents and solvents were obtained from commercial sources and used without purification. Analytical TLC was performed with 0.25 mm silica gel 60F plates with fluorescent indicator (254 nm). Plates were visualized by ultraviolet light and treatment with either ammonium molybdate stain (prepared by combining 90 g of ammonium molybdate, 6 g of cerium sulfate, and 1800 ml of 10% $H_2SO_4$) or potassium permanganate stain (prepared by combining 8 g of $KMnO_4$, 60 g of $K_2CO_3$, 16 ml of 5% NaOH, and 900 ml $H_2O$). Reverse-phase high performance liquid chromatography (RP-HPLC) was performed with a Varian ProStar 210/215 HPLC using a preparative column (Alltec Alltima C18, 250×22 mm) or on an Agilent 1100 analytical HPLC with an analytical column (Vydak C18, 150×4.6 mm). The products were eluted utilizing a solvent gradient (solvent A=0.1% TFA/$H_2O$; solvent B=0.1% TFA/$CH_3CN$). NMR spectra were measured on a Varian INOVA 500 ($^1$H NMR at 500 MHz; $^{13}$C NMR at 125 MHz) or a Varian INOVA 400 ($^1$H NMR at 400 MHz; $^{13}$C NMR at 100 MHz) magnetic resonance spectrometer. Data for $^1$H NMR spectra are reported as follows: chemical shift, multiplicity (s=singlet, d=doublet, dd=doublet of doublet, t=triplet, q=quartet, and m=multiplet), integration, and coupling constant (Hz). Data for $^{13}$C NMR spectra are reported in terms of chemical shift relative to residual solvent peak ($CDCl_3$=77.3 ppm and $CD_3OD$=49.1 ppm). Infrared spectra were recorded on a Perkin-Elmer 1600 Series FTIR. High resolution mass spectra (HRMS) were recorded at the NIH regional mass spectrometry facility at the University of California, San Francisco. Electrospray ionization mass spectra (ES-MS) were recorded at the mass spectrometry lab at Stanford University on a Finnigan LCQ quadrupole ion trap mass spectrometer. Matrix Assisted Laser Desorption mass spectra (MALDI) were recorded on an Applied Biosystems Voyager DE mass spectrometer.

Example 1

Synthesis of the Series of Compounds 2

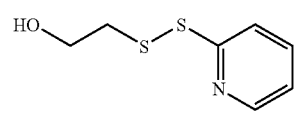

2a

Synthesis of Compound 2a, depicted in FIG. 1A, was performed as follows. To an oven dried three-necked flask under nitrogen at room temperature equipped with a stir bar was added 2'-aldrithiol (4.71 g, 21.4 mmol) in 20 ml degassed methanol. To this mixture was added 2-mercaptoethanol dropwise (500 μl, 7.10 mmol). The solution turned yellow and was allowed to stir for two hours. The solvent was then removed in vacuo and flash chromatography was performed using 20% ethyl acetate and methylene chloride. The product was a yellow oil (1.320 g, 7.06 mmol, 97% yield) and homogeneous (one spot) by TLC $R_f$=0.47 (5% EtOAc, DCM). $^1$H NMR (500 MHz, $CD_3OD$): δ 8.15-8.14 (m, 1H), 7.59-7.53 (m, 2H), 7.00-6.97 (m, 1H), 3.51 (t, 2H, J=6.5 Hz), 2.68 (t, 2H, J=6.5 Hz). $^{13}$C NMR (400 MHz, $CDCl_3$): δ 159.3, 150.0, 137.1, 122.0, 121.7, 58.5, 42.8. IR (thin film): 3349, 2920, 2865, 1574, 1559, 1446, 1285, 1116, 1063, cm$^{-1}$, HRMS (m/z): [M+] calculated for $C_7H_9NOS_2$: 187.0126; found: 187.0123.

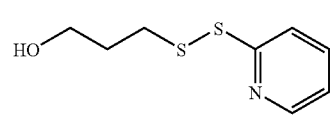

2b

Compound 2b, depicted in FIG. 1A, was synthesized as described above for 2a beginning with 3-mercapto-propanol in 91% yield. $^1$H NMR (500 MHz, $CD_3OD$): δ=8.35 (m, 1H), 7.84 (m, 1H), 7.78 (m, 1H), 7.19 (m, 1H), 3.60 (t, 2H, J=6.5 Hz), 2.87 (t, 2H, J=6.5 Hz), 1.87 (m, 2H). $^{13}$C NMR (500 MHz, $CD_3OD$) δ 161.0, 149.5, 139.5, 122.2, 121.2, 60.7, 36.1, 32.5. IR (film, cm$^{-1}$) 3359, 2934, 1784, 1688, 1574, 1446. EI-MS (m/z): [M+] calculated for $C_8H_{11}NOS_2$ 201.0282; found 201.0275.

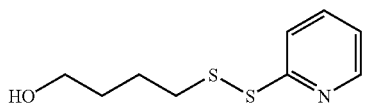
2c

Compound 2c, depicted in FIG. 1A, was synthesized as described above for 2a beginning with 3-mercapto-butanol in 82% yield. $^1$H NMR (500 MHz, CD$_3$OD); δ 8.45-8.43 (m, 1H), 7.91-7.86 (m, 2H), 7.25-7.18 (m, 1H), 3.59 (t, 2H, J=6.5 Hz), 2.87 (t, 2H, J=6.5 Hz), 1.92-1.85 (m, 4H). $^{13}$C NMR (400 MHz, CDCl$_3$): δ 160.6, 149.7, 137.3, 120.9, 112.9, 62.3, 38.9. 31.6. 25.5. IR (thin film): 3365, 2933, 2863, 1575, 1560, 1446, 1440, 1118, 1062, 1044 cm$^{-1}$. HRMS (m/z): [M+] calculated for C$_9$H$_{13}$NOS$_2$ 215.0439; found 215.0433.

Example 2

Synthesis of the Series of Compounds 4

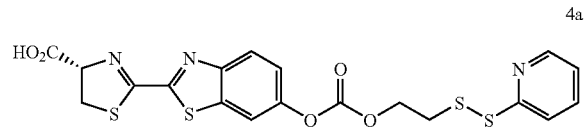 [SMILES: O=C(OCCSSc1ccccn1)Oc1ccc2nc(C3=N[C@@H](C(=O)O)CS3)sc2c1]
4a

Compound 4a, depicted in FIG. 1A, was synthesized as follows. To an oven dried flask equipped with a stir bar and a Teflon cap under argon was added 2a (44.0 mg, 0.235 mmol), triphosgene (25.0 mg, 0.0842 mmol), and pyridine (18.0 μl, 0.222 mmol) in methylene chloride (3 ml) at room temperature. The solution remained clear. This was allowed to stir for 30 minutes then the solvent was evaporated in vacuo to afford a white bubbly solid. To this was added luciferin (30.0 mg, 94.3 μmol) and NaOH (547 μl of 0.5 M, 0.273 mmol) in water (3 ml) that had been chilled in brine and ice. The solution turned cloudy white, purple then cloudy yellow. The reaction was stirred for 4 hours at 4° C., quenched with 1% TFA and water (15 ml) and extracted three times with methylene chloride. The solvent was evaporated in vacuo the compound was purified using flash chromatography with 20% ethyl acetate, 1% acetic acid, and methylene chloride. The appropriate fractions were isolated then further purified by RP-HPLC. Appropriate fractions were lyophilized to afford a yellow solid (27 mg, 54.5 μmol, 58%), which was homogeneous (one spot) by TLC R$_f$=0.4 (20% EtOAc, 1% acetic acid, DCM). $^1$H NMR (400 MHz, CDCl$_3$) δ 8.59-8.58 (m, 1H), 8.15 (d, 1H, J=9 Hz), 7.85-7.77 (m, 3H), 7.36 (dd, 1H, J=9 Hz), 7.23-7.23 (m, 1H), 5.46 (t, 1H, J=8.4 Hz), 4.55 (t, 2H, J=8.4 Hz), 3.84-3.81 (m, 2H), 3.18 (t, 2H, J=8.4 Hz). $^{13}$C NMR (500 MHz, CDCl$_3$); δ 172.9, 167.5, 161.0, 159.2, 153.3, 151.3, 150.0, 148.8, 139.0, 137.9, 130.6, 125.6, 122.0, 121.2, 114.5, 78.2, 66.5, 37.3, 35.4. IR (thin film): 3350, 2952, 2360, 1761, 1587, 1448, 1418, 1201, 1196, 1043 cm$^{-1}$. EI-MS (m/z): [M+1] calculated for C$_{19}$H$_{16}$N$_3$O$_5$S$_4$ 493.9; (H+) found 493.9.

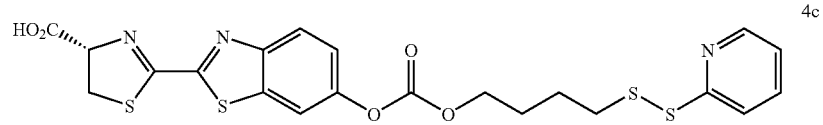 [SMILES: O=C(OCCCCSSc1ccccn1)Oc1ccc2nc(C3=N[C@@H](C(=O)O)CS3)sc2c1]
4b

Compound 4b, depicted in FIG. 1A, was synthesized as described above for 4a beginning with 2b in 47% yield and >99% purity by analytical HPLC. $^1$H NMR (500 MHz, CD$_3$OD) δ 8.43 (m, 1H), 8.11 (d, 1H, J=9 Hz), 7.97 (d, 1H, J=2 Hz), 7.86 (m, 1H), 7.81 (m, 1H), 7.44 (dd, 1H, J=9 Hz), 7.27 (m, 1H), 5.46 (t, 1H, J=9 Hz), 4.41 (t, 2H, J=6.5 Hz), 3.81 (dd, 2H, J=9 Hz), 2.95 (t, 2H, J=6.5 Hz), 2.16 (m, 2H). $^{13}$C NMR (500 MHz, CD$_3$OD) δ 168.1, 162.9, 161.2, 154.7, 152.2, 151.5, 150.4, 139.1, 137.9, 130.4, 125.8, 122.4, 121.3, 121.2, 115.8, 79.7, 68.3, 43.8, 35.9, 29.1. IR (film, cm$^{-1}$) 3045, 2958, 1761, 1574, 1417, 1236. EI-MS (m/z): [M+1] calculated for C$_{20}$H$_{18}$N$_3$O$_5$S$_4$ 508.00; found 508.06.

Compound 4c was synthesized as described above for 4a beginning with 2c in 67% yield. The product was homogeneous (one spot) by TLC Rf=0.56 (20% EtOAc, 1% acetic acid, DCM). $^1$H NMR (400 MHz, CD$_3$OD); δ 8.42-8.41 (m, 1H), 8.10 (d, 1H, J=8.8), 7.93-7.83 (m, 3H), 7.41 (dd, 1H, J=8.8 Hz), 7.27-7.24 (m, 1H), 5.42 (t, 1H, J=8.8 Hz), 4.27 (t, 2H, J=6.0 Hz), 3.79 (dd, 2H, J=8.8), 2.89 (t, 2H, J=6.8), 1.86-1.83 (m, 4H). $^{13}$C NMR (500 MHz, CDCl$_3$); δ 171.9, 167.45, 160.7, 159.2, 153.3, 151.2, 149.9, 148.5, 138.8, 136.7, 130.5, 125.3, 121.6, 121.1, 114.3, 75.5, 66.4 38.9, 37.1, 35.3, 30.3. IR (thin film): 2937, 1760, 1586, 1496, 1447, 1417, 1231, 1197, 1043, 874 cm$^{-1}$. EI-MS (m/z): [M+1] calculated for C$_{21}$H$_{20}$N$_3$O$_5$S$_4$ 522.02; found 522.0.

The above reactions proceed through the chloroformate intermediates (1-chloroformyloxy)ethyl 2-pyridinyl disulfide (3a, n=1), (1-chloroformyloxy)propyl 2-pyridinyl disulfide (3b, n=2), and (1-chloroformyloxy)butyl 2-pyridinyl disulfide (3c, n=3), with reference to the structure below.

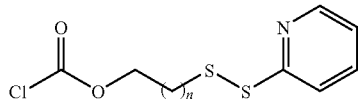

Example 3

Synthesis of the Series of Compounds 5

Figure 1B:
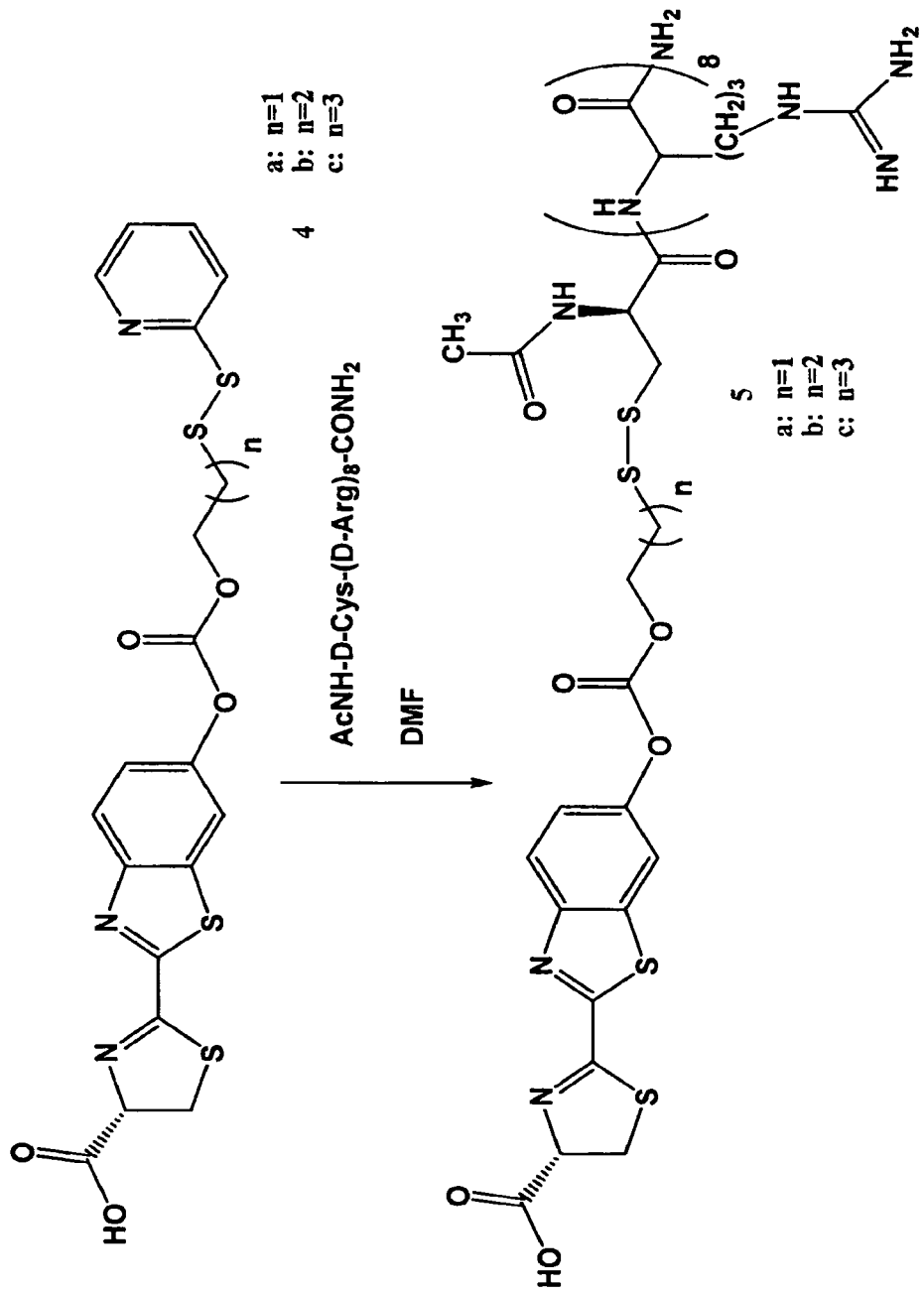
FIG. 1B shows conjugation of the disulfide-activated agent with the transporter polymer.

Conjugate 5a, as depicted in FIG. 1B, was synthesized as follows. To an oven dried test tube under nitrogen equipped with a stir bar was added Ac-D-Cys-(D-Arg)$_8$-CONH$_2$.8TFA (20 mg, 8.61 µmol) in degassed 1:1 acetonitrile and water (2 ml). To this was added 4a (7.10 mg 14.4 µmol) in 0.5 ml acetonitrile and DMSO. The reaction was allowed to stir for 16 hours then purified by RP-HPLC. Appropriate fractions were lyophilized to afford a white solid (15 mg, 5.54 µmol, 64% yield) which was >99% pure by analytical HPLC. $^1$H NMR (400 MHz, D$_2$O) δ 8.00 (d, 1H, J=8.8 Hz), 7.87 (d, J=2, 1H), 7.38 (dd, 1H, J=8.8 Hz), 5.23 (t, 1H, J=8.8 Hz), 4.41-4.38 (m, 2H), 4.15-4.02 (m, 9H), 3.78-3.58 (m, 2H), 3.05-2.87 (m, 20H), 1.88 (s, 3H), 1.66-1.45 (m, 32H). MS (m/z): [M+3] calculated for C$_{67}$H$_{119}$N$_{36}$O$_{15}$S$_4$ 1795.8; found (MALDI) 1795.8.

Conjugate 5b, as depicted in FIG. 1B, was synthesized as described above for 5a beginning with compound 4b and Ac-D-Cys-(D-Arg)$_8$-CONH$_2$, in 66% yield and >99% pure by analytical HPLC. $^1$H NMR (500 MHz, CD$_3$OD) 8.16 (d, 1H, J=9 Hz), 7.99 (d, 1H, J=2 Hz), 7.46 (dd, 1H, J=9 Hz), 5.46 (t, 1H, J=9 Hz), 4.42 (t, 2H, J=6.5 Hz), 4.27-4.35 (m, 9H), 3.81 (dd, 2H, J=9 Hz), 3.15-3.23 (m, 18H), 2.91 (t, 2H, J=6.5 Hz), 2.17 (m, 2H), 2.05 (s, 3H), 1.60-1.95 (m, 32H). MS (m/z): [M+1] calculated for C$_{68}$H$_{119}$N$_{36}$O$_{15}$S$_4$ 1807.85; found (MALDI) 1807.84.

Conjugate 5c, as depicted in FIG. 1B, was synthesized as described above for 5a beginning with compound 4c and Ac-D-Cys-(D-Arg)$_8$-CONH$_2$ in 24% yield and >99% pure by analytical HPLC. $^1$H NMR (400 MHz, D$_2$0) δ 7.97 (d, 1H, J=8.8 Hz) 7.82 (d, 1H, J=2), 7.34 (dd, 1H, J=8.8 Hz), 5.17 (t, 1H, J=8.8 Hz), 4.22-4.04 (m, 11H), 3.75-3.55 (m, 2H), 3.02-2.83 (m, 18H), 2.68-2.59 (m, 2H), 1.83 (s, 3H), 1.64-1.45 (m, 36H). MS (m/z): [M+2] calculated for C$_{69}$H$_{122}$N$_{36}$O$_{15}$S$_4$ 1822.86; found (MALDI) 1822.05 (M+1).

Example 4

Assay Measuring the Release of Luciferin from and Decomposition of Conjugates 5a, 5b, and 5c The stabilities of the conjugates were assayed by measuring their decomposition when incubated in HEPES buffered saline (HBS, pH 7.4) at 37° C. using analytical HPLC. Each of the conjugates 5a, 5b, and 5c (0.2 mg) were dissolved in 250 µl HBS at pH 7.4 in 1.5 ml microfuge tubes and incubated at 37° C. containing 10 µl of a solution of 10 mg of 1-naphthalenemethanol in 24 ml of methanol, which served as an internal standard. At appropriate time points 20 µl of the solutions were removed and analyzed by reverse phase HPLC. The percent decomposition was calculated from the integrated peak areas of the conjugate, the internal standard, and the various decomposition products.

Figure 1C:
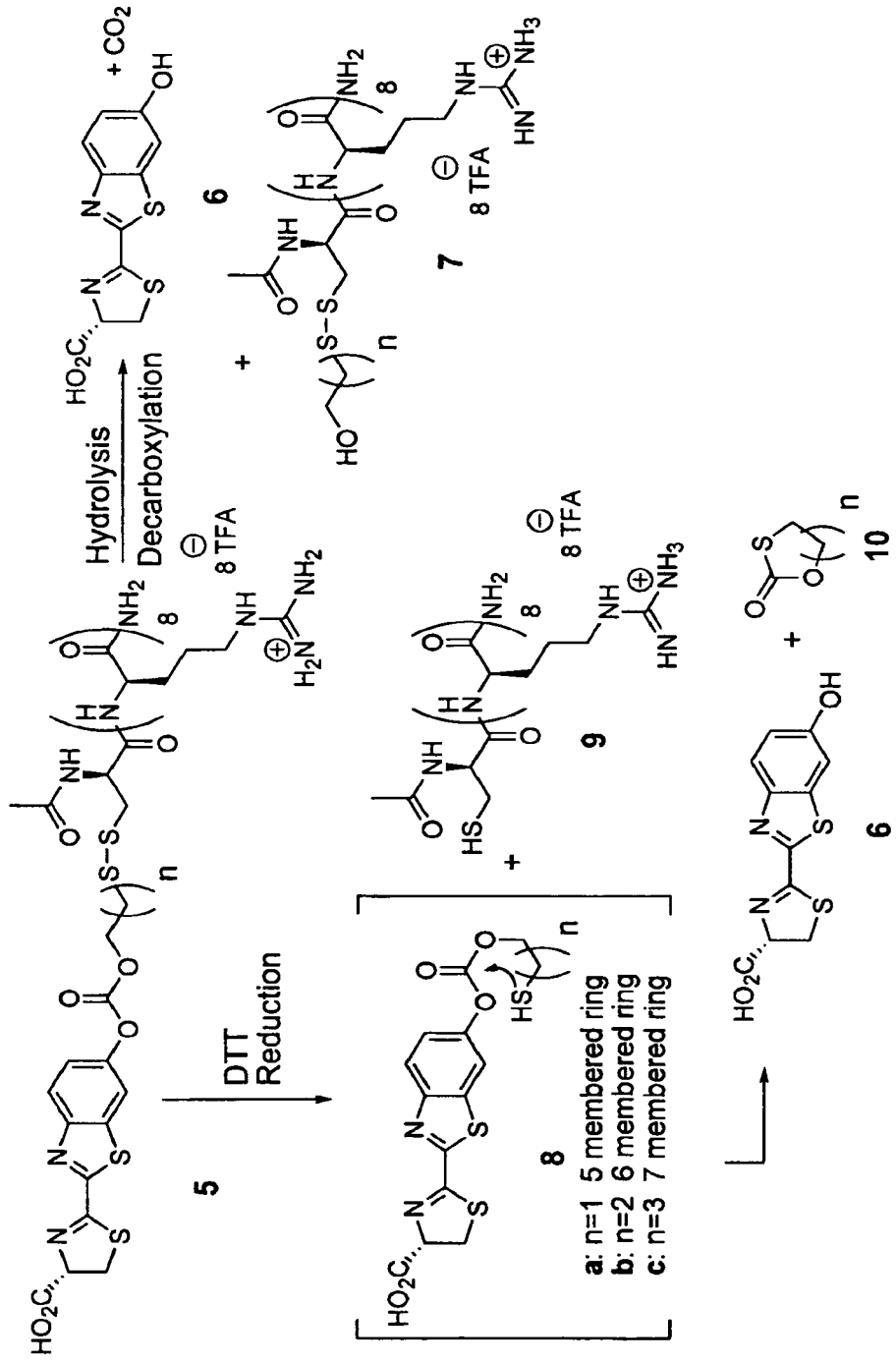
FIG. 1C shows the reaction products resulting from hydrolysis and decarboxylation of the conjugates, and the reaction products resulting from disulfide cleavage of the conjugates.

The half-lives of the conjugates differed significantly, ranging from 3 hours for carbonate 5a, to 11 hours for carbonate 5b, to 33 hours for carbonate 5c. The decomposition products were luciferin, alcohol 7, and CO$_2$ as expected from slow hydrolysis of the carbonate (FIG. 1C). The pattern of increasing stability correlates with the increasing distance between the carbonyl group and the proximate sulfur atom, suggesting a role for the latter in the hydrolysis step.

Example 5

Cell Free Assay for Determination of Release of Agent from Conjugate

Figure 2A:
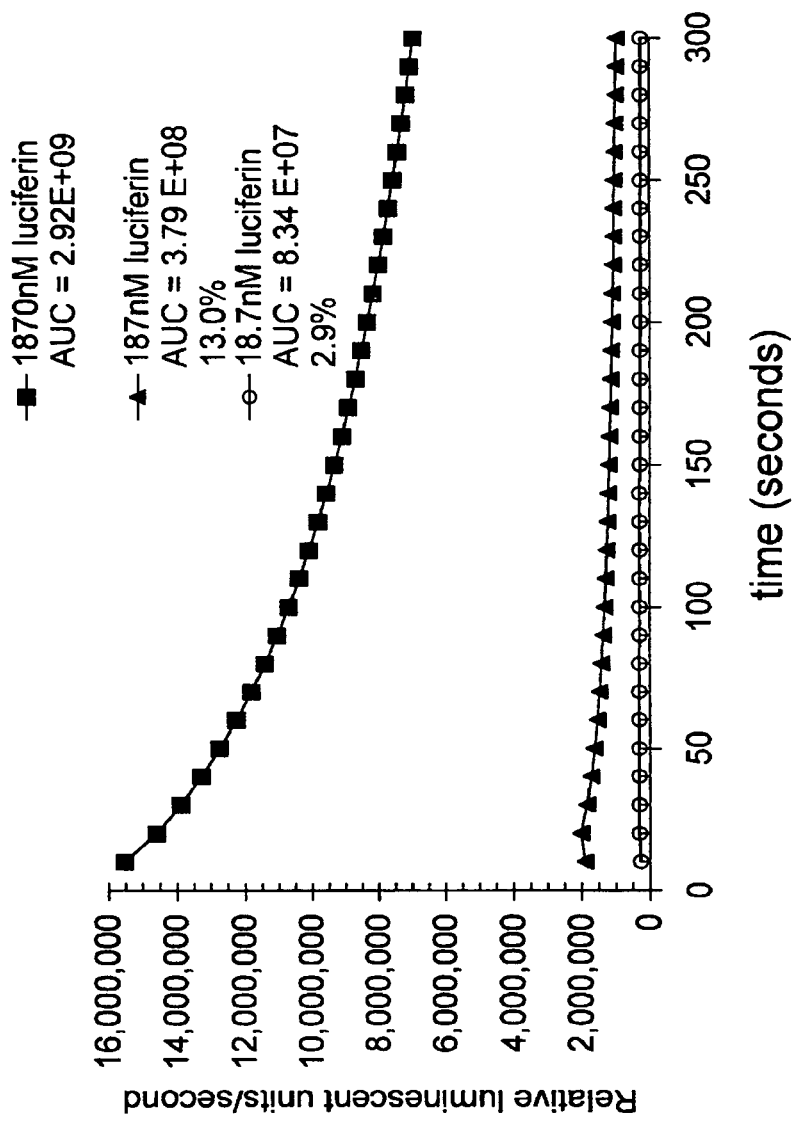
FIG. 2A shows standard curves of luminescence resulting from the addition of known amount of luciferin to 100 ng of firefly luciferase in 5 mM $MgSO_4$, 200 mM NaCl, 20 mM HEPES, 1 mM EDTA, 1 mM DTT, 2 mM ATP, pH 7.4. Units for the integrated area under the curves (AUC) are photons. The percentiles represent normalized amounts of light to the highest dose of luciferin.
Figure 2B:
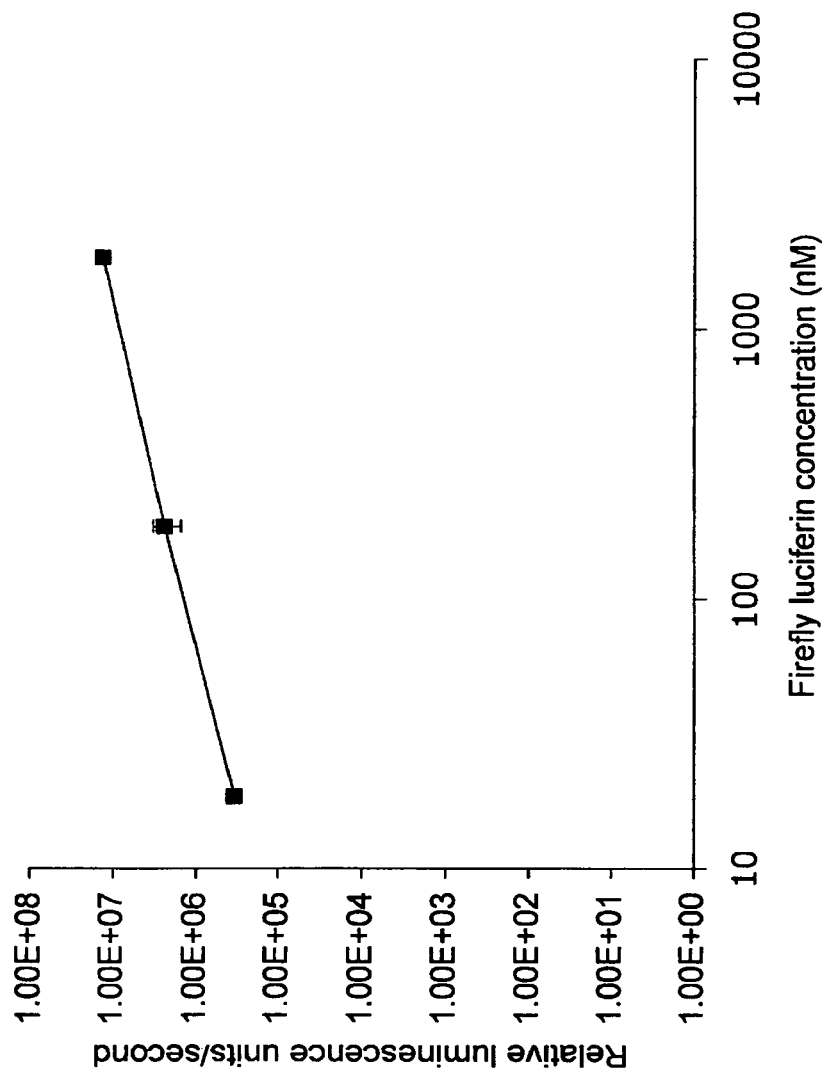
FIG. 2B shows the relationship between the concentration of luciferin and the relative luminescence for the conditions in FIG. 2A. A linear relationship was observed when the log of the concentration was plotted as a function of the log of the concentration of luciferin.

The relative rates of release of luciferin from conjugates 5b and 5c in a reducing environment were measured by incubating varying concentrations of the conjugates with firefly luciferase (Promega, Madison, Wis.) and measuring the resultant luminescence as a function of time using a luminometer (Berthold Detection Systems, model: Sirius). Standard curves measuring the amount of light generated by luciferin were produced by adding varying concentrations (from 20-2000 nM) of the potassium salt of luciferin (Xenogen Corp., Alameda, Calif.) in 50 µl of 5 mM MgSO$_4$, 200 mM NaCl, 20 mM HEPES, 1 mM EDTA pH 7.4 to 100 ng of firefly luciferase in 50 µl of the same buffer containing 1 mM DTT, 2 mM ATP. Light produced was found to be linear in the concentration range used in this study (see FIG. 2B).

Figure 3A:
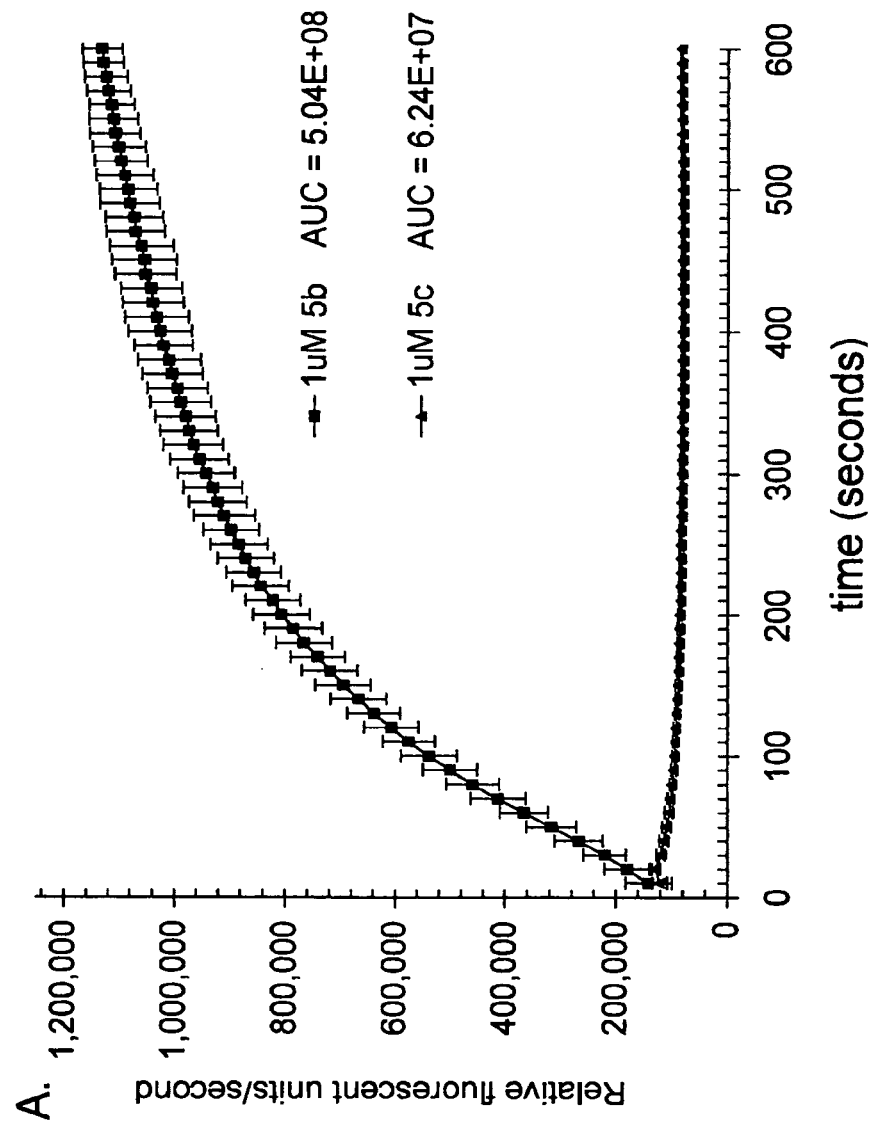
FIG. 3A shows the resultant luminescence produced when carbonates 5b and 5c were mixed with luciferase; 1 uM solutions of carbonate 5b and 5c were mixed with 100 ng of firefly luciferase in 5 mM $MgSO_4$, 200 mM NaCl, 20 mM HEPES, 1 mM EDTA, 1 mM DTT, 2 mM ATP at pH 7.4. Units for the integrated area under the curves (AUC) are photons.
Figure 3B:
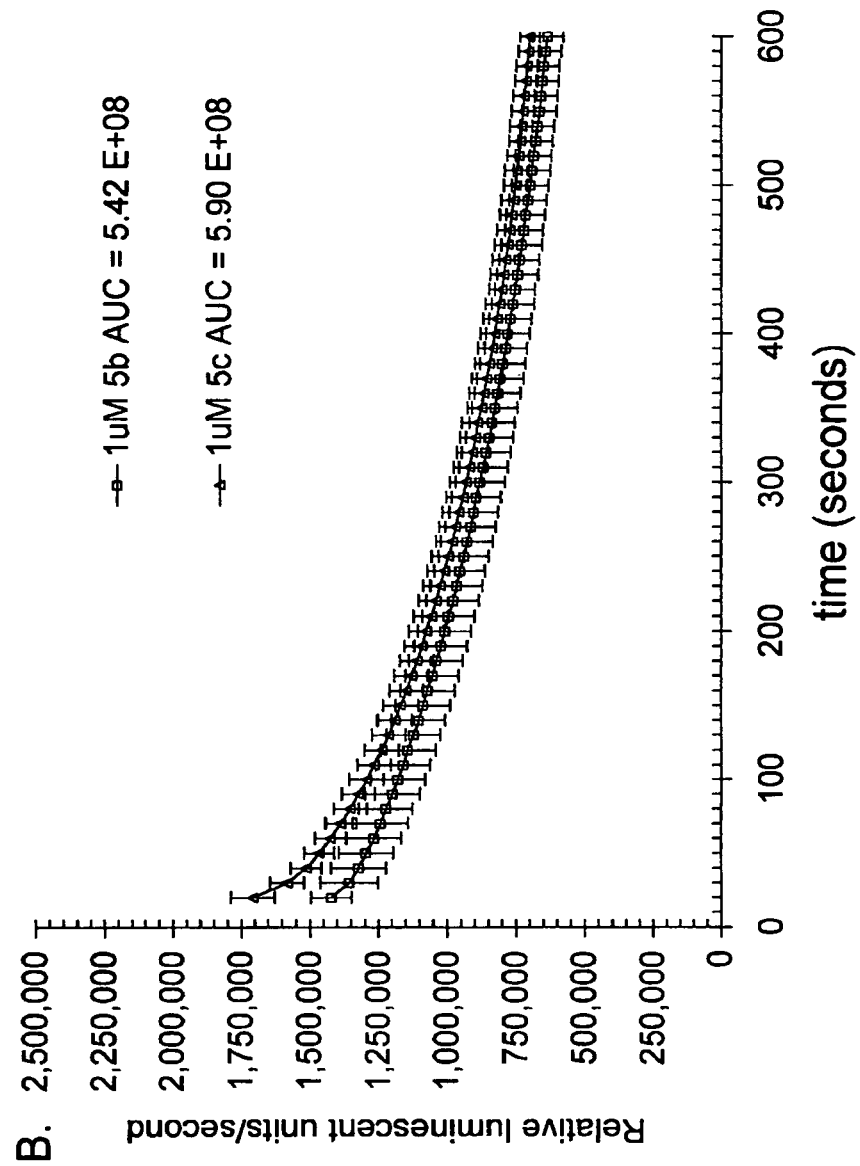
FIG. 3B shows the resultant luminescence when the conjugates of FIG. 3A were preincubated (reduced) with 1 mM DTT for 20 minutes prior to exposure to firefly luciferase; the profile of luminescence is similar to that seen for luciferin, and equivalent amounts of light were produced for both conjugates.

To determine the relative rates of release of luciferin from the conjugates in a reducing environment, 50 µl of a 50 µM solution of carbonates 5b and 5c in 5 mM MgSO$_4$, 200 mM NaCl, 20 mM HEPES, 1 mM EDTA, pH 7.4 were added to 100 ng of firefly luciferase in 50 µl of the same buffer containing 1 mM DTT, 2 mM ATP and the resultant light was measured. There was a significant difference in light produced, with carbonate 5c generating only approximately 12% of the light generated by carbonate 5b (FIG. 3A). Equivalent molar amounts of luciferin were released from each conjugate as established by preincubation with 1 mM DTT for 20 minutes prior to the addition of the enzyme. Under these conditions, the profile of luminescence was similar to that seen with purified luciferin (FIG. 2A) and equivalent amounts of light was observed for both conjugates. (FIG. 3B). One possible explanation for the differences is that the life-time of the intermediate of 5c is much greater than that for 5b, allowing it to compete with released luciferin for the binding site of luciferase. This hypothesis is supported by the fact that the 6-O methyl ether of luciferin, similarly alkylated at the phenol, is a known inhibitor of luciferase (Denburg et al., Arch. Biochem. Biophys. 134:381 (1969)).

Example 6

Cellular Assays for Luciferin Release from Conjugates

To study uptake and release in cell culture, varying concentrations of luciferin, 5b, and 5c were incubated separately with a prostate cancer cell line stably transfected with a luciferase encoding gene, PC3M-luc. The PC3M-luc prostate tumor cell line (Jenkins et al., Clin. Exp. Metastasis 20:733 (2003)), was plated at 60,000 cells per well in 96 well, flat bottomed plates twelve hours prior to the assay. The cells were incubated with varying concentrations of either the potassium salt of luciferin (Xenogen Corp., Alameda, Calif.) or carbonates 5b or 5c, in triplicate, for 1 minute, in either HEPES buffered saline (HBS) pH 7.4 or K+HBS (HEPES buffered saline in which all sodium salts were replaced with equimolar amounts of the potassium salt). The cells were washed to remove extracellular luciferin or conjugate, resuspended with the appropriate buffer, and the resultant luminescence measured using a charged coupled device camera and Living Image software (IVIS200, Xenogen Corp., Alameda, Calif.) (see Cao et al., Proc. Natl. Acad. Sci. U.S.A. 101:221 (2004)).

Figure 4A:
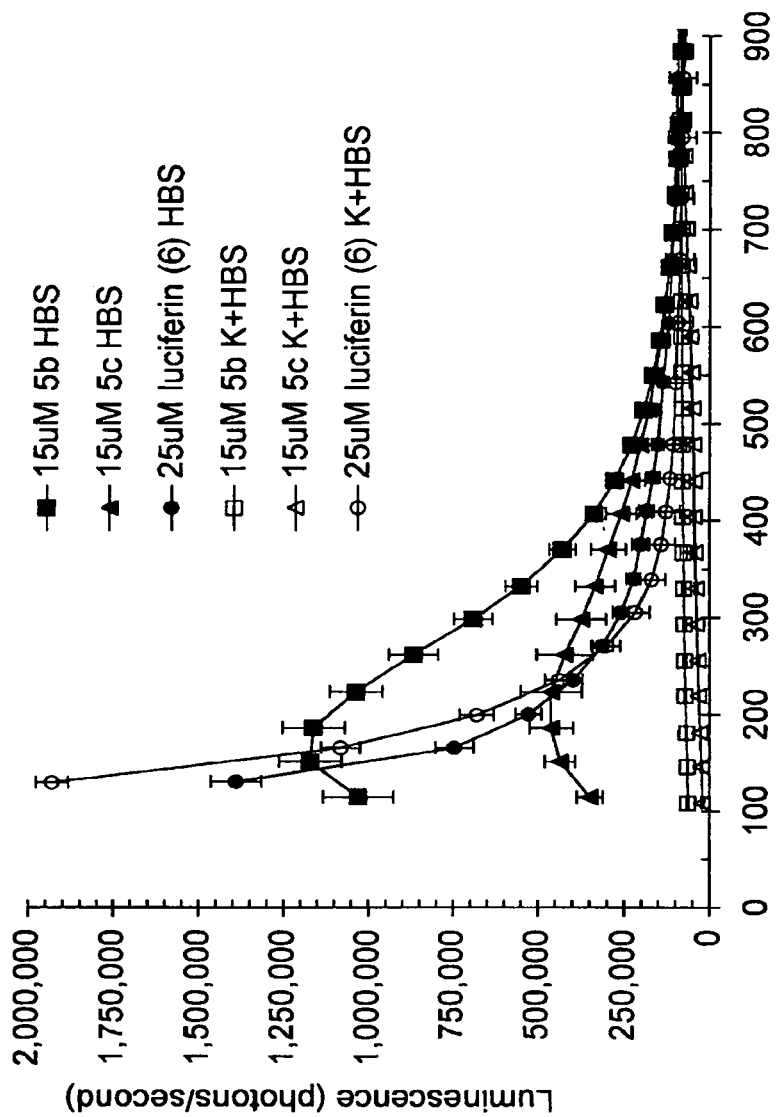
FIG. 4A shows real time measurement of bioluminescence from a prostate cancer cell line stably transfected with luciferase (PC3M-luc) treated with 25 μM luciferin (6) or 15 μM releasable luciferin conjugates, 5b or 5c, in either HBS or K+HBS.
Figure 4B:
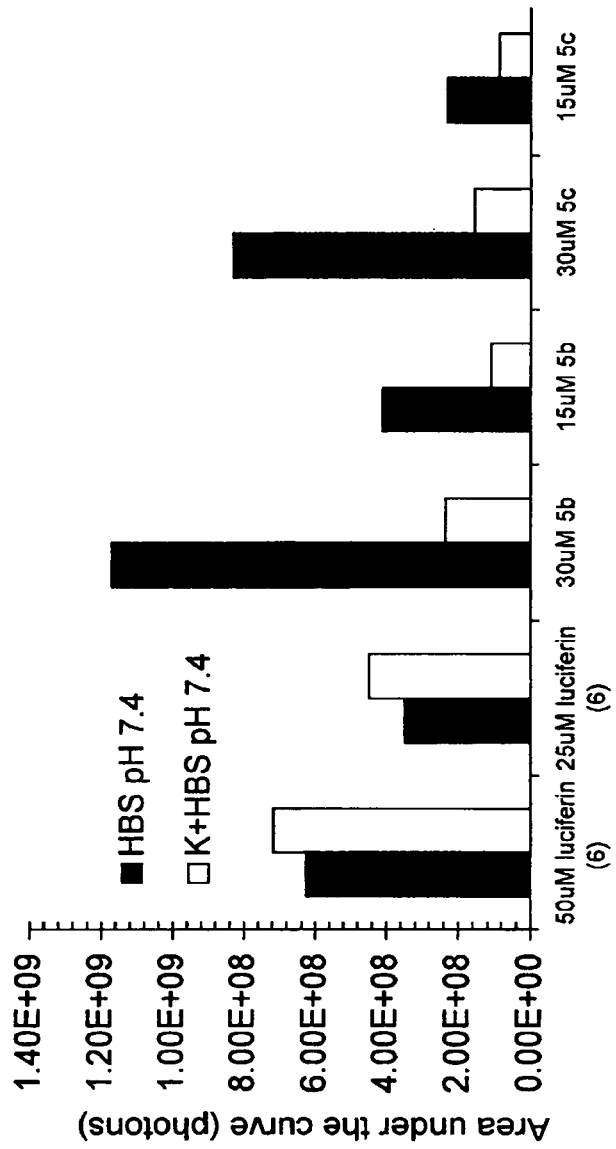
FIG. 4B shows total luminescence from a prostate cancer cell line stably transfected with luciferase (PC3M-luc) treated with 25 μM luciferin (6) or 15 μM releasable luciferin conjugates, 5b or 5c, in either HBS or K+HBS.
Figure 5:
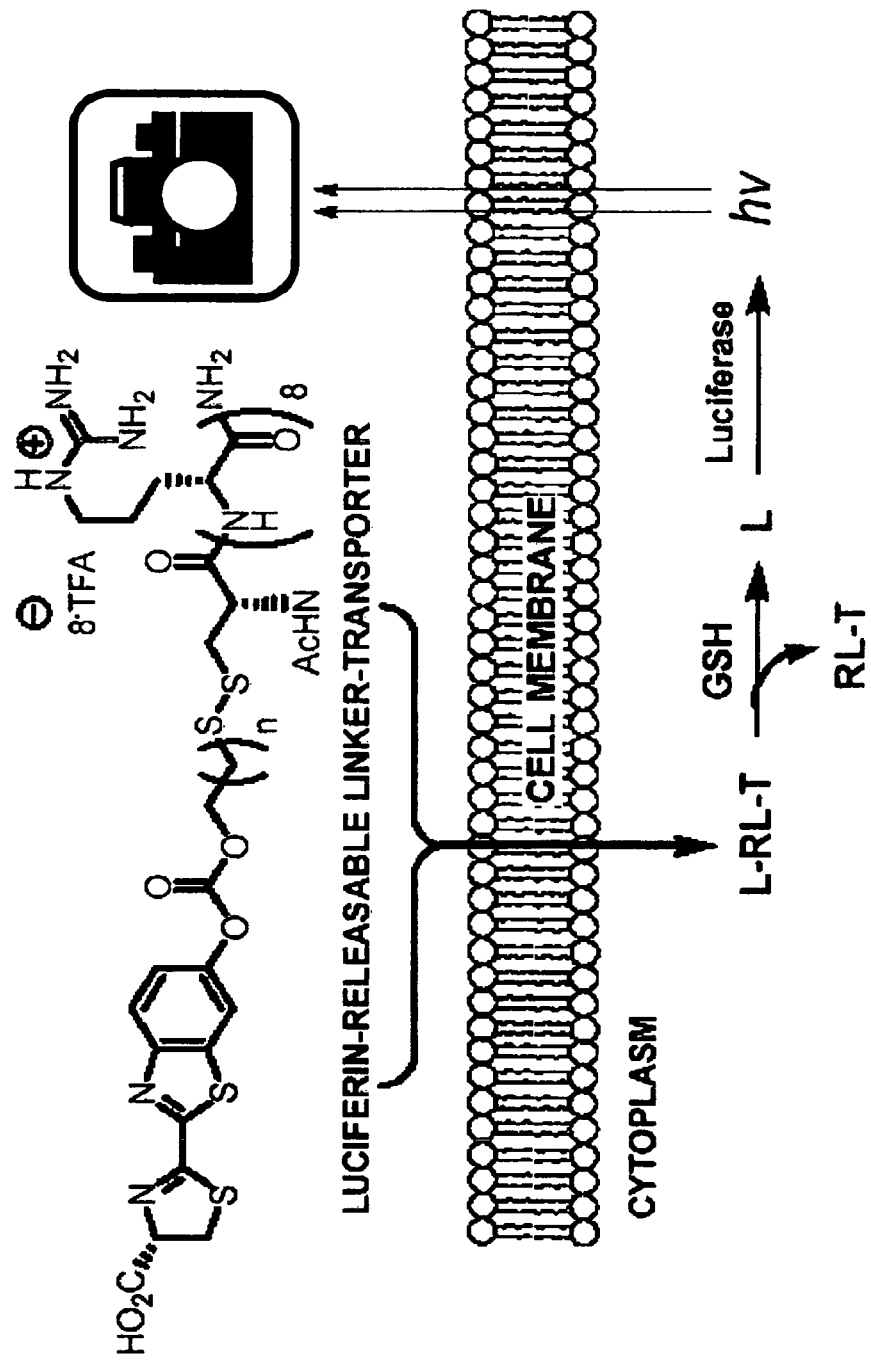
FIG. 5 depicts the proposed sequence of transport and release events for a luciferin-releasable linker-transporter conjugate embodiment. The cell has been stably transfected with a gene for luciferase. Free luciferin that is released after entry into the cell can react with luciferase and generate a photon that can be measured, allowing for real time quantification of uptake and release in cells.

The luminescent signal from cells pulsed with 5b, which is a measure of the intracellular release of free luciferin and its turnover by intracellular luciferase, increased slightly in the first few seconds and gradually decayed, reaching background after approximately 1000 seconds (FIG. 4A). Cells treated with 5c generated a different curve with less initial light, a slower rate of decay, and only two-thirds of the total photons produced when compared to that seen for 5b (FIG. 4A, FIG. 4B). To demonstrate that the observed luminescence was due to intracellular release of luciferin and its reaction with luciferase and not extracellular hydrolysis of the conjugate and luciferin uptake, the experiment was repeated in HEPES buffered saline in which all sodium salts were replaced with equimolar amounts of the potassium salt (K+HBS), a condition known to eliminate the membrane potential and thereby the uptake of arginine rich transporters but not the uptake of free luciferin (Rothbard et al., J. Am. Chem. Soc. 126:9506 (2004)). Under these conditions, luminescence from the conjugate (and therefore uptake and release) was reduced by >>90% (FIG. 4A, FIG. 4B) whereas luminescence from luciferin itself increased slightly (FIG. 4B). Consequently, the vast majority of the light arises from conjugate uptake into the cells and subsequent release of luciferin.

Example 7

Mouse Assays for Luciferin Release from Conjugates

A transgenic animal expressing firefly luciferase (FVB-luc+) was created using standard methods of pronuclear injection (Cao Y A et al. Transplant 80:134-139 (2005)) and used here to evaluate the delivery of releasable luciferin conjugates across the skin. The transgene comprised of a hybrid CMV-chicken-β-actin promoter, a modified coding sequence based on the firefly luciferase gene (present in the pGL3 vector from Promega Corp. Madison, Wis.), a FMDV 2A ribosomal slippage site and GFP gene. The animals first described by Cao Y A et al., Proc Natl Acad Sci USA 101: 221-226 (2004) were shown to express luciferase in most cell types (not expressed in erythroid cells) and exhibit GFP expression in the skin but not in many other tissues. See Cao Y A et al. Transplant 80:134-139 (2005). All procedures were approved by the Animal Care and Use Committee of Stanford University.

For imaging assays to assess skin transport, hair was removed from the animals by clipping with a large hair clipper on the right flank. Subsequently, Nair® (NAIR is a registered trademark of Church & Dwight Co., Inc., Princeton N.J., USA for a depilatory cream) was applied for 90 seconds, wiped off, and the animals were washed well with wet paper towels and dried. Five days were allowed for stratum corneum regrowth before the mice were used for imaging.

For intradermal injection of luciferin, a 2 mM solution of luciferin was made by dissolving 0.62 mg in 1 mL water pH 5.5. This solution was serially diluted with HBS (pH 7.4) (1:10) to make 1 mL of 200, 20, 2, 0.2, and 0.02 µM solutions. Solutions of luciferin (100 µL), 0.02 and 0.2 µM, were injected intradermally into two different mice. Luminescence was observed, and the higher dose was shown to be sufficiently intense to be useful for the experiment. Subsequently, three other mice were injected and imaged as rapidly as possible.

For intradermal injection of conjugate, a 1 mM solution of conjugate 5b was made by dissolving 2.1 mg in 770 µL water pH 5.5. This solution was serially diluted with HBS (pH 6.9) (1:10) to make 1 mL of 200, 20, 2, 0.2, and 0.02 µM solutions. Solutions of conjugate 5b (100 µL), 0.2 µM, were injected intradermally into two different mice. Luminescence was observed, and the dose was shown to be sufficiently intense to be useful for the experiment.

Formulations for topical application of conjugates were prepared as follows. In an eppendorf tube were combined 25 µL of 200 mM NaOAc pH 6.0, 55 µL of PEG 400 with 1 mg each of conjugate 5b and conjugate 5c to produce final concentrations of 5b.8TFA of 4.93 mM, of 5c.8TFA of 4.93 mM and sodium acetate of 63 mM. Solutions (15 µL) of 5 mM 5b and 5c were topically applied in two locations on each of four mice using a standard pipette tip (1-20 µL size). Luminescence was observed over approximately 60 minutes.

In vivo bioluminescence imaging was carried out as follows. Animals were imaged in a dark chamber using a cooled CCD camera (IVIS100 Xenongen Corp.) as previously described 45 and the data were analyzed using LivingImage software (Xenogen Corp.). Data are expressed as photons/ster radian/sec for each region of interest such that the data are not dependent on camera settings, chamber geometry or integration time.

Calibration of this mouse model for intradermal delivery was conducted using free luciferin. To establish the amount of free luciferin needed for signal detection from the skin of FVB-luc+ mice and whether it is dose dependent, a known amount of free luciferin (100 µL of either a 20 nM or a 200 nM solution of luciferin in HBS (Hepes buffered saline) was injected intradermally into the flanks of mice and the resulting bioluminescence signal (photons/unit time) was measured. The total number of photons emitted was calculated by integrating the area under the curve; see FIG. 6. The pattern of luminescence as a function of time was reproducible and similar for both doses, with a steady postinjection decrease in light emission over the duration of measurement. The area under the curve for the ten-fold higher dose was almost exactly 10 times that of the lower dose, indicating at these concentrations a linear response to dose. Based on the known amount of luciferin injected and the observed luminescence, one photon of light is detected by the camera for every 400 molecules of luciferin injected.

Figure 7:
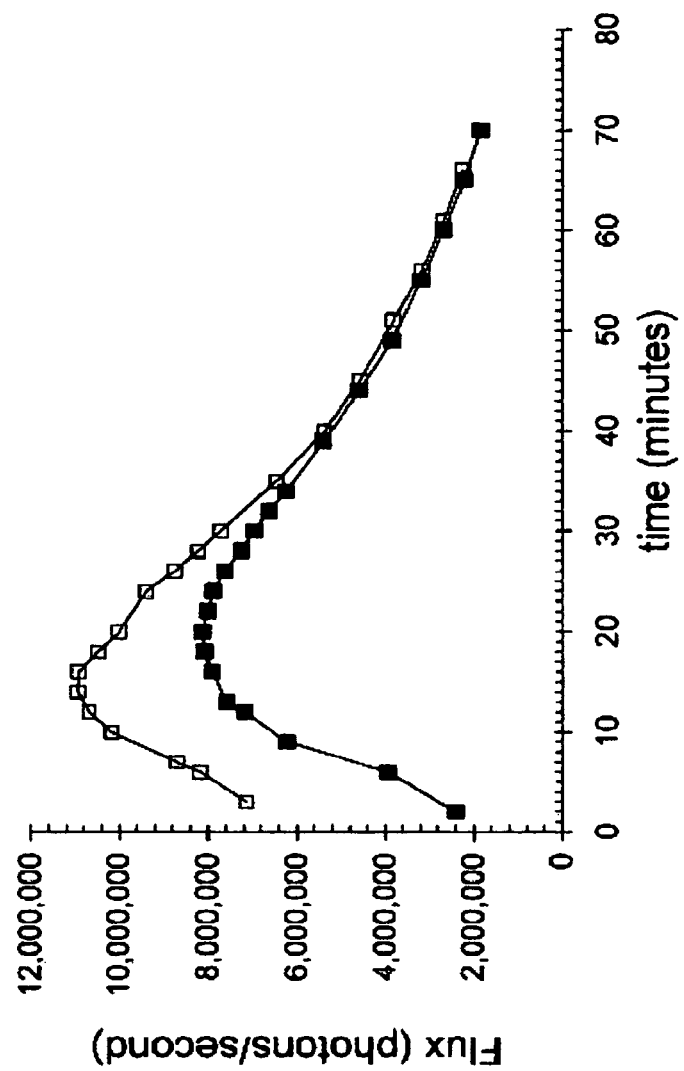
FIG. 7 depicts the resultant bioluminescence after intradermal injection of 100 uL of 200 nM conjugate 5b in HBS pH 7.4 into luciferase transgenic (FVB-luc+) mice. The pattern of luminescence is shown for two different animals. The areas under the curve are 2.54 and $2.01 \times 10^{10}$ photons.

To determine the number of photons produced from a known amount of the conjugate independent of transporter mediated skin entry, the luciferin conjugate 5b was injected intradermally as described above for free luciferin. Intradermal injection of conjugate 5b generated a distinctly different temporal pattern of bioluminescence relative to that observed for free luciferin, as shown in FIG. 7. A significant signal is apparent immediately after injection, which increases for the next 20 minutes and then slowly decays over the next 50 minutes. The profile is consistent with the time dependent generation and depletion of luciferin upon cellular uptake and linker cleavage. Approximately 80% of the theoretical amount of luciferin in the injected sample of conjugate 5b was accounted for when the total number of photons emitted in 60 minutes was multiplied by the previously calculated number of 400 molecules of luciferin per photon detected.

Figure 8:
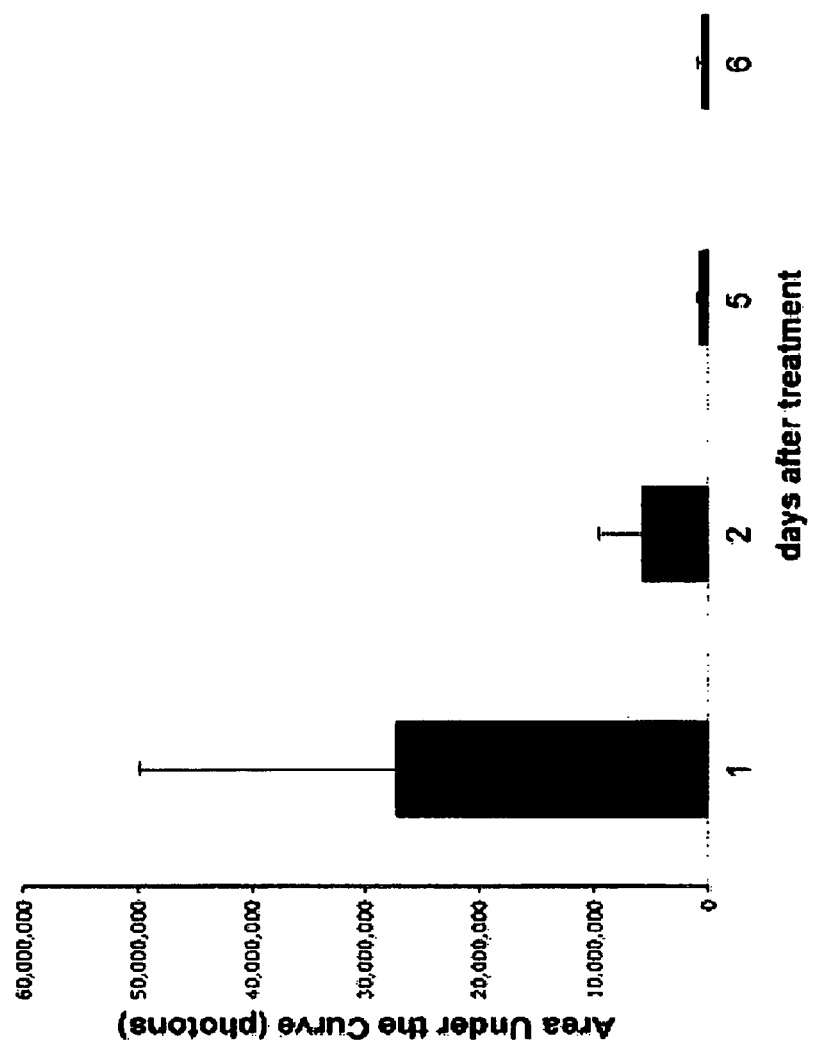
FIG. 8 depicts uptake of free luciferin into skin. Immediately after depilatory treatment, uptake is significant and variable, but is reduced with time to an insignificant level as the stratum corneum reestablishes itself. The figure displays total luminescence observed after topical application of 15 μL of 5.5 mM luciferin in 200 mM NaOAc, pH=6.0, vehicle at various time points after treatment with Nair™.

Topical Application of Luciferin Conjugates: For topical applications, the fur of the FVB-luc+ mice interferes with contact between the conjugate sample and the skin, creating reproducibility problems during administration. There were no transgenic hairless mice available and shaving alone with razors did not uniformly remove fur. Moreover, highly variable degradation of the stratum corneum, a barrier of great importance for topical applications, was observed, creating further reproducibility problems in measuring uptake. The alternative use of a depilatory (Nair®) removed fur more uniformly but also caused variable erosion of the stratum corneum, compromising the ability to reproducibly study uptake in intact skin. The observation that luciferin readily enters the skin of mice whose stratum corneum has been eroded and produces a bioluminescent signal provided the basis for a solution to this reproducibility problem. Specifically, by applying only luciferin to the skin of the transgenic mice, one can determine the integrity of the stratum corneum and, importantly, its regrowth over time. As is shown in FIG. 8, at the first time point after treatment with Nair®, a large and highly variable signal is observed. As time progresses, however, not only does the signal decrease, indicating decreasing penetration of luciferin with stratum corneum regrowth, but there is more reproducibility in the signal. From this time course study, it was determined that the optimum time to obtain a reproducible signal was five days after treatment with depilatory.

Figure 9:
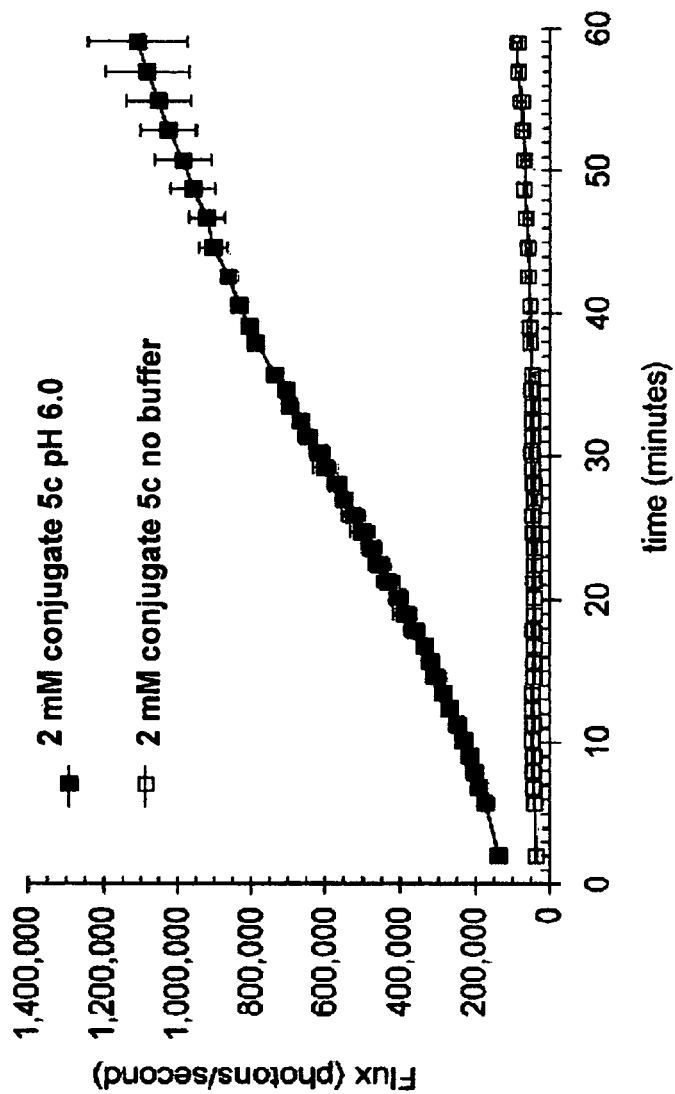
FIG. 9 depicts bioluminescence resulting from buffered and unbuffered conjugate 5c; the inherent acidity of the trifluoroacetate salt of the conjugate 5c in the unbuffered solution results in decreased bioluminescence. The figure depicts the differential bioluminescence observed when conjugate is applied in buffered (solid square) or unbuffered (open square) vehicle. Conjugate 5c (2 mM) was applied in either 25% water/75% PEG 400 or 25% 200 mM NaOAc pH=6.0/75% PEG 400.

The next step was to determine the best vehicle for topical application of the conjugates. Solutions of 5 mM trifluoroacetate salts of octa-D-arginine luciferin conjugates have a pH close to 2.0. The importance of including a buffer was tested by topically applying 15 μL of a 5 mM solution of 5c either in 25% water, or buffered with 25% 200 mM NaOAc pH 6.0, and combining with 75% PEG 400 (FIG. 9). There was a dramatic difference in the amount of light produced, with a steadily increasing amount of luminescence being observed only when the conjugate was applied in the buffered vehicle. The lack of light in the absence of buffer could arise from the acidification of the skin by the conjugate, which would decrease both the activity of luciferase and the rate of release of luciferin. These results establish the need to include an appropriate buffer in the vehicle.

Figure 10:
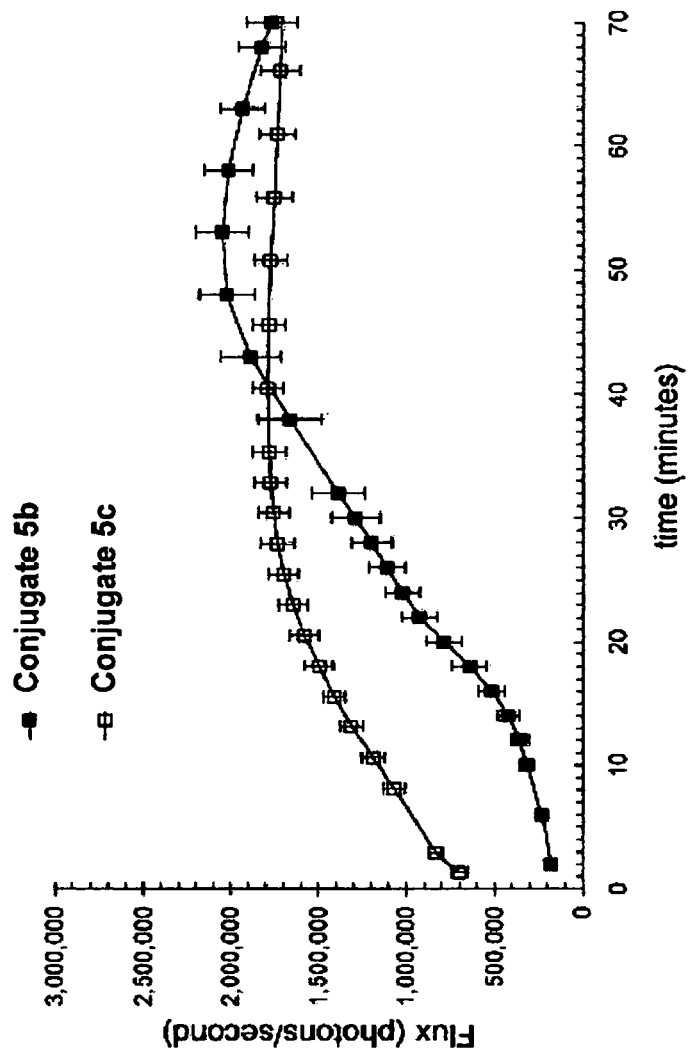
FIG. 10 depicts observed bioluminescence from luciferase transgenic mice as a function of time after topical application of 15 μL of 5 mM conjugates 5b (solid squares) and 5c (open squares) in 75% PEG 400/25% 200 mM NaOAc pH=6.0.

With the identification of an appropriate vehicle for application, a procedure for reproducibly obtaining an intact, fur-free stratum corneum, and calibrations based on intradermal injections of luciferin and of a luciferin conjugate, the uptake and release of luciferin from two topically administered, disulfide linked conjugates of luciferin and octa-D-arginine were investigated. The most reproducible method to evaluate the relative performance of transporters and linkers was to apply a single drop of a solution of each conjugate to the flank of anesthetized FVB-luc+ mice. The drop was allowed to remain in contact with the skin for the duration of the assay during which luminescence from the animal was monitored. In selected experiments the wash sample containing the residual contents of the administered drop was examined by analytical HPLC and the conjugate was found to be fully intact. The administration experiments were designed for reproducibility, for comparative quantification of different conjugates and release systems, and to conserve camera time and not to achieve optimum therapeutic levels. However, as would be expected, greater uptake can be achieved by increasing the dose, exposure time or area of application or by repeated applications. As is shown in FIG. 10, both conjugates generated a strong and reproducible luminescence signal. The difference between the observed signal and the amount of conjugate entering the skin represents the non-productive fates of the conjugate (e.g., incomplete uptake, incomplete cleavage, clearance from the skin, metabolism). Based on the intradermal calibration, the total amount of luciferin released in one hour can be determined by multiplying the area under the curve by 400 molecules/detected photon. Dividing by Avogadro's number indicates that the amount of luciferin released is $3.62 \times 10^{-12}$ mol for carbonate 5b and $2.0 \times 10^{-11}$ mol for carbonate 5c. From the area of application and the thickness of mouse skin (0.69 mm), the cumulative intradermal concentrations resulting from skin exposure over one hour are 47 nM and 62 nM, respectively. The amount of light generated is linearly proportional to the amount of conjugate applied within the range of 0.5 to 4.5 mM (data not shown), affording intradermal concentrations as high as 299 nM.

To determine whether release of luciferin might occur during administration and contact with the skin surface, it was necessary to show that the light observed was solely due to transport and intracellular release versus decomposition and release of extracellular luciferin. Toward this end, after each exposure period, the material remaining on the skin was removed from the mouse by washing and analyzed by analytical HPLC to detect any free luciferin in the wash. In each assay shown there was no free luciferin observed. Another control was to test a conjugate that is composed of an inefficient transporter with the exact same releasable linker and luciferin cargo. Lysine tetramers are known to be poor transporters for skin entry. Therefore a conjugate of a lysine tetramer 5d was synthesized and used as a comparison.

Conjugate 5d was prepared as follows:

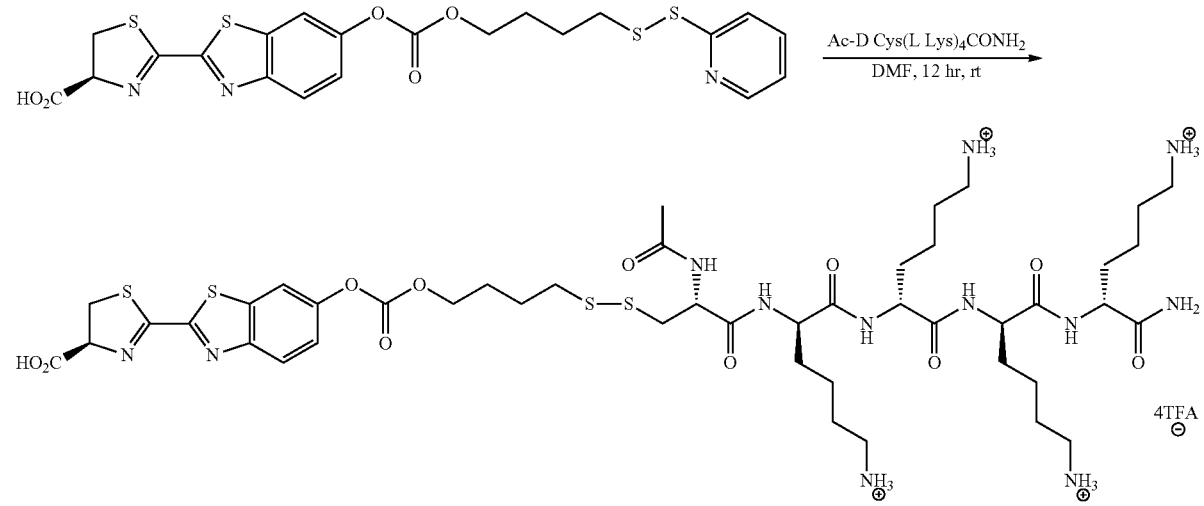

To an oven dried test tube under nitrogen equipped with a stir bar was added Ac-D Cys(L Lys)$_4$CONH$_2$.4TFA (9.7 mg, 8.61 μmol) in dry DMF (1 mL). To this was added 4c (4.5 mg, 8.61 μmol) in 0.5 mL DMF. The reaction was allowed to stir for 12 hours then purified by RP-HPLC. Appropriate fractions were lyophilized to afford a white solid (8.1 mg, 5.25 μmol, 61% yield) which was >99% pure by analytical HPLC. $^1$HNMR (500 MHz, CDJOD): δ8.16 (d, 1H, J=9.0 Hz), 7.99 (d, 1H, J=2.0 Hz), 7.46 (dd, 1H, J1 =9.0 Hz, J2=2.0 Hz), 5.46 (t, 1H, J=9.0 Hz), 4.58 (m, 1H), 4.31-4.36 (m, 6H), 3.81 (dd, 2H, J=9.0 Hz), 3.18 (m, 2H), 2.95-2.97 (m, 10H), 2.83 (m, 2H), 2.05 (s, 3H), 1.85-1.89 (m, 8H), 1.67-1.75 (m, 12H), 1.47-1.52 (m, 8H) ppm. MS (m/z): [M+2] calculated for [C$_{45}$H$_{74}$N$_{12}$O$_{11}$S$_4$] 1086.5. found (MALDI) 1086.5. Ac-D Cys(L Lys)$_4$CONH$_2$.4TFA was synthesized using general procedure for automated peptide synthesis. The peptide was assembled on Fmoc-Rink Amide Resin on a 0.1 mmol scale with all amino acids used in 1 0-fold excess (1 mmol). The identity of the peptide was established using Matrix Assisted Laser Desorption Ionization Time of Flight (MALDI-TOF) mass spectrometric analysis. MS (m/z):[M+2] calculated for [C$_{29}$H$_{60}$N$_{10}$O$_6$S] 676.4. found (MALDI) 676.5.

Figure 11:
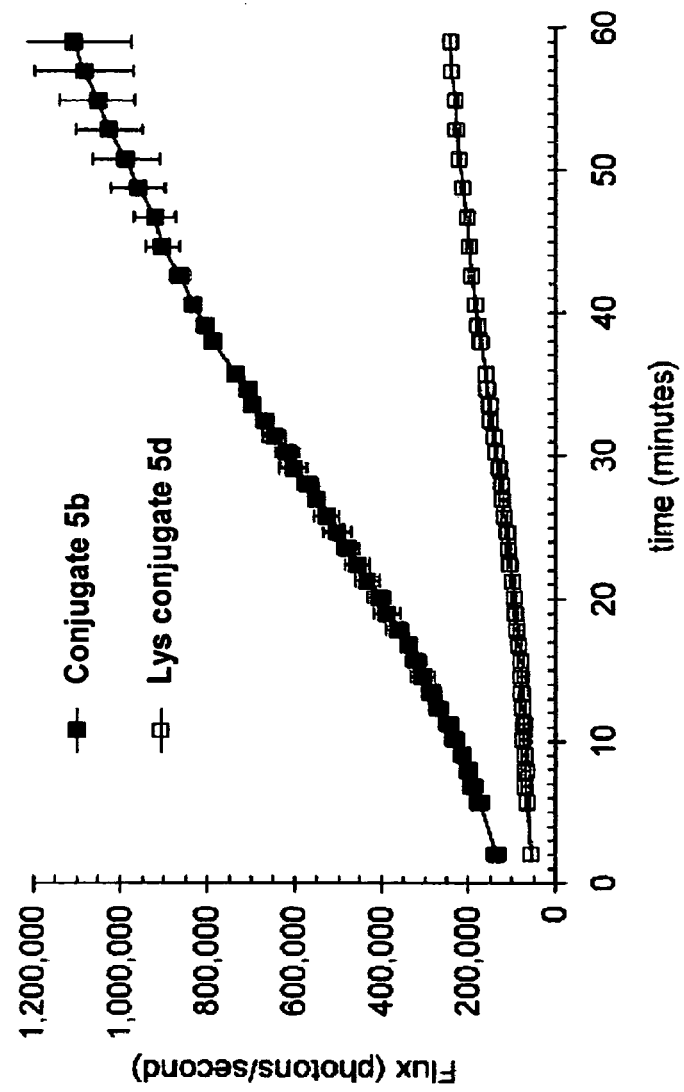
FIG. 11 depicts observed bioluminescence from luciferase transgenic mice as a function of time after topical application of 15 μL of 2 mM conjugate 5c (solid squares) and lysine conjugate 5d (open squares) in 75% PEG 400/25% 200 mM NaOAc pH=6.0.

When this less effective transporter conjugate 5d is compared to the corresponding (Arg)$_8$ conjugate 5b in the mouse assay, as shown in FIG. 11, there is much less light, thus establishing that luminescence results primarily from the intracellular release, not external hydrolysis of the prodrug.

Example 8

Taxol-Linker-Transporter Conjugates

This example demonstrates that the in vitro therapeutic index of taxol in several different ovarian cancer models (OVCA429/429T/429TP, OVCA433/433T/433TP, UCI-101), as well as its solubility in water, can be improved by conjugation of an octaarginine transporter using the linker of the current invention to C2' and C7 positions of taxol. These conjugates were also shown to have significant in vitro anti-tumor activity in cells resistant to taxol (OVCA429T/429TP, and OVCA433T/433TP), suggesting that these conjugates are able to circumvent the multidrug resistance (MDR) phenotype. Cell line OVCA 429 is sensitive to Taxol, whereas OVCA 429 T is resistant to Taxol due to overexpression of p-glycoprotein (PGP), and OVCA 429 TP is resistant to Taxol due to an unknown mechanism.

The conjugates were synthesized as follows:

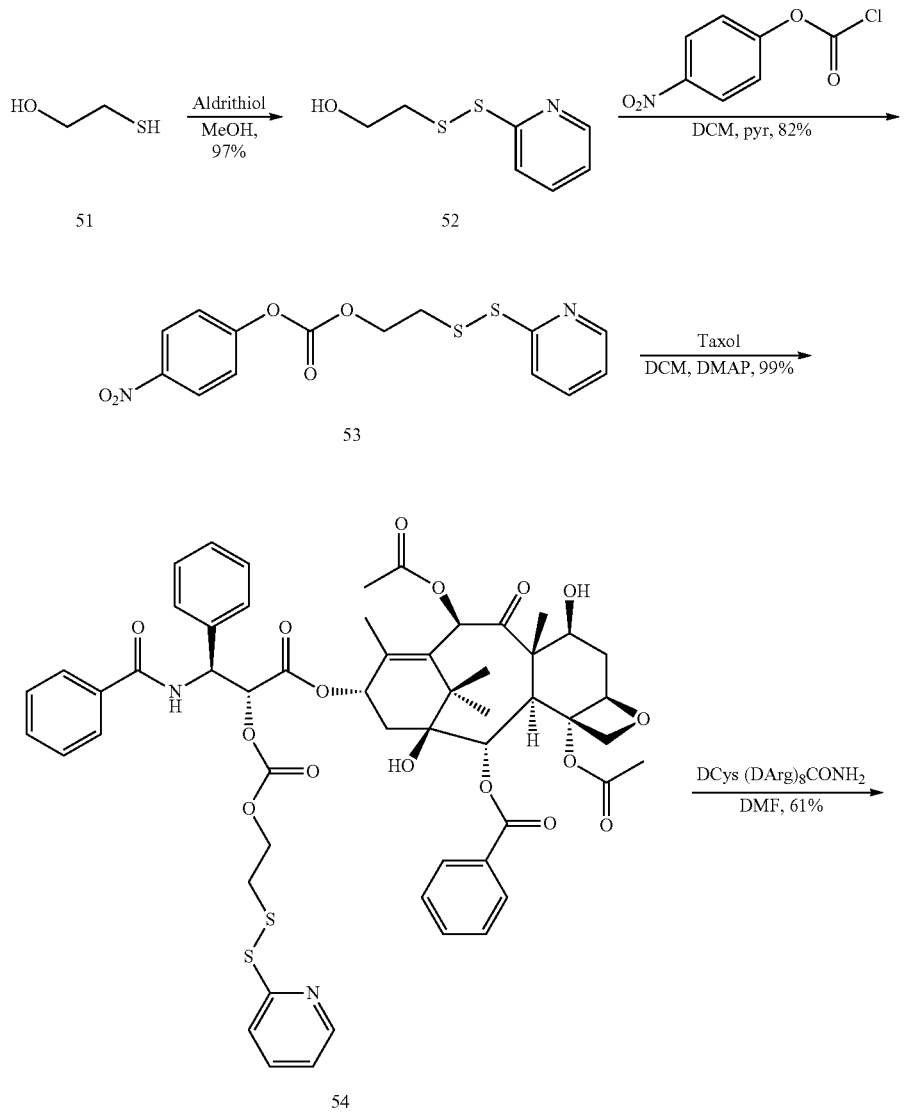

-continued
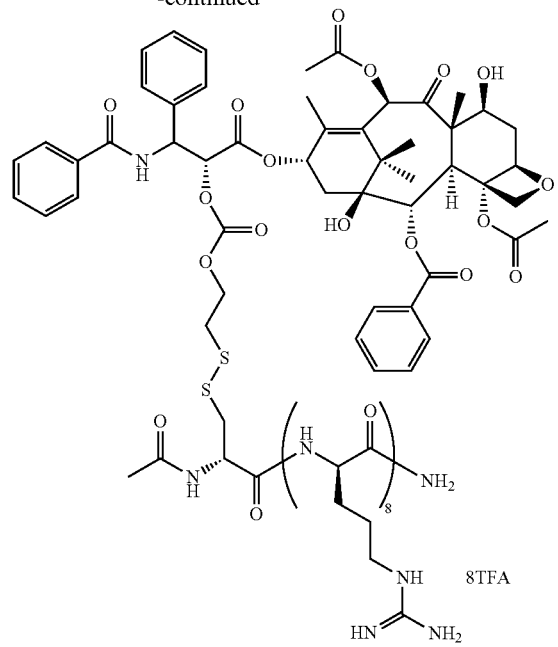
55
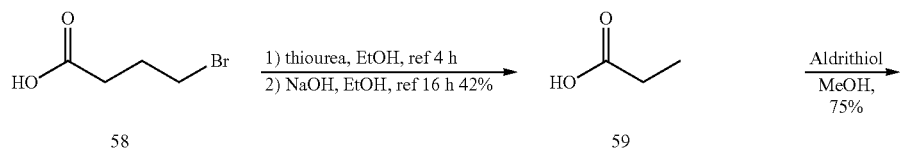
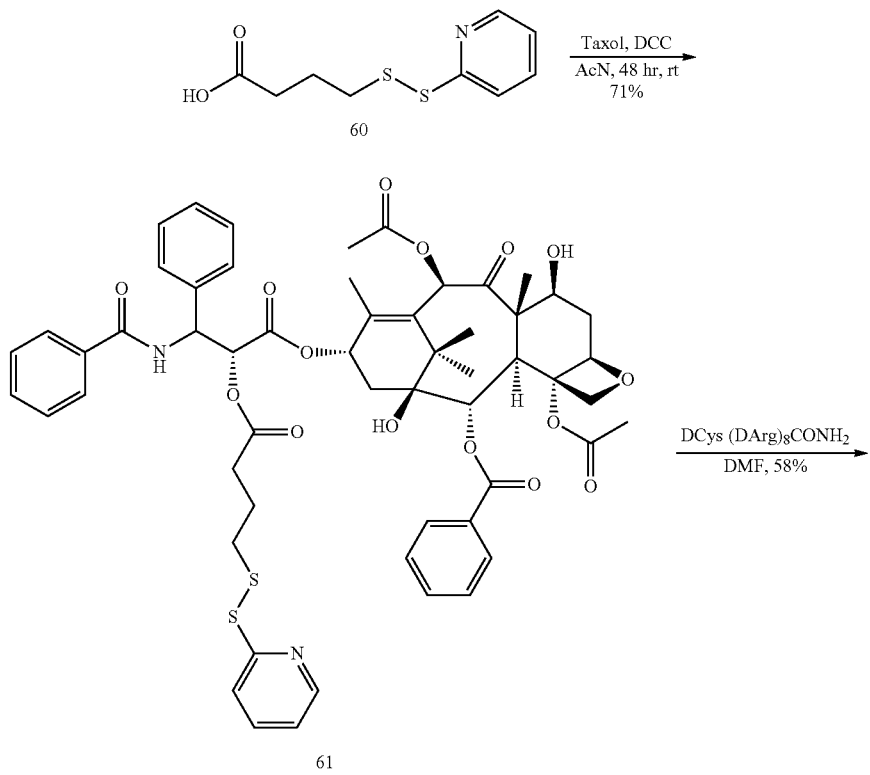

-continued
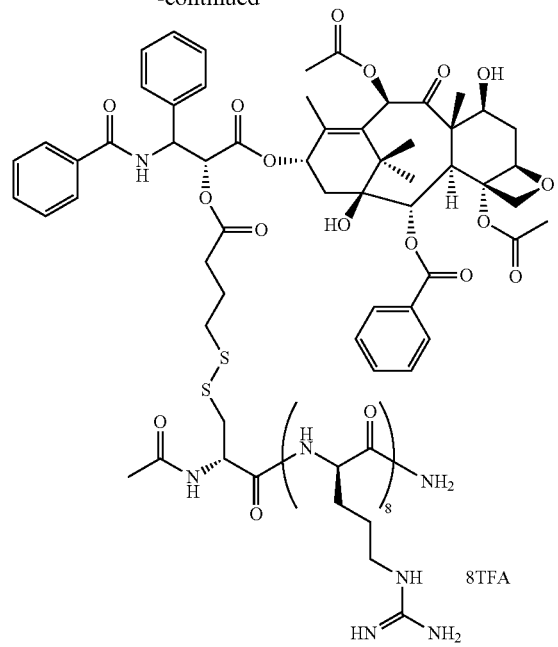
62
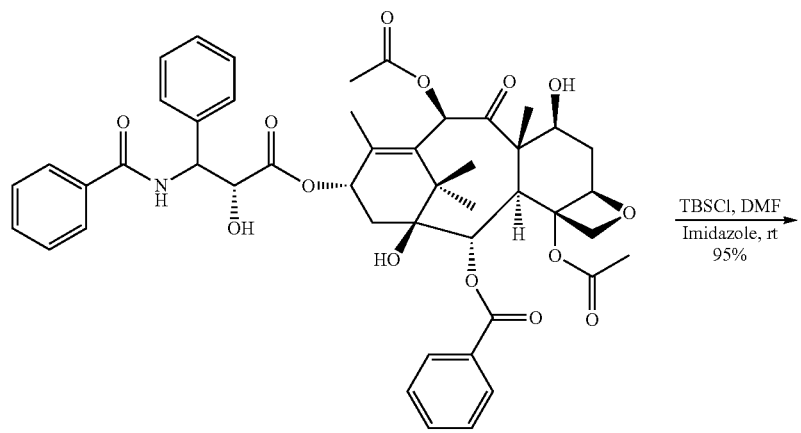
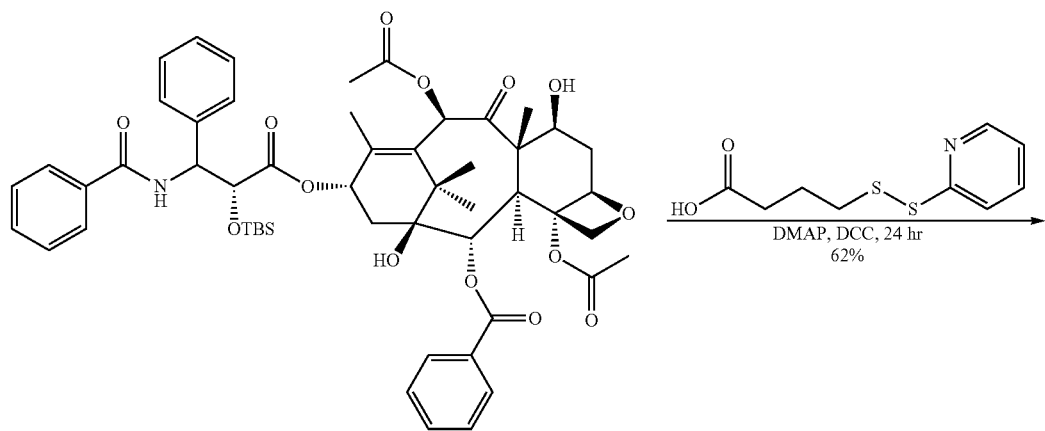
64

-continued
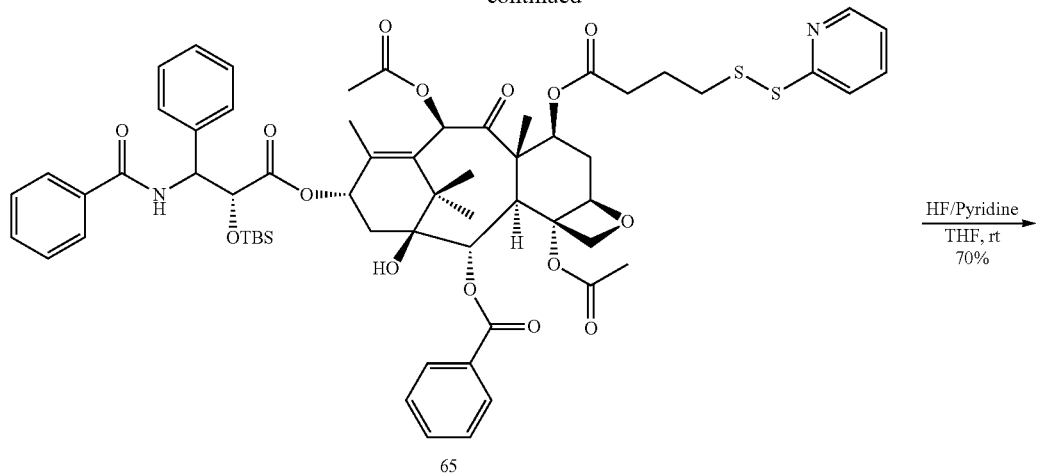
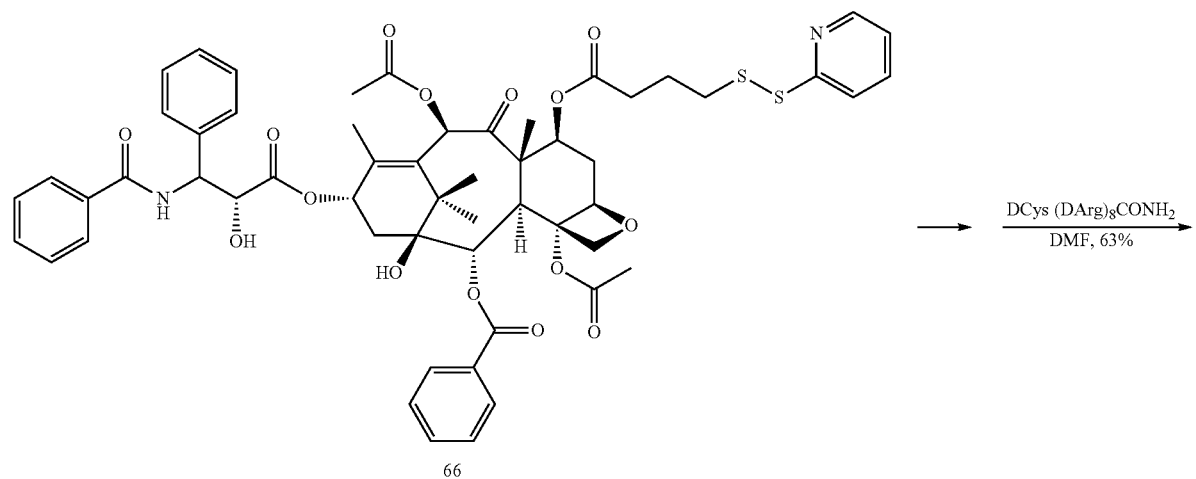
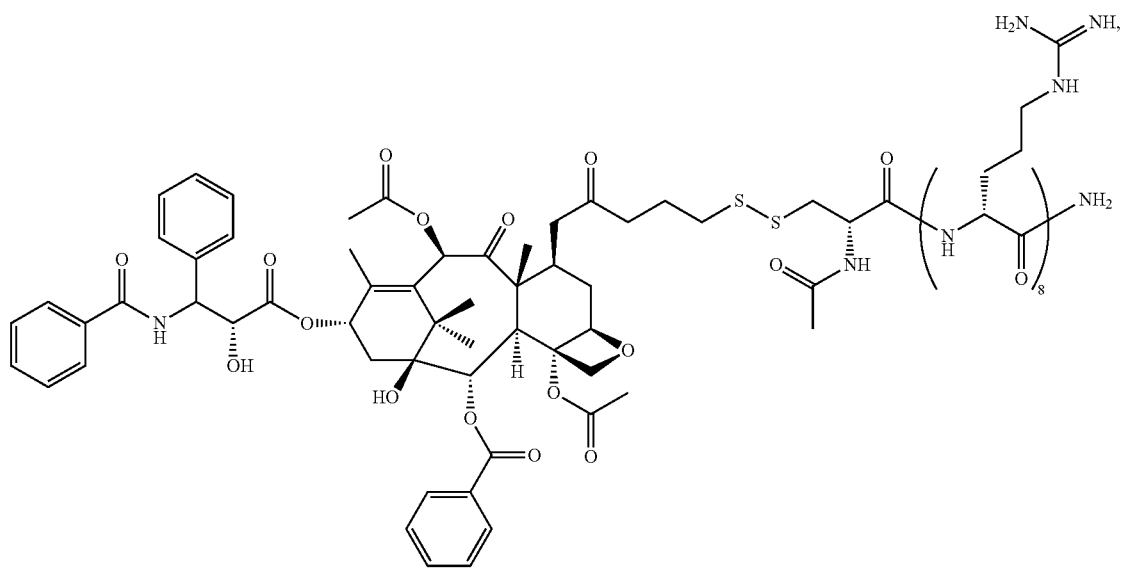

Unless otherwise stated, all reagents and solvents were obtained from commercial sources and used without purification. All reagents for peptide synthesis including NMP, DIEA, DMF, HOBT, HBTU, and piperidine were purchased from Aldrich, NovaBiochem (CA), BaChem (CA), or Applied Biosystems (CA). Fmoc-protected amino acids and resins were purchased from NovaBachem or BaChem in their appropriately protected form. All automated peptide syntheses were performed on a PE Biosystems Model 433A automated peptide synthesizer using the standard FastMoc coupling strategy. Reverse-phase high performance liquid chromatography (RP-HPLC) was performed with a Varian ProStar 210/215 HPLC using a preparative column (Alltec Alltima C18, 250×22 mm) or on an Agilent 1100 analytical HPLC with an analytical column (Vydak C18, 150×4.6 mm). The products were eluted utilizing a solvent gradient (solvent A=0.1% TFA/$H_2O$; solvent B=0.1% TFA/$CH_3CN$). NMR spectra were measured on a Varian INOVA 500 ($^1H$ NMR at 500 MHz; $^{13}C$ NMR at 125 MHz) magnetic resonance spectrometer. Data for $^1H$ NMR spectra are reported as follows: chemical shift, multiplicity (s=singlet, d=doublet, dd=doublet of doublet, t=triplet, q=quartet, and m=multiplet), integration, and coupling constant (Hz). Data for $^1H$ NMR spectra are reported in terms of chemical shift relative to residual solvent peak ($CD_3OD$: 4.97 ppm for $^1H$ NMR spectra). Matrix Assisted Laser Desorption mass spectra (MALDI) were recorded on an Applied Biosystems Voyager DE mass spectrometer.

p-Nitrophenyl Carbonate 53.

p-Nitrophenylchloroformate was reacted with alcohol 52 (see Jones, L. R. et al., *J. Am. Chem. Soc.* 2006, 128, 6526-6527) according to the procedure described by Anderson, G. W. and McGregor, A. C., *J. Am. Chem. Soc.* 1957, 79, 6180-6183, to afford carbonate 53 in 82% yield. $^1H$ NMR (500 MHz, $CD_3OD$): δ=8.47 (m, 1H), 8.24 (dd, $J_1$=7.0 Hz, $J_2$=2.0 Hz 2H), 7.74-7.66 (m, 2H), 7.36 (dd, $J_1$=7.0 Hz, $J_2$=2.0 Hz 2H), 7.14 (m, 1H), 4.54 (t, J=6.0 Hz, 2H), 3.15 (t, J=6.0 Hz, 2H) ppm. $^{13}C$ NMR (125 MHz, $CD_3Cl_3$): δ=159.3, 155.6, 152.5, 149.8, 145.6, 137.8, 125.6, 122.1, 121.6, 120.6, 66.9, 37.0 ppm. EI-MS (m/z): [M+1] calculated for [$C_{14}H_{13}N_2O_5S_2$] 353.02 found 353.0.

Taxol C2' Carbonate 54.

The synthesis of a C2' carbonate linker was based on the work of de Groot, F. M. H. et al., *J. Med. Chem.* 2000, 43, 3093-3102 in which p-nitrophenyl carbonate 53 was reacted with C2' position of Taxol to afford C2' carbonate 54 in almost quantitative yield (99%). $^1H$ NMR (500 MHz, $CD_3OD$): δ=8.39 (m, 1H), 8.14 (d, J=7.6 Hz, 2H), 7.85-7.47 (m, 11H), 7.31 (m, 1H), 7.20 (m, 1H), 6.47 (s, 1H), 6.11 (t, J=8.5 Hz, 1H), 5.88 (d, J=6.0 Hz, 1H), 5.48 (d, J=6.5 Hz, 1H), 4.43 (m, 2H), 4.37 (m, 1H), 4.20 (m, 1H), 3.83 (d, 7.5 Hz, 1H), 3.12 (t, J=6.0 Hz, 2H), 2.51 (m, 2H), 2.44 (s, 3H), 2.44-2.20 (m, 4H), 1.91 (s, 3H), 1.83 (m, 2H), 1.68 (s, 3H), 1.17 (s, 3H), 1.16 (s, 3H) ppm. $^{13}C$ NMR (100 MHz, $CDCl_3$): δ=203.5, 170.9, 169.5, 167.4, 166.7, 158.8, 153.5, 149.5, 142.3, 136.8, 136.3, 133.4, 133.1, 132.5, 132.1, 131.7, 130.5, 129.9, 128.8, 128.5, 128.4, 128.2, 126.8, 126.3, 120.7, 119.6, 84.1, 80.7, 78.8, 75.2, 74.7, 71.8, 67.8, 66.1, 58.2, 52.4, 45.2, 42.8, 38.3, 36.2, 35.2, 30.0, 28.6, 26.5, 23.4, 22.6, 22.4, 21.8, 20.5, 14.5, 13.7, 10.6, 9.3 ppm. MS (m/z): [M+1] calculated for [$C_{55}H_{59}N_2O_{16}S_2$] 1067.3; found (MALDI) 1067.5.

Taxol C2' Octaarginine Conjugate 55.

Carbonate 54 was further coupled with Ac—NH-DCys (DArg)$_8$CONH$_2$ (Kirschberg, T. A. et al, *Org. Lett.* 2003, 5, 3459-3462) using the procedure of Jones et al. (Jones, L. R. et al., *J. Am. Chem. Soc.* 2006, 128, 6526-6527) to afford the final conjugate in 61% yield. $^1H$ NMR (500 MHz, $D_2O$): δ=7.99 (d, J=7.3 Hz, 2H), 7.75-7.50 (m, 6H), 7.44-7.39 (m, 6H), 7.15 (m, 1H), 6.33 (s, 1H), 5.91 (t, J=8.5 Hz, 1H), 5.59 (d, J=7.9 Hz, 1H), 5.47 (m, 2H), 5.05 (d, J=8.7 Hz, 1H), 4.42 (t, J=7.0 Hz, 1H), 4.26-4.14 (m, 11H), 3.79 (t, J=6.0 Hz, 2H), 3.63 (d, J=7.0 Hz, 1H), 3.08 (m, 18H), 2.98-2.84 (m, 2H), 2.88 (t, J=6.0 Hz, 2H), 2.43 (m, 1H), 2.29 (s, 3H), 2.15 (s, 3H), 1.87 (s, 3H), 1.80 (s, 3H), 1.79-1.52 (m, 38H), 1.05 (s, 3H), 1.00 (s, 3H). MS (m/z): [M+2] calculated for [$C_{103}H_{161}N_{35}O_{26}S_2$] 2368.2; found (MALDI) 2368.1.

Taxol C2' Tetraarginine Conjugate.

This compound was coupled with Ac—NH-DCys (DArg)$_4$CONH$_2$ using the procedure of Jones et al. (Jones, L. R. et al., *J. Am. Chem. Soc.* 2006, 128, 6526-6527) in 55% yield. $^1H$ NMR (500 MHz, $D_2O$): δ=8.05 (d, J=7.3 Hz, 2H), 7.72-7.47 (m, 6H), 7.40-7.37 (m, 6H), 7.14 (m, 1H), 6.33 (s, 1H), 5.92 (t, J=8.5 Hz, 1H), 5.60 (d, J=7.9 Hz, 1H), 5.47 (m, 2H), 5.03 (d, J=8.7 Hz, 1H), 4.42 (t, J=7.0 Hz, 1H), 4.22-4.15 (m, 7H), 3.79 (t, J=6.0 Hz, 2H), 3.65 (d, J=7.0 Hz, 1H), 3.08 (m, 10H), 2.98-2.84 (m, 2H), 2.88 (t, J=6.0 Hz, 2H), 2.45 (m, 1H), 2.29 (s, 3H), 2.13 (s, 3H), 1.87 (s, 3H), 1.81 (s, 3H), 1.81-1.51 (m, 21H), 1.08 (s, 3H), 1.03 (s, 3H). MS (m/z): [M+1] calculated for [$C_{79}H_{112}N_{19}O_{22}S_2$] 1742.8, found (MALDI) 1742.9.

4-(Pyridin-2-Yldisulfanyl)-Butyric Acid (60).

Acid 60 was synthesized from free thiol 59 (see Blount, K. F. and Uhlenbeck, O. C., *Biochemistry,* 2002, 41, 6834-6841) as described by Jones, L. R. et al., *J. Am. Chem. Soc.* 2006, 128, 6526-6527. $^1H$ NMR (500 MHz, $CDCl_3$): δ 8.50 (d, 1H, J=4.5 Hz), 7.74 (d, 1H, J=8.0 Hz), 7.68 (t, 1H, J=8.0 Hz), 7.13 (t, 1H, J=7.0 Hz), 2.87 (t, 2H, J=7.0 Hz), 2.52 (t, 2H, J=7.0 Hz), 2.06 (m, 2H), ppm. $^{13}C$ NMR (125 MHz, $CDCl_3$): δ=178.1, 159.9, 149.4, 137.3, 120.8, 119.9, 37.7, 32.3, 23.7. EI-MS (m/z): [M+1] calculated for [$C_9H_{12}NO_2S_2$] 230.02; found 230.0.

Taxol C2' Ester 61.

The procedure published by Rodrigues and coworkers (Rodrigues, M. L. et al., *Chem Biol.* 1995, 2, 223-227) was used for the coupling of acid 60 with Taxol to afford compound 61 in 71% yield. $^1H$ NMR (500 MHz, $CDCl_3$): δ=8.46 (m, 1H), 8.16 (d, J=7.6 Hz, 2H), 7.78 (d, J=7.6 Hz, 2H), 7.69-7.35 (m, 13H), 7.11 (m, 1H) 6.99 (d, J=9.0 Hz, 1H), 6.32 (s, 1H), 6.28 (t, J=9.0 Hz, 1H), 5.99 (dd, $J_1$=9.1 Hz, $J_2$=3.2 Hz, 1H), 5.71 (d, J=7.0 Hz, 1H), 5.54 (d, J=2.2 Hz, 1H), 4.99 (d, J=9.0 Hz, 1H), 4.48 (dd, $J_1$=11.0 Hz, $J_2$=6.8 Hz, 1H)), 4.33 (d, J=8.5 Hz, 1H), 4.21 (d, J=8.5 Hz, 1H), 3.84 (d, J=7.0 Hz, 1H), 2.84-2.77 (m, 2H), 2.66-2.55 (m, 2H), 2.47 (s, 3H), 2.38 (m, 1H), 2.25 (s, 3H), 2.20 (m, 1H), 2.05 (m, 3H), 1.91 (m, 4H), 1.78 (m, 1H), 1.71 (s, 3H), 1.25 (s, 3H), 1.16 (s, 3H) ppm. $^{13}C$ NMR (125 MHz, $CDCl_3$): δ=204.1, 172.1, 171.5, 170.1, 168.3, 167.5, 167.3, 149.1, 145.0, 143.0, 138.3, 137.1, 134.0, 133.7, 133.0, 132.4, 130.6, 130.5, 129.8, 129.4, 129.0, 128.8, 128.3, 128.2, 128.1, 127.4, 126.8, 121.4, 120.8, 84.7, 81.3, 79.4, 75.9, 75.3, 74.3, 72.4, 72.1, 58.8, 53.0, 45.9, 43.4, 37.5, 35.8, 32.2, 27.1, 24.0, 23.0, 22.4, 21.1, 15.1, 9.9 ppm. MS (m/z): [M+2] calculated for [$C_{56}H_{62}N_2O_{15}S_2$] 1066.3; found (MALDI) 1066.7.

Taxol C2' Octaarginine Conjugate 62.

This compound was coupled with Ac—NH-DCys (DArg)$_8$CONH$_2$ (Kirschberg, T. A. et al., *Org. Lett.* 2003, 5, 3459-3462) using the procedure of Jones et al. (Jones, L. R. et al., *J. Am. Chem. Soc.* 2006, 128, 6526-6527) in 58% yield. $^1H$ NMR (500 MHz, $CD_3OD$): δ=8.14 (d, J=7.5 Hz, 2H), 7.85 (d, J=7.5 Hz, 2H), 7.72 (m, 1H), 7.59 (m, 3H), 7.48 (m, 6H), 7.28 (m, 1H), 6.46 (s, 1H), 6.03 (t, J=8.5 Hz, 1H), 5.80 (d, J=7.0 Hz, 1H), 5.65 (d, J=7.0 Hz, 1H), 5.49 (m, 1H), 5.03 (d, J=9.5 Hz, 1H), 4.88 (s, 1H), 4.54 (m, 1H), 4.35-4.26 (m, 10H), 4.20 (m, 2H), 3.81 (d, J=7.0 Hz, 1H), 3.22 (m, 17H), 3.14 (m, 1H), 2.98 (m, 1H), 2.77 (t, J=7.0 Hz, 2H), 2.61 (m, 2H), 2.49 (m, 1H), 2.40 (s, 3H), 2.20 (s, 3H), 2.14-2.03 (m, 6H), 1.94-1.87 (m, 43H), 1.17 (s, 3H), 1.14 (s, 3H) ppm. MS (m/z): [M+1] calculated for [$C_{104}H_{162}N_{35}O_{25}S_2$] 2365.2; found (MALDI) 2365.8.

Taxol C2' Tetrarginine Conjugate.

This compound was coupled with Ac—NH-DCys (DArg)$_4$CONH$_2$ using the procedure of Jones et al. (Jones, L. R. et al., J. Am. Chem. Soc. 2006, 128, 6526-6527) in 58% yield. $^1$H NMR (500 MHz, CD$_3$OD): δ=8.14 (d, J=7.5 Hz, 2H), 7.86 (d, J=7.5 Hz, 2H), 7.72 (m, 1H), 7.61 (m, 3H), 7.49 (m, 6H), 7.30 (m, 1H), 6.46 (s, 1H), 6.01 (t, J=8.5 Hz, 1H), 5.82 (d, J=7.0 Hz, 1H), 5.67 (d, J=7.0 Hz, 1H), 5.49 (m, 1H), 5.04 (d, J=9.5 Hz, 1H), 4.88 (s, 1H), 4.53 (m, 1H), 4.36-4.27 (m, 6H), 4.20 (m, 2H), 3.81 (d, J=7.0 Hz, 1H), 3.22 (m, 9H), 3.14 (m, 1H), 2.98 (m, 1H), 2.77 (t, J=7.0 Hz, 2H), 2.61 (m, 2H), 2.49 (m, 1H), 2.40 (s, 3H), 2.21 (s, 3H), 2.11-2.03 (m, 6H), 1.95-1.86 (m, 27H), 1.17 (s, 3H), 1.14 (s, 3H) ppm. MS (m/z): [M+1] calculated for [$C_{80}H_{114}N_{19}O_{21}S_2$] 1740.8; found (MALDI) 1741.5.

Taxol C2' TBS Ester 64.

Synthesis of C2' TBS protected Taxol 64 has been described by Magri, N. F. et al., J. Nat. Prod. 1988, 51, 298-306, and their procedure has been followed precisely to afford TBS C2'ester 64 in 95% yield. All spectra were in agreement with the published data of Magri et al.

Taxol C7 Ester 65.

Formation of ester 65 at C7 position has been done according to the procedure described by Damen and coworkers (Damen, E. W. P. et al., Bioorg. Med. Chem. 2000, 8, 427-432) to afford the desired ester 65 in 62% yield. $^1$H NMR (500 MHz, CDCl$_3$): 8.44 (m, 1H), 8.12 (d, J=10.5 Hz, 2H), 7.73 (m, 3H), 7.61 (m, 2H), 7.49 (m, 3H), 7.42-7.31 (m, 6H), 7.07 (m, 2H), 6.25 (m, 2H), 5.73-5.68 (m, 2H), 5.59 (m, 1H), 4.95 (d, J=11.5 Hz, 2H), 4.66 (s, 1H), 4.33 (d, J=10.5 Hz, 1H), 4.19 (d, J=10.5 Hz, 1H), 4.11 (m, 2H), 3.95 (d, J=8.5 Hz, 1H), 2.83 (t, J=8.0 Hz, 2H), 2.56 (s, 3H), 2.78 (m, 4H), 2.14 (s, 3H), 2.03 (s, 3H), 1.97 (s, 3H), 1.79 (m, 6H), 1.26-1.15 (m, 10H), 0.79 (s, 9H), −0.03 (s, 3H), −0.31 (s, 3H). $^{13}$C NMR (125 MHz, CDCl$_3$) δ 202.2, 172.2, 171.7, 170.1, 169.2, 167.2, 160.7, 149.9, 141.2, 138.5, 137.3, 134.3, 134.0, 132.9, 132.1, 130.5, 129.3, 129.1, 129.0, 128.2, 127.3, 126.6, 120.8, 119.8, 84.2, 81.2, 78.9, 76.7, 75.4, 75.3, 74.7, 71.6, 56.3, 55.9, 47.1, 43.6, 38.3, 35.8, 33.6, 32.7, 29.9, 26.6, 25.8, 23.8, 23.3, 21.7, 21.0, 18.4, 14.9, 11.2, 1.3, −4.9, −5.6. MS (m/z): [M+2] calculated for [$C_{62}H_{76}N_2O_{15}S_2Si$] 1180.4. found (MALDI) 1180.1.

Taxol C7 Ester 66.

TBS deprotection of C2' ester to afford compound 66 in 70% yield was done using the procedure of Kirschberg, T. A. et al., Org. Lett. 2003, 5, 3459-3462. $^1$H NMR (500 MHz, CDCl$_3$): 8.44 (m, 1H), 8.12 (d, J=10.5 Hz, 2H), 7.73 (m, 3H), 7.61 (m, 2H), 7.49 (m, 3H), 7.42-7.31 (m, 6H), 7.20 (d, J=9.0 Hz, 1H), 7.08 (m, 1H) 6.21 (m, 2H), 5.81 (d, J=9.0 Hz, 1H), 5.68 (d, J=7.0 Hz, 1H), 5.55 (m, 1H), 4.95 (d, J=11.5 Hz, 2H), 4.81 (s, 1H), 4.33 (d, J=10.5 Hz, 1H), 4.19 (d, J=10.5 Hz, 1H), 4.11 (m, 2H), 3.95 (m, 2H), 2.84 (t, J=8.0 Hz, 2H), 2.54-2.43 (m, 3H), 2.38 (s, 3H), 2.34 (m, 2H), 2.17 (s, 3H), 2.05-1.95 (m, 4H), 1.82 (s, 3H), 1.80 (s, 3H), 1.78 (m, 1H), 1.97 (s, 3H), 1.27 (m, 1H), 1.21 (s, 3H), 1.17 (s, 3H) ppm. $^{13}$C NMR (125 MHz, CDCl$_3$): δ=202.2, 172.7, 172.2, 170.6, 169.2, 167.3, 167.1, 160.6, 149.8, 140.7, 138.3, 137.3, 134.1, 133.9, 133.2, 130.4, 129.3, 129.2, 129.0, 128.9, 128.5, 127.3, 120.8, 199.9, 84.1, 81.2. 78.7, 76.7, 75.5, 74.5, 73.5, 72.3, 71.7, 56.4, 55.2, 47.2, 43.5, 38.2, 35.8, 33.7, 32.7, 26.8, 23.8, 22.8, 21.1, 21.0, 14.9, 11.1 ppm. MS (m/z): [M+Na] calculated for [$C_{56}H_{60}N_2O_{15}S_2Na$] 1087.3 found (MALDI) 1087.4.

Taxol C7 Octaarginine Conjugate 67.

Taxol C7 ester 16 was coupled with Ac—NH-DCys (DArg)$_8$CONH$_2$ (Kirschberg, T. A. et al., Org. Lett. 2003, 5, 3459-3462) using the procedure of Jones et al. (Jones, L. R. et al., J. Am. Chem. Soc. 2006, 128, 6526-6527) to afford the desired product in 63% yield. $^1$H NMR (500 MHz, CD$_3$OD): δ=8.14 (d, J=7.5 Hz, 2H), 7.88 (d, J=7.5 Hz, 2H), 7.71 (m, 1H), 7.59 (m, 3H), 7.48 (m, 6H), 7.32 (m, 1H), 6.27 (s, 1H), 6.17 (t, J=8.5 Hz, 1H), 5.67 (m, 2H), 5.61 (m, 1H), 5.04 ((d, J=9.5 Hz, 1H), 4.89 (s, 1H), 4.78 (d, J=5.5 Hz, 1H), 4.52 ((t, J=7.0 Hz, 1H), 4.35-4.21 (m, 10H), 3.93 (d, J=7.0 Hz, 1H), 3.23 (m, 17H), 3.05 (m, 1H), 2.76 (t, J=7.0 Hz, 2H), 2.55 (m, 1H), 2.41 (m, 5H), 2.28 (m, 1H), 2.18 (s, 3H), 2.08 (s, 3H), 2.03-1.65 (m, 45H), 1.18 (s, 3H), 1.14 (s, 3H) ppm. MS (m/z): [M+Na] calculated for [$C_{104}H_{161}N_{35}O_{25}S_2Na$] 2387.2. found (MALDI) 2387.4.

Taxol C7 Tetraarginine Conjugate.

Taxol C7 ester 16 was coupled with DCys (DArg)$_4$CONH$_2$ using the procedure of Jones et al. (Jones, L. R. et al., J. Am. Chem. Soc. 2006, 128, 6526-6527) to afford the desired product in 51% yield. $^1$H NMR (500 MHz, CD$_3$OD): δ=8.15 (d, J=7.5 Hz, 2H), 7.88 (d, J=7.5 Hz, 2H), 7.72 (m, 1H), 7.59 (m, 3H), 7.48 (m, 6H), 7.32 (m, 1H), 6.26 (s, 1H), 6.15 (t, J=8.5 Hz, 1H), 5.64 (m, 2H), 5.61 (m, 1H), 5.05 (d, J=9.5 Hz, 1H), 4.89 (s, 1H), 4.78 (d, J=5.5 Hz, 1H), 4.50 (t, J=7.0 Hz, 1H), 4.33-4.18 (m, 6H), 3.93 (d, J=7.0 Hz, 1H), 3.30 (m, 9H), 3.03 (m, 1H), 2.77 (t, J=7.0 Hz, 2H), 2.55 (m, 1H), 2.41 (m, 5H), 2.28 (m, 1H), 2.18 (s, 3H), 2.08 (s, 3H), 2.15-1.76 (m, 29H), 1.19 (s, 3H), 1.15 (s, 3H) ppm. MS (m/z): [M+Na] calculated for [$C_{80}H_{113}N_{19}O_{21}S_2Na$] 1762.8. found (MALDI) 1763.3.

Figure 12:
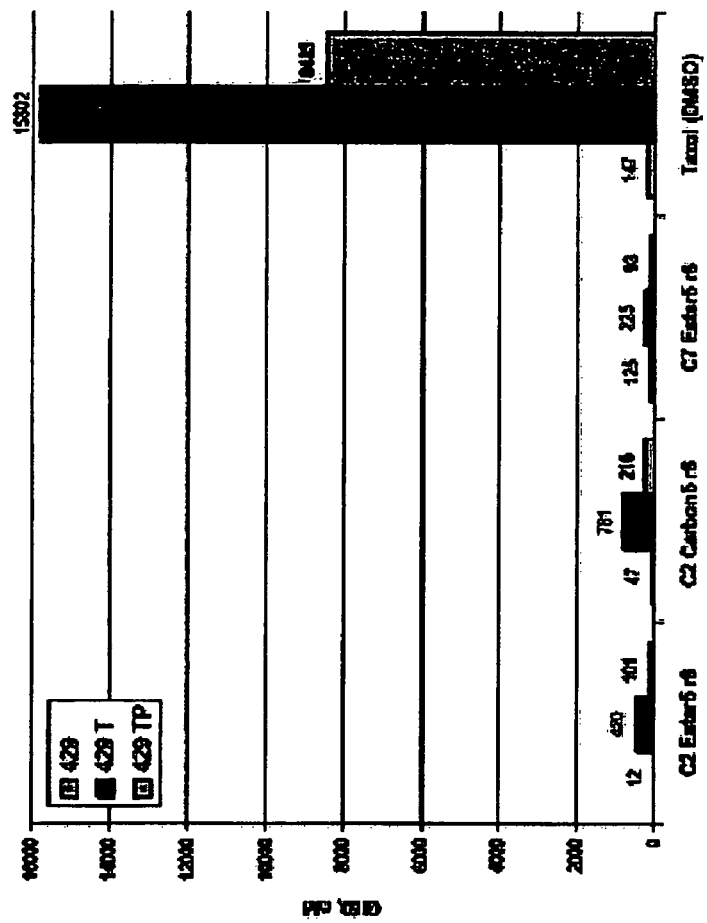
FIG. 12 depicts an assay for $GI_{50}$ (nM) of 429 Ovarian Cancer Lines, 20 min pulse with indicated compounds. The cells were pulsed for 20 min, washed (×2) and incubated for 72 hr in fresh media. For each compound, three bars are depicted, for 429 cells, 429 T cells, and 429 TP cells (from left to right). $GI_{50}$ values in nM are: for first group of bars labelled "C2 Ester5 r8" (compound 62), 12 (429), 420 (429T), 101 (429TP); "C2 carbon5 r8" (compound 55), 47 (429), 781 (429T), 216 (429TP); "C7 Ester5 r8" (compound 67), 125 (429), 225 (429T), 93 (429TP); taxol (in DMSO), 147 (429), 15802 (429T), 8485 (429TP).

The results of the cell growth inhibition assay (GI$_{50}$) in OVCA429/429T/429TP human ovarian cancer cell lines are shown in FIG. 12. The cells were pulsed with conjugates administered in PBS (pH=7.4) and Taxol (administered in DMSO) for 20 min. Then the solution was removed, the cells were washed twice and incubated in fresh media for 72 hr. The presence of live cells were measured based on the standard MTS assay. As can be seen, the conjugates inhibited growth of cancer cells even in Taxol-resistant cell lines, whereas Taxol showed lower activity by orders of magnitude in resistant cell lines 429T and 429TP.

Example 9

Cyclosporin-Linker-Transporter Conjugates

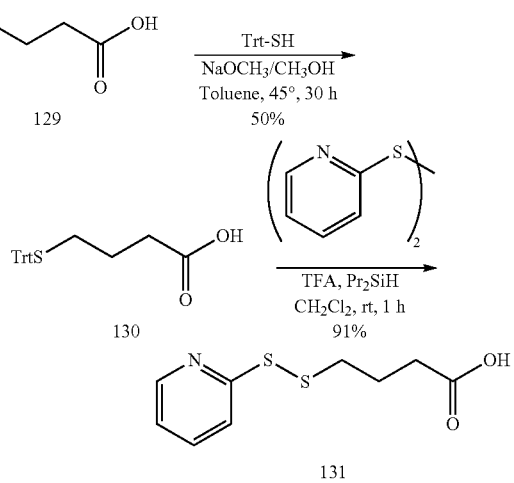

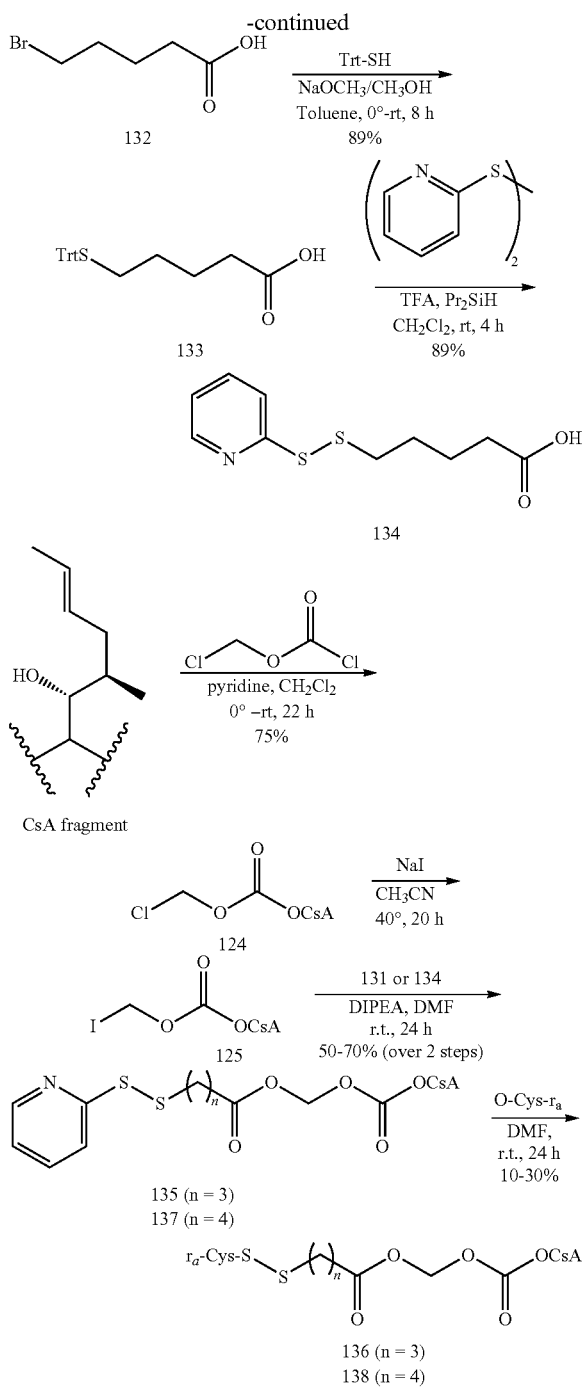

over MgSO$_4$, filtered, and concentrated in vacuo. The crude product was purified via silica gel chromatography (pentane-ethyl acetate, gradient from 1:1 to 1:3) to give 404.0 mg (75%) of pure 24: $^1$H-NMR (500 MHz, CDCl$_3$): δ 8.56 (1H, d, J=10 Hz), 8.00 (1H, d, J=7.5 Hz), 7.50 (1H, d, J=9 Hz), 7.46 (1H, d, J=7.5 Hz), 5.66 (1H dd, J=11.5, 4.3 Hz), 5.58 (1H, d, J=3.5 Hz), 5.37 (1H, dd, J=12, 3.8 Hz), 5.26 (2H, m, J=nd), 5.14 (2H, m, J=nd), 4.94 (1H, q, J=8 Hz), 4.83 (1H, t, J=8 Hz), 4.82 (1H, d, J=11 Hz), 4.74 (1H, t, J=10 Hz), 4.64 (1H, d, J=14.5 Hz), 4.40 (1H, quintet, J=7 Hz), 4.18 (1H, d, J=14.5 Hz), 3.94 (1H, d, J=14.5 Hz), 3.45 (3H, s), 3.24 (3H, s), 3.23 (3H, s), 3.19 (3H, s), 3.14 (1H, d, J=11 Hz), 2.65 (3H, s), 2.63 (3H, s), 2.42 (1H, m, J=nd), 2.15 (4H, m, J=nd), 1.93 (4H, m, J=nd), 1.67 (6H, m, J=nd), 1.58 (3H, d, J=6.5 Hz), 1.42 (2H, m, J=nd), 1.32 (1H, m, J=nd), 1.29 (3H, d, J=7 Hz), 1.25 (3H, d, J=7 Hz), 1.16 (1H, dq, J=15, 10.5, 4 Hz), 1.05 (3H, d, J=7 Hz), 1.04 (3H, d, J=7 Hz), 1.01 (3H, d, J=7 Hz), 0.98 (3H, d, J=6.5 Hz), 0.94 (3H, d, J=7 Hz), 0.93 (3H, d, J=7 Hz), 0.89 (3H, d, J=7.5 Hz), 0.88 (3H, d, J=7.5 Hz), 0.86 (3H, d, J=7.5 Hz), 0.84 (9H, m, J=nd), 0.79 (3H, d, J=8 Hz), 0.76 (3H, d, J=7 Hz).

Iodomethylcarbonate-CsA (125).

To an oven-dried roundbottom flask purged with N$_2$ was added a solution of 124 (239.5 mg, 0.185 mmol) in dry CH$_2$Cl$_2$ (800 μL). The solvent was blown down under a stream of N$_2$ and then further concentrated in vacuo. The dry residue was brought up in dry CH$_3$CN (1.8 mL) to give a slightly cloudy solution. Then solid NaI (166.3 mg, 1.11 mmol) was added at room temp. The resulting yellow, clear solution was heated to 40° C. in an oil bath and allowed to stir for 20 hours. The brown solution was concentrated in vacuo, brought up in ethyl acetate (20 mL), washed successively with 10% aq. Na$_2$S$_2$O$_5$ (20 mL×2) and saturated aq. NaCl (20 mL×1), dried over MgSO$_4$, filtered, and concentrated in vacuo. The crude product was not further purified or characterized. It was taken directly into the next reaction.

4-Tritylthio-Butyric Acid (130).

To an oven-dried test tube purged with N$_2$ was added trityl mercaptan (1.203 g, 4.35 mmol). The solid was dissolved in dry toluene (3 mL) and stirred with a magnetic stirbar before the addition of a 25% solution of sodium methoxide in methanol (2.17 mL, 9.58 mmol) via syringe. The solution was cooled to 0° C. in an ice/water bath, then a solution of 4-bromobutyric acid (800.0 mg, 4.79 mmol) in MeOH (1 mL) was added. The solution changed to a tan color and was allowed to warm to room temp and stir for 6 hours. It was then heated to 40° C. in an oil bath. The color changed from a yellowish hue to deep orange after 24 hours of reaction time. After 24 hours, an additional equivalent of 4-bromobutyric acid was added. After an additional hour of stirring, more sodium methoxide in methanol solution was added (500 μL). The reaction was allowed to stir for a total of 30 hours, after which it was concentrated in vacuo, brought up in distilled H$_2$O (30 mL) and 1M H$_2$SO$_4$ (10 mL), extracted with ethyl acetate (40 mL×3), dried over MgSO$_4$, filtered, and concentrated in vacuo. The resulting yellow oil was purified via silica gel chromatography (pentane-ethyl acetate-acetic acid, gradient from 84:15:1 to 64:35:1) to give 873.6 mg (50.3%) of pure 130: $^1$H-NMR (400 MHz, CDCl$_3$): δ 7.47 (6H, d, J=8.5 Hz), 7.32 (6H, t, J=7.2 Hz), 7.24 (3H, 7.2 Hz), 2.36 (2H, t, J=7.2 Hz), 2.28 (2H, t, J=7.2 Hz), 1.72 (2H, quintet, J=7.2 Hz).

4-Pyridyidithio-Butyric Acid (131).

To a flame-dried 10 mL roundbottom flask purged with N$_2$ was added a solution of 130 (436.8 mg, 1.205 mmol) in dry CH$_2$Cl$_2$ (10 mL). To this was added 4-aldrithiol (796.4 mg, 3.615 mmol) via weigh paper and then triisopropylsilane (272.3 μL, 1.325 mmol) via microsyringe. Trifluoroacetic acid (~2.5 mL) was added dropwise under stirring at room temp until the bright yellow color persisted. The reaction was allowed to stir for 1 hour, after which it was concentrated in vacuo and purified via silica gel chromatography (pentane-ethyl acetate-acetic acid, gradient from 69:30:1 to 54:45:1) to give 251.6 mg (91%) of pure 131: $^1$H-NMR (500 MHz, CDCl$_3$): δ 8.52 (1H, d, J=4.8 Hz), 7.79 (1H, d, J=8 Hz), 7.74 (1H, t, J=7.5 Hz), 7.18 (1H, t, J=6.5 Hz), 2.84 (2H, t, J=7.5 Hz), 2.47 (2H, t, J=7.5 Hz), 2.01 (2H, quintet, J=7.5 Hz).

5-Tritylthio-Valeric Acid (133).

To a flame-dried roundbottom flask purged with N$_2$ was added trityl mercaptan (347 mg, 1.26 mmol). The solid was dissolved in dry toluene (5.5 mL) and stirred with a magnetic stirbar before the addition of a 25% solution of sodium methoxide in methanol (860 µL, 3.77 mmol) via syringe. The solution was cooled to 0° C. in an ice/water bath, then a solution of 5-bromovaleric acid (250.0 mg, 1.38 mmol) in MeOH (3 mL) was added. The solution changed to a light brown color and was allowed to warm to room temp and stir for 8 hours, after which it was concentrated in vacuo, brought up in distilled H$_2$O (30 mL) and 1M aq. H$_2$SO$_4$ (10 mL), extracted with ethyl acetate (40 mL×3), dried over MgSO$_4$, filtered, and concentrated in vacuo. The resulting yellow solid was purified via silica gel chromatography (pentane-ethyl acetate-acetic acid, gradient from 69:30:1 to 64:35:1) to give 419.8 mg (88.5%) of pure 133: $^1$H-NMR (500 MHz, CDCl$_3$): δ 7.48 (6H, d, J=8.5 Hz), 7.33 (6H, t, J=8 Hz), 7.26 (3H, 8 Hz), 2.26 (2H, t, J=7.5 Hz), 2.23 (2H, t, J=7.5 Hz), 1.64 (2H, quintet, J=7.5 Hz), 1.48 (2H, quintet, J=7.5 Hz).

5-Pyridyldithio-Valeric Acid (134).

To a flame-dried 10 mL roundbottom flask purged with N$_2$ was added a solution of 133 (248.5 mg, 0.66 mmol) in dry CH$_2$Cl$_2$ (6 mL). To this was added 4-aldrithiol (436.3 mg, 1.98 mmol) via weigh paper and then triisopropylsilane (149.2 µL, 0.726 mmol) via microsyringe. Trifluoroacetic acid (~1 mL) was added dropwise under stirring at room temp until the bright yellow color persisted. The reaction was allowed to stir for 1 hour, after which it was concentrated in vacuo and purified via silica gel chromatography (pentane-ethyl acetate-acetic acid, gradient from 64:35:1 to 44:55:1) to give 142.1 mg (88.5%) of pure 134: $^1$H-NMR (400 MHz, CDCl$_3$): δ 8.48 (1H, d, J=4.8 Hz), 7.75 (1H, d, J=8.8 Hz), 7.68 (1H, t, J=7.6 Hz), 7.11 (1H, t, J=6 Hz), 2.78 (2H, t, J=7.2 Hz), 2.33 (2H, t, J=6.8 Hz), 1.72 (4H, m, J=nd).

CsA-Carbonate-Acetal-Ester-5-Aldrithiol (135).

To a flame-dried 10 mL conical roundbottom flask was added a solution of 131 (50.0 mg, 0.218 mmol) in ethyl acetate. The solvent was evaporated in vacuo. To the dry residue at room temp was added dry DMF (750 µL) and diisopropylethylamine (45.7 µL, 0.263 mmol). The resulting solution was added to a roundbottom flask containing 125 (242.6 mg, 0.175 mmol). The reaction was stirred at room temp for 3 hours, after which it was diluted with MeOH (1.5 ml) and purified via prep HPLC (65-100% CH$_3$CN gradient over 30 minutes, column heated to 50° C.) to give 123.1 mg (47.3%) of pure 135.

CsA-Carbonate-Acetal-Ester-5-D-Arg$_8$-NH2 (136).

To an oven-dried 600 µL conical vial purged with N$_2$ was added 135 (16.13 mg, 0.0108 mmol) in dry CH$_2$Cl$_2$. The solvent was evaporated under a stream of N$_2$ and then further concentrated in vacuo. To the vial was added a solution of Ac-D-Cys-D-Arg$_8$-NH$_2$ (22.91 mg, 0.00986 mmol) in dry DMF (150 µL). Solution color turned yellow immediately. It was allowed to stir at room temp for 24 hours, after which it was diluted with MeOH and purified via prep HPLC (30-90% CH$_3$CN gradient over 30 min, column heated to 50° C.) to give 10.4 mg (28.5%) of pure 136.

CsA-Carbonate-Acetal-Ester-6-Aldrithiol (137).

To an oven-dried vial was added a solution of 134 (21.37 mg, 0.088 mmol) in dry CH$_3$CN (550 µL). Then diisopropylethylamine (17.13 µL, 0.098 mmol) was added via microsyringe. A solid crashed out, so dry DMF (80 µL) was added to solubilize it. The resulting solution was added to a dry roundbottom flask containing 125 (97.4 mg, 0.070 mmol). The reaction was stirred at room temp for 24 hours, after which it was concentrated in vacuo. The yellow residue was brought up in ethyl acetate (40 mL), washed successively with 10% aq. Na$_2$S$_2$O$_5$ (40 mL×2) and saturated aq. NaCl (40 mL×1), dried over MgSO$_4$, filtered, and concentrated in vacuo. The crude product was purified via silica gel chromatography (ethyl acetate-pentane, gradient from 91:9 to 95:5) to give 73.1 mg (69.4%) of pure 137.

CsA-Carbonate-Acetal-Ester-6-D-Arg$_8$-NH$_2$ (138).

To an oven-dried 600 µL conical vial purged with N$_2$ was added 137 (14.62 mg, 0.0097 mmol) in dry CH$_2$Cl$_2$. The solvent was evaporated under a stream of N$_2$ and then farther concentrated in vacuo. To the vial was added a solution of Ac-D-Cys-D-Arg$_8$-NH$_2$ (20.56 mg, 0.00885 mmol) in dry DMF (100 µL). Solution color turned yellow immediately. It was allowed to stir at room temp for 25 hours, after which it was diluted with MeOH and purified via prep HPLC (30-90% CH$_3$CN gradient over 20 min, column heated to 50° C.) to give 2.7 mg (8.2%) of pure 138.

Compound 136,

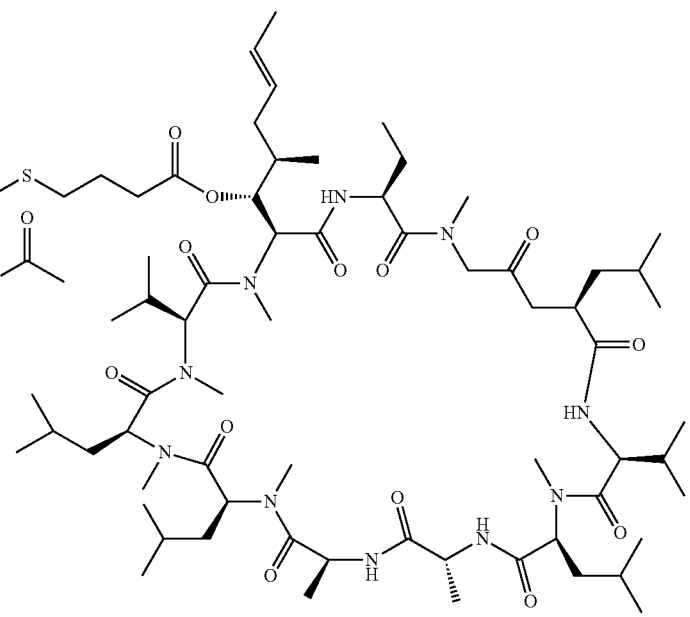

was tested as follows. BL4.IL-2 cells were incubated with varying concentrations of either CsA or conjugate 136 overnight at 37° C. to allow for uptake and release of the active form of CsA. The next day, T cells were stimulated to produce IL-2 by the addition of 10 ng/mL of phorbol 12-myristate 13 acetate and 1 µM of ionomycin. Cultures were incubated overnight at 37° C., and the next day supenatants were collected and IL-2 was measured using fluorescent enzyme-linked immunoassay (ELISA kit). Each test was done in triplicate. The IC50 of 136 was determined to be 1900 nM.

Figure 15A:
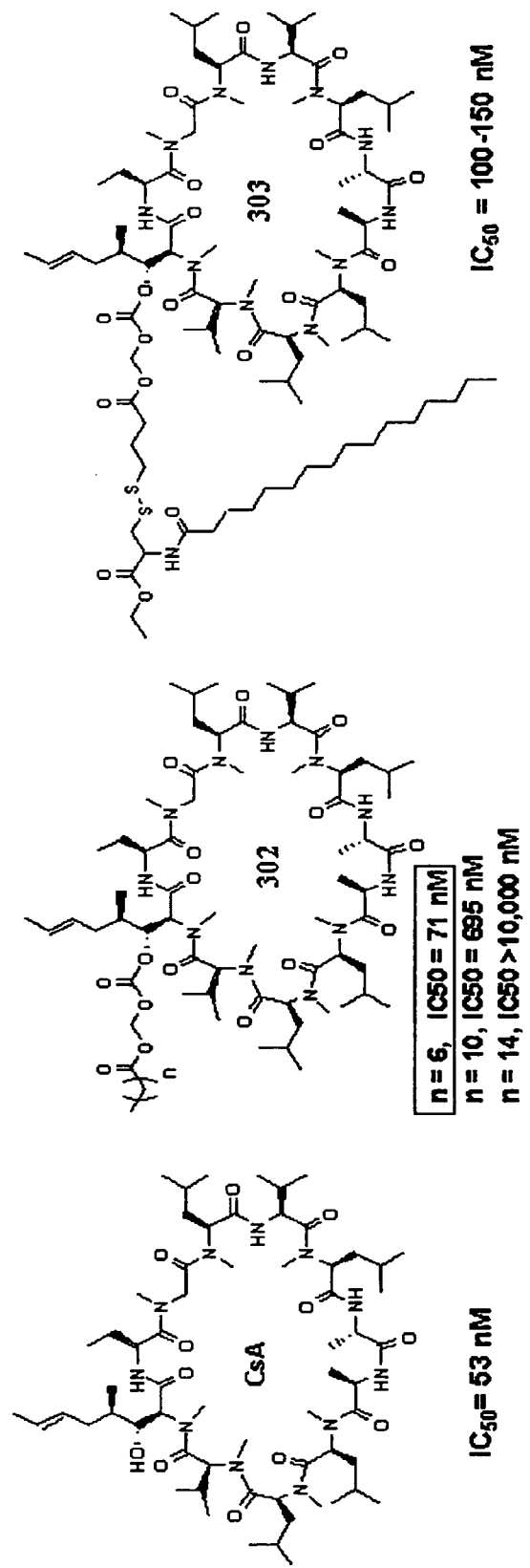
FIG. 15A and FIG. 15B depict cyclosporine A-lipid conjugates using the linkers of the invention.
Figure 15B:
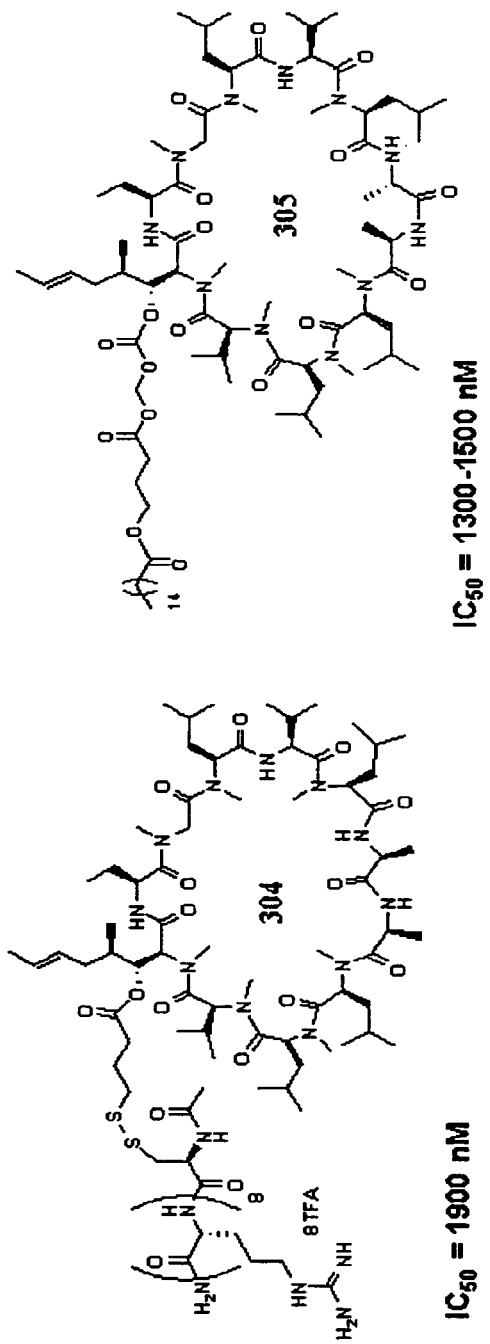

FIG. 15A and FIG. 15B depict cyclosporine A conjugated to lipids via linkers of the invention, where the lipid-cysteine-SH molecules 205 of Example 10 have been reacted with cyclosporine compounds 135 and 137 of this example, to create cyclosporine-lipid conjugates. BL4.IL-2 cells were incubated with varying concentrations of either CsA or conjugates overnight at 37° C. to allow for uptake and release of the active form of CsA. The next day, T cells were stimulated to produce IL-2 by the addition of 10 ng/mL of phorbol 12-myristate 13 acetate and 1 µM of ionomycin. Cultures were incubated overnight at 37° C., and the next day supernatants were collected and IL-2 was measured using fluorescent enzyme-linked immunoassay (ELISA kit). Each test was done in triplicate. The $IC_{50}$ values determined are listed in FIG. 15A and FIG. 15B.

Example 10

Lipid Transporters

TLC was performed with 0.25 mm silica gel 60F plates with fluorescent indicator (254 nm). Reverse-phase high performance liquid chromatography (RP-HPLC) was performed with a Varian ProStar 210/215 HPLC using a preparative column (Alltec Alltima C18, 250×22 mm) or on an Agilent 1100 analytical HPLC with an analytical column (Vydak C18, 150×4.6 mm). The products were eluted utilizing a solvent gradient (solvent A=0.1% TFA/H2O; solvent B=0.1% TFA/CH3CN). NMR spectra were measured on a Varian INOVA 500 (1H NMR at 500 MHz; 13C NMR at 125 MHz) magnetic resonance spectrometer. Data for 1H NMR spectra are reported as follows: chemical shift, multiplicity (s=singlet, d=doublet, dd=doublet of doublet, t=triplet, q=quartet, and m=multiplet), integration, and coupling constant (Hz). Data for 13C NMR spectra are reported in terms of chemical shift relative to residual solvent peak (CDCl3=77.3 ppm and CD3OD=49.1 ppm). Electrospray ionization mass spectra (ES-MS) were recorded at the mass spectrometry lab at Stanford University on a Finnigan LCQ quadrupole ion trap mass spectrometer. Matrix Assisted Laser Desorption mass spectra (MALDI) were recorded on an Applied Biosystems Voyager DE mass spectrometer.

Synthesis and Characterization of Luciferin Octa L-Arginine Conjugates 203-207a-e.

S-Trityl-L-Cysteine Ethyl Ester (203).

L-Cysteine ethyl ester hydrochloride (5.0 g, 27.03 mmol, 1 eq.) and trityl chloride (11.3 g, 40.55 mmol, 1.5 eq) were stirred in 20 mL of DMF for 2 days at room temperature. The reaction was purified by direct injection into RP-HPLC using

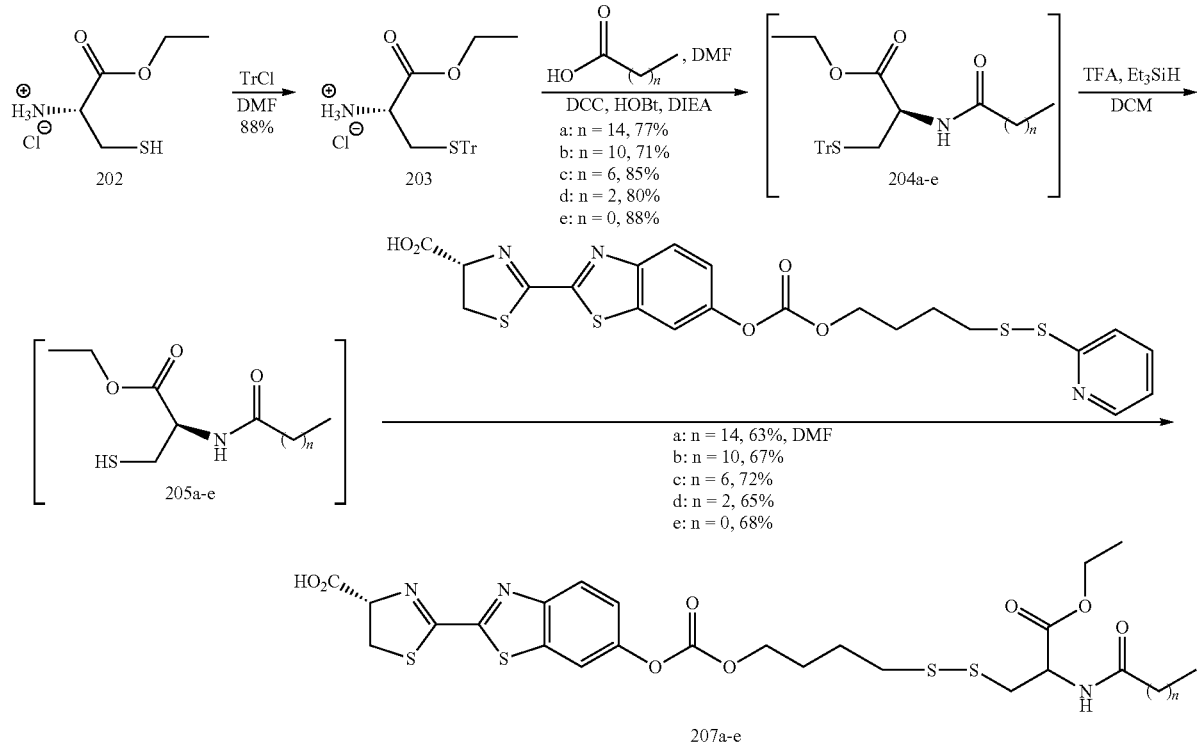

One embodiment of the lipid transporters-liner-cargo molecules using linkers of the invention can be conveniently synthesized by the method described herein. Unless otherwise stated, all reagents and solvents were obtained from commercial sources and used without purification. Analytical 50-100% water/acetonirile gradient (no TFA added) over 20 min. After drying in vacuo, 9.3 g (88%) of 203 was obtained as a white powder. 1H NMR (500 MHz, CD3OD): δ=7.23-7.41 (m, 15H), 4.18 (q, 2H, J=7.5 Hz), 3.17 (m, 1H), 2.58 (dd, 1H, J=8.5 Hz, 12 Hz), 2.48 (dd, 1H, J=5 Hz, 12 Hz), 1.35 (t, 3H, J=7.5 Hz). 13C NMR (125 MHz, CD3OD) δ 171.9, 145.9, 130.7, 129.0, 127.9, 68.1, 62.5, 53.3, 30.8, 14.3. EI-MS (m/z): [M+1] calculated for C24H27NO2S 392.2. found 393.2.

Compound 204a.

To a solution of S-Trityl-L-Cysteine ethyl ester (203) (67 mg, 0.176 mmol), palmitic acid (50 mg, 0.194 mmol), DCC (36 mg, 0.176 mmol), and HOBt (27 mg, 0.176 mmol) in 3 mL of dry DMF was added triethylamine (54 uL, 0.352 mmol) and the reaction was allowed to stir overnight at room temperature under nitrogen atmosphere. The reaction was quenched with 1% HCl aqueous solution and washed with ethyl acetate. The organic layer was dried over MgSO4, concentrated in vacuo and purified by column chromatography (EtOAc—pentane 1:5, then 1:1) to give pure 202a (85.3 mg, 77%) as an oil. 1H NMR (500 MHz, CD3OD): δ=7.41-7.23 (m, 15H), 4.20 (q, 1H, J=5 Hz), 4.08 (q, 2H, J=7.5 Hz), 2.62 (dd, 1H, J=8.5 Hz, 12 Hz), 2.56 (dd, 1H, J=5 Hz, 12 Hz), 2.28 (t, 3H, J=7.5 Hz), 1.63-1.60 (m, 2H), 1.34-1.28 (m, 24H), 1.20 (t, 3H, J=7.5 Hz), 0.91 (t, 3H, J=7 Hz). 13C NMR (125 MHz, CD3OD) δ 176.1, 171.8, 145.9, 130.7, 129.0, 127.9, 68.1, 62.5, 53.3, 36.7, 34.5, 33.1, 30.8, 30.7, 30.5, 30.4, 30.2, 27.0, 23.7, 14.5, 14.4. EI-MS (m/z): [M+1] calculated for C40H56NO3S 630.4. found 630.4.

Compound 204b.

Compound 204b was synthesized as described above for 204a using lauric acid instead of palmitic acid in 71% yield. 1H NMR (500 MHz, CD3OD): δ=7.41-7.21 (m, 15H), 4.22 (q, 1H, J=5 Hz), 4.08 (q, 2H, J=7.5 Hz), 2.64 (dd, 1H, J=8.5 Hz, 12 Hz), 2.56 (dd, 1H, J=5 Hz, 12 Hz), 2.22 (t, 2H, J=7 Hz), 1.64-1.61 (m, 2H), 1.35-1.28 (m, 16H), 1.18 (t, 3H, J=7.5 Hz), 0.91 (t, 3H, J=7 Hz). 13C NMR (125 MHz, CD3OD) δ 176.1, 171.8, 145.9, 130.7, 129.0, 127.9, 68.1, 62.5, 53.3, 36.7, 34.5, 33.1, 30.8, 30.7, 30.5, 30.4, 30.2, 27.0, 23.7, 14.5, 14.4. EI-MS (m/z): [M+1] calculated for C36H48NO3S 574.3. found 574.3.

Compound 204c.

Compound 204c was synthesized as described above for 204a using octanoic acid instead of palmitic acid in 85% yield. 1H NMR (125 MHz, CD3OD): δ=7.41-7.23 (m, 15H), 4.91 (q, 1H, J=5 Hz), 4.11 (q, 2H, J=7.5 Hz), 2.64 (dd, 1H, J=8.5 Hz, 12 Hz), 2.56 (dd, 1H, J=5 Hz, 12 Hz), 2.23 (t, 2H, J=7.5 Hz), 1.64-1.61 (m, 2H), 1.37-1.31 (m, 8H), 1.21 (t, 3H, J=7.5 Hz), 0.91 (t, 3H, J=7 Hz). 13C NMR (125 MHz, CD3OD) δ 176.1, 171.8, 145.9, 130.7, 129.0, 127.9, 68.1, 62.5, 53.3, 36.7, 34.5, 33.1, 30.5, 30.4, 30.2, 23.7, 14.5, 14.4. EI-MS (m/z): [M+1] calculated for C32H40NO3S 518.3. found 518.3.

Compound 204d.

Compound 204d was synthesized as described above for 204a using butyric acid instead of palmitic acid in 80% yield. 1H NMR (500 MHz, CD3OD): δ=7.41-7.23 (m, 15H), 4.60 (q, 1H, J=5 Hz), 4.21 (q, 2H, J=7.5 Hz), 2.64 (dd, 1H, J=8.5 Hz, 12 Hz), 2.56 (dd, 1H, J=5 Hz, 12 Hz), 2.27 (t, 2H, J=7 Hz), 1.70-1.64 (m, 2H), 1.30 (t, 3H, J=7.5 Hz), 0.99 (t, 3H, J=7 Hz). 13C NMR (125 MHz, CD3OD) δ 175.0, 171.8, 145.9, 130.7, 129.0, 127.9, 68.1, 62.5, 53.3, 37.3, 30.2, 22.5, 14.4, 14.3. EI-MS (m/z): [M+1] calculated for C28H32NO3S 462.2. found 462.2.

Compound 204e.

To a solution of S-Trityl-L-Cysteine ethyl ester (203) (17 mg, 0.043 mmol) in 3 mL of ice cold NaOH (1N) drop by drop was added 100 μL of acetic anhydride with vigorous stirring and continuous cooling in an ice bath. More ice cold NaOH (1N) was added, followed by 100 μL of acetic anhydride. After the mixture was stirred for 30 min the solution was brought to pH 3 by the addition of conc. H2SO4 and washed with ethyl acetate. The organic layer was dried over MgSO4, concentrated in vacuo and purified by RP-HPLC using 20-80% water/acetonirile gradient (no TFA added) over 20 min to give pure 204e (mg, 88%) as a white powder. 1H NMR (500 MHz, CD3OD): δ=7.41-7.23 (m, 15H), 4.29 (q, 1H, J=5 Hz), 4.10 (q, 2H, J=7.5 Hz), 2.62 (dd, 1H, J=8.5 Hz, 12 Hz), 2.56 (dd, 1H, J=5 Hz, 12 Hz), 1.98 (s, 3H), 1.20 (t, 3H, J=7.5 Hz). 13C NMR (125 MHz, CD3OD) δ 174.8, 171.8, 145.9, 130.7, 129.0, 127.9, 68.1, 62.5, 53.4, 30.2, 18.5, 14.3. EI-MS (m/z): [M+1] calculated for C26H28NO3S 434.2. found 434.2.

Compound 207a.

In an inert atmosphere, compound 204a (28.5 mg, 0.045 mmol) was dissolved in 1.5 mL of CH2Cl2. Afterward, triethylsilane (28 μL, 0.18 mmol), and trifluoroacetic acid (1.5 mL) were added subsequently. After 2 hr, the solvent was removed in vacuo and the resulting residue was placed on the high vacuum pump for 1 hr. The residue was resuspended in 1.5 mL of dry DMF and to it was added compound 206 (22.8 mg, 0.045 mmol). After stirring overnight at room temperature under nitrogen atmosphere, the reaction was quenched with 1% HCl aqueous solution and washed with ethyl acetate. The organic layer was dried over Na2SO4, concentrated in vacuo and purified by column chromatography (EtOAc—pentane 1:5, then 2:1) to give pure 207a (22.2 mg, 63%) as an yellow oil. 1H NMR (500 MHz, CD3OD): δ=8.13 (d, 1H, J=9 Hz), 7.98 (d, 1H, J=2 Hz), 7.44 (dd, 1H, J=9 Hz), 5.46 (t, 1H, J=9 Hz), 4.76 (q, 1H, J=5 Hz), 4.41 (t, 2H, J=6.5 Hz), 4.21 (q, 2H, J=7.5 Hz), 3.81 (dd, 2H, J=9 Hz), 3.24 (dd, 1H, J=5 Hz, 12 Hz), 2.99 (dd, 1H, J=8.5 Hz, 12 Hz), 2.89 (t, 2H, J=6.5 Hz), 2.28 (t, 3H, J=7 Hz), 2.16 (m, 2H), 1.63-1.60 (m, 2H), 1.34-1.27 (m, 27H), 0.91 (t, 3H, J=7 Hz). 13C NMR (125 MHz, CDCl3): δ=173.4, 172.2, 170.7, 168.0, 160.9, 153.6, 151.4, 149.5, 137.0, 125.6, 121.7, 114.5, 78.2, 68.4, 62.3, 51.9, 41.1, 38.9, 36.7, 34.7, 30.6, 30.0, 29.9, 29.8, 29.6, 29.5, 29.1, 25.8, 24.0, 23.3, 23.0, 14.4, 14.3, 11.2 ppm. MS (m/z): [M+1] calculated for C36H54N3O8S4 784.3. found (MALDI) 784.3.

Compound 207b.

Compound 207b was synthesized as described above for 207a using 204b as a precursor in 67% yield. 1H NMR (500 MHz, CD3OD): δ=8.11 (d, 1H, J=9 Hz), 7.98 (d, 1H, J=2 Hz), 7.44 (dd, 1H, J=9 Hz), 5.46 (t, 1H, J=9 Hz), 4.76 (q, 1H, J=5 Hz), 4.41 (t, 2H, J=6.5 Hz), 4.21 (q, 2H, J=7.5 Hz), 3.81 (dd, 2H, J=9 Hz), 3.24 (dd, 1H, J=5 Hz, 12 Hz), 2.99 (dd, 1H, J=8.5 Hz, 12 Hz), 2.89 (t, 2H, J=6.5 Hz), 2.27 (t, 3H, J=7 Hz), 2.15 (m, 2H), 1.63-1.60 (m, 2H), 1.34-1.27 (m, 19H), 0.91 (t, 3H, J=7 Hz). MS (m/z): [M+1] calculated for C32H46N3O8S4 728.2. found (MALDI) 728.2.

Compound 207c.

Compound 207c was synthesized as described above for 207a using 204c as a precursor in 72% yield. 1H NMR (500 MHz, CD3OD): δ=8.13 (d, 1H, J=9 Hz), 7.98 (d, 1H, J=2 Hz), 7.44 (dd, 1H, J=9 Hz), 5.41 (t, 1H, J=9 Hz), 4.76 (q, 1H, J=5 Hz), 4.41 (t, 2H, J=6.5 Hz), 4.21 (q, 2H, J=7.5 Hz), 3.81 (dd, 2H, J=9 Hz), 3.24 (dd, 1H, J=5 Hz, 12 Hz), 2.99 (dd, 1H, J=8.5 Hz, 12 Hz), 2.89 (t, 2H, J=6.5 Hz), 2.28 (t, 3H, J=7 Hz), 2.16 (m, 2H), 1.63-1.60 (m, 2H), 1.34-1.27 (m, 11H), 0.91 (t, 3H, J=7 Hz). MS (m/z): [M+1] calculated for C28H38N3O8S4 672.1. found (MALDI) 672.2.

Compound 207d.

Compound 207d was synthesized as described above for 207a using 204d as a precursor in 65% yield. 1H NMR (500

MHz, CD3OD): δ=8.12 (d, 1H, J=9 Hz), 7.97 (d, 1H, J=2 Hz), 7.44 (dd, 1H, J=9 Hz), 5.44 (t, 1H, J=9 Hz), 4.76 (q, 1H, J=5 Hz), 4.41 (t, 2H, J=6.5 Hz), 4.21 (q, 2H, J=7.5 Hz), 3.81 (dd, 2H, J=9 Hz), 3.24 (dd, 1H, J=5 Hz, 12 Hz), 2.99 (dd, 1H, J=8.5 Hz, 12 Hz), 2.89 (t, 2H, J=6.5 Hz), 2.27 (t, 3H, J=7 Hz), 2.16 (m, 2H), 1.69-1.65 (m, 2H), 1.30 (t, 3H, J=7.5 Hz), 0.99 (t, 3H, J=7 Hz). 13C NMR (100 MHz, CDCl3): δ=173.7, 172.3, 170.7, 167.5, 160.9, 153.5, 151.3, 149.5, 137.0, 125.6, 121.6, 114.5, 78.2, 66.7, 62.4, 52.0, 41.1, 38.6, 37.1, 36.9, 35.2, 19.2, 14.4, 13.9 ppm. MS (m/z): [M+1] calculated for $C_{24}H_{30}N_3O_8S_4$ 616.1. found (MALDI) 616.1.

Compound 207e.

Compound 207e was synthesized as described above for 207a using 204e as a precursor in 68% yield. 1H NMR (500 MHz, CD3OD): δ=8.11 (d, 1H, J=9 Hz), 7.98 (d, 1H, J=2 Hz), 7.44 (dd, 1H, J=9 Hz), 5.41 (t, 1H, J=9 Hz), 4.76 (q, 1H, J=5 Hz), 4.41 (t, 2H, J=6.5 Hz), 4.21 (q, 2H, J=7.5 Hz), 3.81 (dd, 2H, J=9 Hz), 3.23 (dd, 1H, J=5 Hz, 12 Hz), 2.99 (dd, 1H, J=8.5 Hz, 12 Hz), 2.90 (t, 2H, J=6.5 Hz), 2.21 (s, 3H), 2.16 (m, 2H), 1.30 (t, 3H, J=7.5 Hz) ppm. 13C NMR (100 MHz, CDCl3): δ=173.8, 171.1, 170.4, 166.9, 160.8, 153.5, 151.3, 150.2, 137.1, 125.7, 121.3, 114.5, 78.1, 67.4, 62.5, 52.1, 40.6, 34.8, 28.1, 23.4, 13.9 ppm. MS (m/z): [M+1] calculated for $C_{22}H_{26}N_3O_8S_4$ 588.1. found (MALDI) 588.1.

Compounds 206 and 208.

Synthesis and characterization of compounds 206 and 208 has been previously described (Jones et al., J. Am. Chem. Soc. 128:6526-6527 (2006). Compound 206. (13C NMR (125 MHz, CD3OD): δ=172.4, 167.7, 160.9, 160.4, 159.3, 153.5, 151.3, 150.1, 147.2, 140.5, 137.0, 125.6, 122.2, 121.3, 114.5, 78.1, 67.2, 35.3, 28.1 ppm.

Cellular Assays for Luciferin Release from Conjugates 207a-e.

Figure 13:
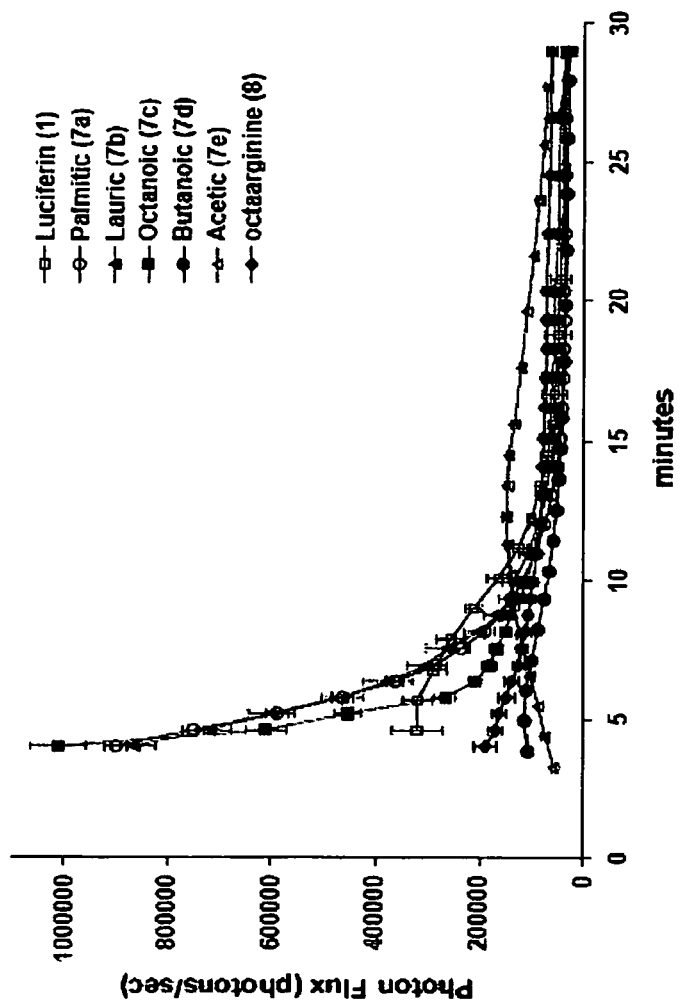
FIG. 13 depicts the results of the cell uptake experiment of Example 10 (1 min pulse, 10 μM concentration) of the lipidated transporters with a different length of a lipid tail. The compounds indicated in FIG. 13 are as follows: 7a is compound 207a of Example 10; 7b is compound 207b of Example 10; 7c is compound 207c of Example 10; 7d is compound 207d of Example 10; 7e is compound 207e of Example 10; 8 is compound 208 of Example 10.

To study uptake and release in cell culture, varying concentrations of luciferin (201) and conjugates (207a-e, 208) were incubated separately with cells. After an incubation time of 1 min, selected to facilitate measurement and not to maximize uptake, the cells were washed to remove any extracellular luciferin or conjugate, and the number of photons produced as a function of time was analyzed using a charge-coupled device camera (IVIS100, Xenogen Corp., Alameda, Calif.). The amount of luminescent signal, which is a measure of the intracellular release of free luciferin and its turnover by intracellular luciferase, was proportional to the concentration (data not shown), with a typical uptake curves shown in FIG. 13. The luminescent signal from cells pulsed with 207a-c gradually decayed reaching background after approximately 15 min (FIG. 13). Cells treated with 207d-e generated a different curve, that shape was similar to luciferin, with less initial light, a slower rate of decay, and only fraction of the total photons produced when compared to that seen for 207a-c (FIG. 13). The procedure described previously has been followed with minor variations on the vehicle in which compounds were applied (Jones et al., J. Am. Chem. Soc. 128:6526-6527 (2006)). A prostate tumor cell line, stably transfected with luciferase, PC3M-luc, was plated at 60,000 cells per well in 96 well, flat bottomed plates twelve hours prior to the assay. The cells were incubated with varying concentrations of either the potassium salt of luciferin (Xenogen Corp., Alameda, Calif.) or lipided carbonates 207a-e, in triplicate, for 1 minute, in Hepes buffered saline (HBS) pH 7.4. Compounds were administered in DMSO since they are not soluble in aqueous buffers, to get 10 μM final concentration of the tested compound in each well. Total concentration of DMSO was kept under 2% in a well in total. After the incubation the cells were washed, resuspended with the appropriate buffer, and the resultant luminescence was measured using a charged coupled device camera and Living Image software ((IVIS200, Xenogen, Corp., Alameda, Calif.). FIG. 13 depicts the results of the cell uptake experiment (1 min pulse, 10 μM concentration) of the lipidated transporters with a different length of a lipid tail. The compounds indicated in FIG. 13 are as follows: 7a is compound 207a; 7b is compound 207b; 7c is compound 207c; 7d is compound 207d; 7e is compound 207e; 8 is compound 208.

Figure 14A:
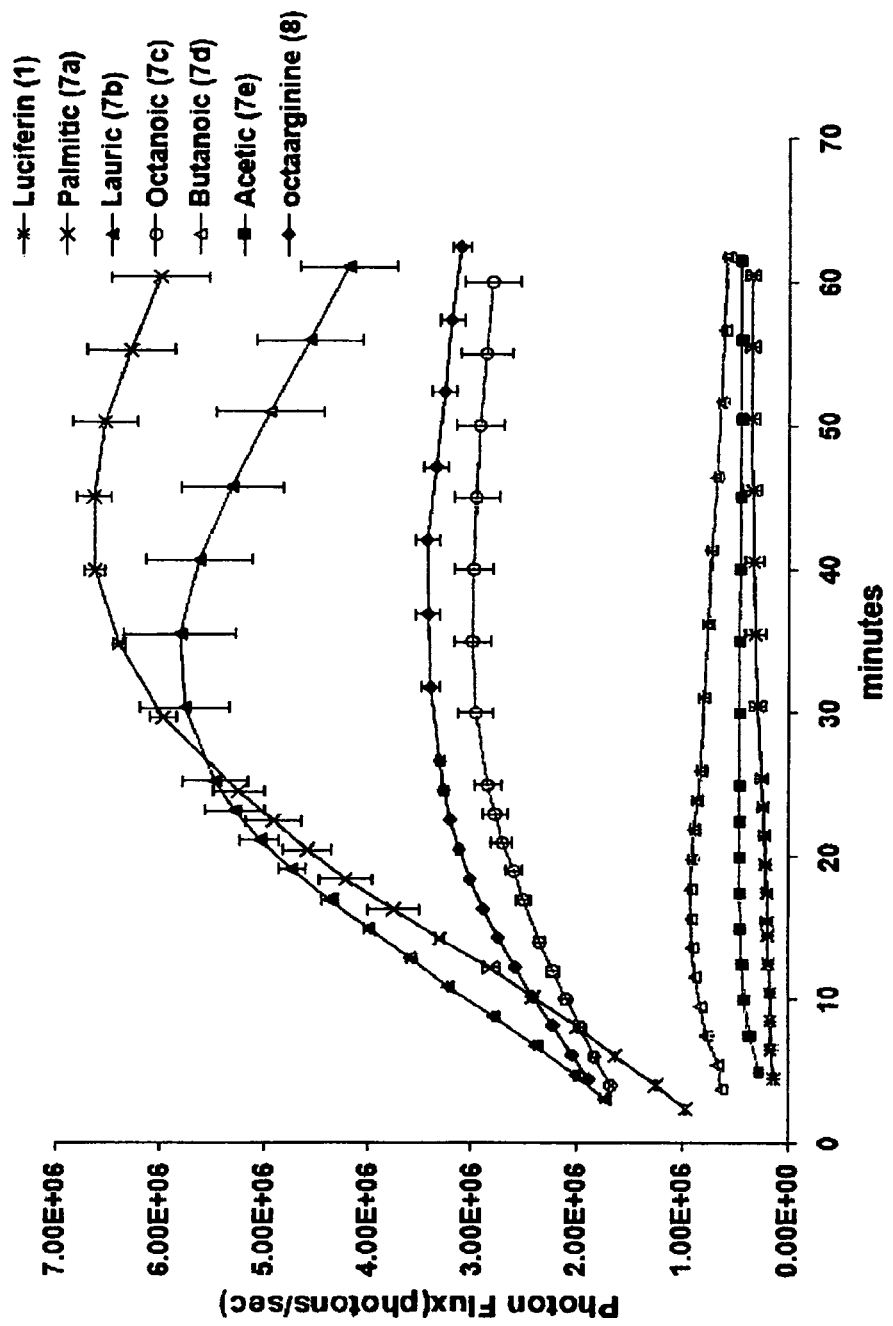
FIG. 14A depicts uptake of the lipidated transporters having different lengths of the lipid tail.

Animal Experiments:

The result of the skin uptake experiment of the lipidated transporters are shown in FIG. 14A and FIG. 14B. To assure reproducibility in the application procedure, 15 uL of 5 mmol solution of each conjugate in 100% PEG (400) were administered from a standard pipette tip (1-20 μL size) to the prepared skin surface, that provided reproducible control of the area of application (see Example 7). No further manipulation of the sample was done, thereby avoiding variable loss of sample to a glove or glass rod that would arise from a rubbing in procedure. This procedure allowed for the comparative performance of the studied conjugates under a standard set of administration conditions. The uptake performance using this procedure is reproducible, but minimal. For therapeutic applications, administration over a larger area using a rubbing in procedure would result in greater uptake. All experiments were conducted after day 5 and before day 12 of fur removal, which has been shown to exhibited excellent reproducibility due to complete stratum corneum regrowth (see Example 7). The polyarginine conjugate of luciferin 208 in 75% PEG 400 and 25% 1 mmol NaOAc (pH=6.0) buffer was used as a positive control (Example 7). Transgenic mice treated with lauric acid conjugate (207b) generated a different curve with more initial light, a similar increasing rate of the signal over the first 30 min and a faster rate of decay (FIG. 14A). Signal from octanoic acid conjugate (207c) was similar to a polyarginine control 208, demonstrating a slightly slower rate of signal increase in the first 25 min followed by a stable signal production over the next 35 min (FIG. 14A). Consistent with cell data, conjugates 207d-e produced only a fraction of the total photons when compared to that seen for 207a-c. The number of photons produced from a known amount of luciferin independent of transporter mediated entry into skin was previously determined from the intradermal injection and calibration experiments (see Example 7). This data was used to determine the amount of luciferin delivered and released by topically administered lipidated transporter conjugates of luciferin that have different fatty acid lengths (207a-e) and to compare them to a polyarginine transporter (208), that in the same assay has been previously shown to deliver 299 nM of luciferin in a one-hour time, which is well above what is required for therapeutic activity for many drugs. Compared to 208, palmitic (207a) and lauric (207b) acid transporter conjugates were able to deliver 1.7 and 1.5 times respectively more luciferin in the same one-hour time frame (see FIG. 14B). For therapeutic applications, it is noteworthy that the area of signal readout resulting from released luciferin was larger than the area of application of the conjugate and it increased with time indicating that the conjugate moved inward and laterally after passage across the stratum corneum. The procedure previously described above in Example 7 was used for animal experiments. Equimolar concentrations of each compound were prepared based on the UV absorption and their purity was determined prior to experiment. Animals were treated with Nair® 5-10 days prior to the experiment. Aliquots of 15 μL of 5 mmol solution of each compound were applied to each animal (2 spots per animal) using 100% PEG (MW=400) vehicle. In the end of each experiment the samples were removed from the animals and its purity was determined. No presence of free luciferin was observed in any of the samples.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A composition for transporting a cargo molecule across a biological barrier comprising:
   a cargo molecule, wherein the cargo molecule is taxol;
   a transporter molecule; and
   a releasable linker of the form

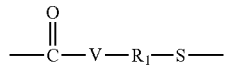

which covalently links the cargo molecule and the transporter molecule;
   where $R_1$ is an optionally substituted $C_1$-$C_8$ hydrocarbon group, an optionally substituted group of the form —$CH_2$—O—(C=O)—$C_1$-$C_8$ hydrocarbyl, or an optionally substituted $C_1$-$C_8$ hetero chain group;
   V is O; and
   the composition having the formula (I):

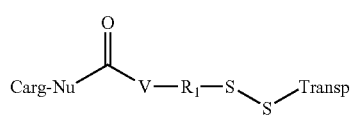

(I)

wherein Carg-Nu represents the residue of the cargo molecule "Carg-NuH", wherein Nu is O;
   and Transp-S represents the residue of a transporter molecule "Transp-SH;
   and wherein the transporter molecule is a transport polymer comprising from 6 to 25 adjacent arginines.

2. The composition of claim 1, wherein $R_1$ is $C_1$-$C_8$ alkyl.

3. The composition of claim 1, wherein $R_1$ is —$CH_2CH_2$—.

4. The composition of claim 1, wherein the composition has the formula:

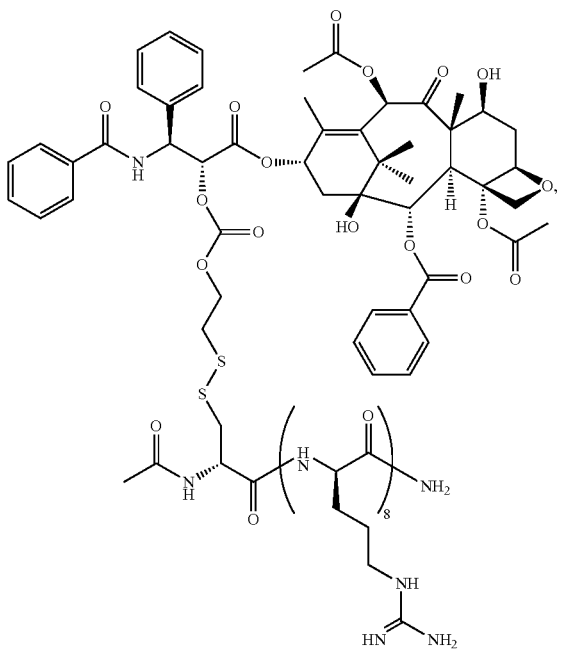

and any stereoisomer or salt thereof.

5. The composition of claim 1, wherein the transporter comprises an octaarginine moiety.

6. The composition of claim 5, wherein the transporter consists of an octaarginine moiety.

7. A method of making a conjugate of a cargo molecule "Carg-NuH", wherein the cargo molecule is a taxol and Nu is O, and a transport molecule bearing a thiol group of the form "Transp-SH", and wherein the transporter molecule is a transport polymer comprising from 6 to 25 adjacent arginines, comprising the steps of:
   reacting the compound Carg-NuH, the anion Carg-Nu(−), or the salt Carg-Nu(−) M$^+$, where -NuH or -Nu(−) is a nucleophilic moiety and M$^+$is one equivalent of a cation, with a compound of the form $Y_1$—W—$Y_2$, where $Y_1$ and $Y_2$ are leaving groups and can be the same or different, and where W is —(C=O)— to form a compound of the form:

Carg-Nu-W—$Y_1$ (IIA-gb);

reacting a compound of the form (IIIA-gb)

(IIIA-gb)

where
   $R_1$ is an optionally substituted $C_1$-$C_8$ hydrocarbon group, an optionally substituted group of the form —$CH_2$—O—(C=O)—$C_1$-$C_8$ hydrocarbyl, or an optionally substituted $C_1$-$C_8$ hetero chain group;
   V is O;
   br is an integer between 1 and 4 inclusive and indicates the number of "branches" on the $R_1$ group, and
   TLGS is a thiol leaving group stabilizer;
with the transporter molecule to form a compound of form (IVA-gb):

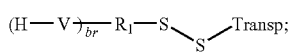
(IVA-gb)

and reacting the compound (IIA-gb) with the compound (IVA-gb) to form the conjugate of formula (Igb):

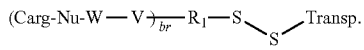
(Igb)

8. The method of claim 7, wherein br is 1.
9. The method of claim 7, wherein $R_1$ is $C_1$-$C_8$ alkyl.
10. The method of claim 9, wherein $R_1$ is —$CH_2CH_2$—.
11. The method of claim 9, wherein $R_1$ is —$CH_2CH_2CH_2$—.
12. The method of claim 9, wherein $R_1$ is —$CH_2CH_2CH_2CH_2$—.
13. The method of claim 7, wherein $M^+$ is $Li^+$, $Na^+$, $Mg^{+2}$, or $Ca^{+2}$.
14. The method of claim 7, wherein TLGS is selected from the group comprising

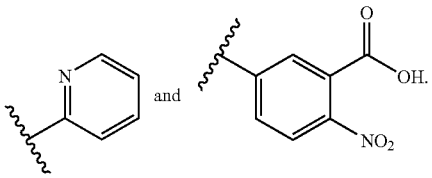 [SMILES: *c1ccccn1 ; *c1ccc([N+](=O)[O-])c(C(=O)O)c1]

* * * * *

UNITED STATES PATENT AND TRADEMARK OFFICE
CERTIFICATE OF CORRECTION

PATENT NO. : 8,653,238 B2  
APPLICATION NO. : 12/280683  
DATED : February 18, 2014  
INVENTOR(S) : Wender et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 766 days.

Signed and Sealed this

Twenty-ninth Day of September, 2015

Michelle K. Lee
*Director of the United States Patent and Trademark Office*